US008952007B2

(12) United States Patent
Abelman et al.

(10) Patent No.: US 8,952,007 B2
(45) Date of Patent: Feb. 10, 2015

(54) FUSED HETEROCYCLIC COMPOUNDS AS ION CHANNEL MODULATORS

(71) Applicant: Gilead Sciences, Inc., Foster City, CA (US)

(72) Inventors: Matthew Abelman, Encinitas, CA (US); Nancy Chu, Cupertino, CA (US); Robert H. Jiang, Cupertino, CA (US); Kwan Leung, Palo Alto, CA (US); Jeff Zablocki, Los Altos, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 14/101,740

(22) Filed: Dec. 10, 2013

(65) Prior Publication Data

US 2014/0094460 A1  Apr. 3, 2014

Related U.S. Application Data

(60) Division of application No. 13/706,786, filed on Dec. 6, 2012, now Pat. No. 8,664,379, which is a continuation of application No. 12/607,823, filed on Oct. 28, 2009, now abandoned.

(60) Provisional application No. 61/109,788, filed on Oct. 30, 2008, provisional application No. 61/161,011, filed on Mar. 17, 2009.

(51) Int. Cl.
*C07D 215/227* (2006.01)
*C07D 401/06* (2006.01)
*C07D 413/06* (2006.01)
*C07D 417/06* (2006.01)
*C07D 471/04* (2006.01)

(52) U.S. Cl.
CPC .......... *C07D 401/06* (2013.01); *C07D 215/227* (2013.01); *C07D 413/06* (2013.01); *C07D 417/06* (2013.01); *C07D 471/04* (2013.01)
USPC .......... 514/235.2; 514/312; 544/128; 546/158

(58) Field of Classification Search
None
See application file for complete search history.

(56) References Cited

FOREIGN PATENT DOCUMENTS

| DE | 19624808 A1 | 1/1998 |
|---|---|---|
| EP | 0556393 A1 | 8/1993 |
| EP | 0676397 A1 | 10/1995 |
| EP | 0784054 A1 | 7/1997 |
| EP | 1156047 A1 | 11/2001 |
| EP | 1930007 A1 | 6/2008 |
| JP | 06228112 A | 8/1994 |
| JP | 2000281676 A | 10/2000 |
| WO | WO-9308174 A1 | 4/1993 |
| WO | WO-99/46260 A1 | 9/1999 |
| WO | WO-00/66560 A1 | 11/2000 |
| WO | WO-0244157 A2 | 6/2002 |
| WO | WO-02096873 A1 | 12/2002 |
| WO | WO-2004/043950 A1 | 5/2004 |
| WO | WO-2005/092894 A1 | 10/2005 |
| WO | WO-2006/015259 A2 | 2/2006 |
| WO | WO-2006/113432 A2 | 10/2006 |
| WO | WO-2007/041112 A2 | 4/2007 |
| WO | WO-2007/112347 A1 | 10/2007 |
| WO | WO-2008144483 A2 | 11/2008 |

OTHER PUBLICATIONS

Baston E. et al. (2000) "6-Substituted 1H-quinolin-2-ones and 2-methoxy-quinolines: synthesis and evaluation as inhibitors of steroid 5 alpha reductases types 1 and 2", European Journal of Medicinal Chemistry, vol. 35, pp. 931-940.
Carta, A. et al. (2003), "Quinoxalin-2-ones. Part 5. Synthesis and antimicrobial evaluation of 3-alkyl-, 3-halomethyl- and 3-carboxyethylquinoxaline-2-ones variously substituted on the benzo-moiety," Il Farmaco, 58(12), pp. 1251-1255.
International Search Report for PCT/US2009/062244, International Filing Date Oct. 27, 2009, mailed Mar. 1, 2010.
International Search Report for PCT/US2009/062386, International Filing Date Oct. 28, 2009, mailed Apr. 12, 2010.
Krchnak, V. et al. (2000), "A solid phase traceless synthesis of quinoxalinones," XP004195682, Tetrahedron Letters, vol. 41(16), pp. 2835-2838.
Lubisch, W. et al. (1997), "Pyrrolylquinoxalinediones: a new class of AMPA receptor antagonists," XP-002566848, retrieved from STN Database Accession No. 1997:13371 Abstract, Database Caplus (Online) Chemical Abstracts Service, Columbus, Ohio, US.
Lubisch, W. et al. (1997), Pyrrolylquinoxalinediones: dicarboxylates as highly potent AMPA receptor antagonists, XP-002566846, retrieved from STN Database Accession No. 1998:723297 Abstract, Database Caplus (Online) Chemical Abstracts Service, Columbus, Ohio, US.
Lubisch, W. et al. (1997), "Pyrrolylquinoxalinediones: The importance of pyrrolic substitution on AMPA receptor binding," XP-002566847, retrieved from STN Database Accession No. 1997:357079 Abstract, Database Caplus (Online) Chemical Abstracts Service, Columbus, Ohio, US.
Menichincheri, M. et al. (2004), "Catecholic Flavonoids Acting as Telomerase Inhibitors," XP-002566850, J. Med. Chem., vol. 47, pp. 6466-6475.

(Continued)

Primary Examiner — Janet L Andres
Assistant Examiner — Timothy R Rozof
(74) Attorney, Agent, or Firm — Francis O. Ginah; J. Elin Hartrum

(57) ABSTRACT

The present invention relates to sodium channel inhibitors of Formula I:

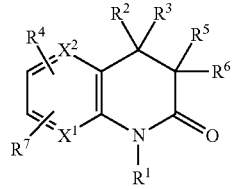

Formula (I)

in which $R^1$, $R^2$, $R^3$, $R^4$, $R^5$, $R^6$, and $R^7$ are as defined above, and to their use in the treatment of various disease states, including cardiovascular diseases and diabetes.

8 Claims, No Drawings

(56) References Cited

OTHER PUBLICATIONS

Occhiato, E.G. et al. (2004) "Synthesis, Biological Activity, and Three-Dimensional Quantitative Structure-Activity Relationship Model for a Series of Benzo [c]quinolizin-3-ones, Nonsteroidal Inhibitors of Human Steroid 5 Alpha-Reductase 1." *Journal of Medicinal Chemistry*, vol. 47, pp. 3546-3560.

Ohmori, J. et al. (1996), "Novel AMPA Receptor Antagonists: Synthesis and Structure-Activity Relationships of 1-Hydroxy-7-(1H-imidazol-1-yl)-6-nitro-2,3(1H,4H)-quinoxalinedione and Related Compounds," XP-002566849, retrieved from STN Database Accession No. 1996:544124 Abstract, Database Caplus (Online) Chemical Abstracts Service, Columbus, Ohio, US.

Rabilloud, S. (1970), Database Beilstein, Beilstein Institute for Organic Chemistry, Frankfurt-Main, DE, XP002566855, Database Accession No. BRN 1231868, Provided XRN 1231868.

Saito, Isao et al. (1968), "Chemical studies on riboflavine and related compounds. I. Oxidation of quinoxaline-2, 3-diols as a possible model for the biological decomposition of riboflavine," XP-002566854, retrieved from STN Database Accession No. 1968:10733 abstract, Database Caplus (Online) Chemical Abstracts Service, Columbus, Ohio, US.

Sakamoto, Shuichi et al. (1998), "Novel AMPA/kainate receptor antagonists," XP002566844, retrieved from STN Database Accession No. 1998:72653 Abstract, Database Caplus (Online) Chemical Abstracts Service, Columbus, Ohio, US.

Sanna, P. et al. (1998), "Synthesis of substituted 2-(ethoxycarbonyl)- and 2-carboxyquinoxalin-3-ones for evaluation of antimicrobial and anticancer activity," XP002566852, retrieved from STN Database Accession No. 1998:757899 abstract, Database Caplus (Online) Chemical Abstracts Service, Columbus, Ohio, US.

Sanna, P. et al. (1999), "Synthesis of 3, 6, 7-substituted 2-quinoxalinones for evaluation of antimicrobial and anticancer activity. Part 2," XP002566851, retrieved from STN Database Accession No. 1999:348899, Database Caplus (Online) Chemical Abstracts Service, Columbus, Ohio, US.

Sayed et al. (1987) Action of Nitrogen and Carbon Nucleophiles on 6-phenyl-3,4-dihydrocoumarin, *Oriental Journal of Chemistry* vol. 3(2) 174-178.

Takano, Y. et al. (2006), "Design and synthesis of novel 7-heterocycle-6-trifluoromethyl-3-oxoquinoxaline-2-carboxylic acids bearing a substituted phenyl group as superior AMPA receptor antagonists with good physicochemical properties," *Bioorganic & Medicinal Chemistry*, vol. 14(3), pp. 776-792.

Turski, Lechoslaw et al. (1998), "ZK200775: a phosphonate quinoxalinedione AMPA antagonist for neuroprotection in stroke and trauma," XP-002566845, retrieved from STN Database Accession No. 1998:591413 Abstract, Database Caplus (Online) Chemical Abstracts Service, Columbus, Ohio, US.

Thailand Office Action dated Apr. 8, 2011, Thai Patent Application No. 0901004866 filed on Oct. 30, 2009, entitled "Fused Heterocyclic Compounds as Ion Channel Modulators".

FUSED HETEROCYCLIC COMPOUNDS AS ION CHANNEL MODULATORS

CROSS-REFERENCE TO RELATED APPLICATIONS

This application is a divisional application of U.S. patent application Ser. No. 13/706,786, filed Dec. 6, 2012, which is a continuation of U.S. patent application Ser. No. 12/607,823, filed Oct. 28, 2009, now abandoned, which claims priority to U.S. Provisional Patent Application Ser. No. 61/161,011, filed Mar. 17, 2009 and U.S. Provisional Patent Application Ser. No. 61/109,788, filed Oct. 30, 2008, the entireties of each of which is incorporated herein by reference.

FIELD OF THE INVENTION

The present invention relates to novel compounds and to their use in the treatment of various disease states, including cardiovascular diseases and diabetes. The invention also relates to methods for their preparation, and to pharmaceutical compositions containing such compounds.

BACKGROUND

The late sodium current ($I_{NaL}$) is a sustained component of the fast $Na^+$ current of cardiac myocytes and neurons. Many common neurological and cardiac conditions are associated with abnormal ($I_{NaL}$) enhancement, which contributes to the pathogenisis of both electrical and contactile dysfunction in mammals. See, for example, Pathophysiology and Pharmacology of the Cardiac "Late Sodium Current", Pharmacology and Therapeutics 119 (2008) 326-339. Accordingly, pharmaceutical compounds that selectively inhibit ($I_{NaL}$) in mammals are useful in treating such disease states.

One example of a selective inhibitor of ($I_{NaL}$) is RANEXA®, a compound approved by the FDA for the treatment of chronic stable angina pectoris. RANEXA® has also been shown to be useful for the treatment of a variety of cardiovascular diseases, including ischemia, reperfusion injury, arrhythmia and unstable angina, and also for the treatment of diabetes. It would be desirable to provide novel compounds that selectively inhibit ($I_{NaL}$) in mammals, and that have a similar spectrum of activity as RANEXA®, but with a lower potential for blocking the potassium hERG channel.

SUMMARY OF THE INVENTION

Accordingly, the present invention provides novel compounds of Formula (I) that function as late sodium channel blockers:

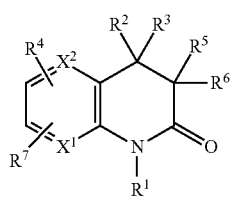

Formula (I)

wherein:

$R^1$ is hydrogen or alkyl of 1-6 carbon atoms optionally substituted by 1, 2 or 3 groups chosen from hydroxyl, alkoxy, halo, —C(O)R, aryl, cycloalkyl, heterocyclyl, and heteroaryl, wherein said aryl, cycloalkyl, heterocyclyl, or heteroaryl groups are optionally substituted by one, two, or three groups independently chosen from halo, hydroxyl, alkyl, —C(O)R, haloalkyl, alkoxy, aryl, or cycloalkyl; in which R is hydroxy, alkoxy, or —NH$_2$, $R^2$ and $R^3$ are each independently hydrogen, halo, alkoxy of 1-6 carbon atoms, optionally substituted alkyl of 1-6 carbon atoms, —CF$_3$, —O—CF$_3$, or —CN, or $R^2$ and $R^3$, taken together with the carbon to which they are both attached form an optionally substituted cycloalkyl;

$R^4$ is phenyl optionally substituted by 1, 2, or 3 substituents independently selected from the group consisting of alkyl of 1-6 carbon atoms, cycloalkyl, aryl, heteroaryl, heterocyclyl, halo, —NO$_2$, —CF$_3$, —O—CF$_3$, —CN, —O—R$^8$, —S—R$^8$, —N(R$^8$)(R$^9$), —S(=O)—R$^8$, —S(=O)$_2$R$^8$, —S(=O)$_2$—N(R$^8$)(R$^9$), —S(=O)$_2$—O—R$^8$, —N(R$^8$)—C(O)—R$^9$, —N(R$^8$)—C(O)—O—R$^9$, —N(R$^8$)—C(O)—N(R$^8$)(R$^9$), —C(O)—R$^8$, —C(O)—O—R$^8$, —C(O)—N(R$^8$)(R$^9$), and —N(R$^8$)—S(=O)$_2$—R$^9$, wherein each said alkyl, cycloalkyl, aryl, heteroaryl, and heterocyclyl is further optionally substituted with halo, —NO$_2$, —CF$_3$, —O—CF$_3$, —N(R$^8$)(R$^9$), —C(O)—R$^8$, —C(O)—O—R$^8$, —C(O)—N(R$^8$)(R$^9$), —CN, or —O—R$^8$, in which R$^8$ and R$^9$ are independently chosen from the group consisting of hydrogen, alkyl of 1-6 carbon atoms, heterocyclyl, aryl, and heteroaryl, wherein the alkyl, heterocyclyl, aryl, and heteroaryl are optionally substituted with one, two, or three substituents independently selected from halo, alkyl, mono- or dialkylamino, alkyl or aryl;

$R^5$ and $R^6$ are each independently hydrogen, halo, alkoxy, optionally substituted alkyl of 1-6 carbon atoms, —CF$_3$, —O—CF$_3$, or —CN, or $R^5$ and $R^6$, taken together with the carbon to which they are both attached form an optionally substituted cycloalkyl;

$R^7$ is hydrogen, halo, cyano, or alkyl of 1-6 carbon atoms optionally substituted by hydroxyl, alkoxy, halo, or —C(O)R, $X^1$ and $X^2$ are independently —N= or —C(R$^{10}$)=, wherein R$^{10}$ is selected from hydrogen, halo, hydroxyl, alkyl of 1-6 carbon atoms, alkoxy of 1-6 carbon atoms, —CF$_3$, —O—CF$_3$, —CN, or —N(R$^8$)(R$^9$);

and the pharmaceutically acceptable salts, esters, prodrugs, or solvates thereof.

One embodiment of the invention includes compounds of Formula (I) in which $X^1$ and $X^2$ are both —C(R$^{10}$)=, particularly where R$^{10}$ is hydrogen. Within this group are included compounds of Formula (I) in which R$^2$ and R$^3$ are hydrogen or lower alkyl of 1-6 carbon atoms, and R$^5$ and R$^6$ are hydrogen. Within this group is a subgroup of compounds of Formula (I) in which R$^1$ is hydrogen or alkyl of 1-6 carbon atoms optionally substituted by hydroxy, —C(O)R, trifluoromethyl, alkoxy of 1-6 carbon atoms, or phenyl optionally substituted by —C(O)R.

Within this subgroup are compounds of Formula (I) in which R$^7$ is hydrogen and R$^4$ is phenyl optionally substituted by 1, 2, or 3 substituents independently selected from the group consisting of hydrogen, alkyl, hydroxyl, alkoxy, cyano, —C(O)NH$_2$, halo, or alkyl substituted by 1, 2, 3, 4, 5 or 6 halo atoms, particularly fluoro.

In another embodiment, R$^1$ is hydrogen, alkyl of 1-6 carbon atoms optionally substituted by 1, 2 or 3 groups chosen from —C(O)R, halo, hydroxy, heteroaryl substituted by optionally substituted phenyl, or phenyl optionally substituted by —C(O)R, and R$^2$ is methoxy, particularly where R$^4$ is 6-(4-chlorophenyl) or 6-(4-trifluoromethylphenyl).

In another embodiment, R$^1$ is hydrogen or —C(O)R, where R is hydroxy, alkoxy of 1-6 carbon atoms, or —NH$_2$.

One embodiment provides a method of using the compounds of Formula (I) in the treatment of a disease or condition in a mammal that is amenable to treatment by a late sodium channel blocker. The compounds of the invention and their therapeutically acceptable salts, esters, tautomeric forms are of use as medicaments for the treatment of certain diseases, such as, cardiovascular diseases such as atrial and ventricular arrhythmias, heart failure (including congestive heart failure, diastolic heart failure, systolic heart failure, acute heart failure), Prinzmetal's (variant) angina, stable and unstable angina, exercise induced angina, congestive heart disease, ischemia, recurrent ischemia, reperfusion injury, myocardial infarction, acute coronary syndrome, peripheral arterial disease, and intermittent claudication. Such diseases may also include diabetes, and conditions related to diabetes, e.g. diabetic peripheral neuropathy. Such diseases may also include conditions affecting the neuromuscular system resulting in pain, seizures, epilepsy, or paralysis. Such diseases may also include cerebrovascular disorders, such as stroke.

In another embodiment the invention provides pharmaceutical formulations comprising a therapeutically effective amount of a compound of the invention (e.g. a compound of Formula (I)) and at least one pharmaceutically acceptable excipient.

At present, the preferred compounds of the invention include, but are not limited to:

6-(3-fluorophenyl)-3,4-dihydroquinolin-2(1H)-one;
4-(2-oxo-1,2,3,4-tetrahydroquinolin-6-yl)benzamide;
6-(4-fluorophenyl)-3,4-dihydroquinolin-2(1H)-one;
6-phenyl-3,4-dihydroquinolin-2(1H)-one;
4-(2-oxo-1,2,3,4-tetrahydroquinolin-6-yl)benzonitrile;
3-(2-oxo-1,2,3,4-tetrahydroquinolin-6-yl)benzamide;
6-(2-fluorophenyl)-3,4-dihydroquinolin-2(1H)-one;
6-(3-acetylphenyl)-3,4-dihydroquinolin-2(1H)-one;
6-(3-fluorophenyl)-1-methyl-3,4-dihydroquinolin-2(1H)-one;
6-[4-(trifluoromethyl)phenyl]-3,4-dihydroquinolin-2(1H)-one;
6-[4-chloro-3-(trifluoromethyl)phenyl]-3,4-dihydroquinolin-2(1H)-one;
6-(2,4-difluorophenyl)-3,4-dihydroquinolin-2(1H)-one;
2-fluoro-5-(2-oxo-1,2,3,4-tetrahydroquinolin-6-yl)benzonitrile;
6-[3-(trifluoromethyl)phenyl]-3,4-dihydroquinolin-2(1H)-one;
ethyl[6-(2,4-difluorophenyl)-2-oxo-3,4-dihydroquinolin-1(2H)-yl]acetate;
1-(2-hydroxyethyl)-6-[4-(trifluoromethyl)phenyl]-3,4-dihydroquinolin-2(1H)-one;
ethyl[6-(3,4-difluorophenyl)-2-oxo-3,4-dihydroquinolin-1 (2H)-yl]acetate;
6-(3,4-difluorophenyl)-1-(2-hydroxyethyl)-3,4-dihydroquinolin-2(1H)-one;
6-(2,4-difluorophenyl)-1-(2-hydroxyethyl)-3,4-dihydroquinolin-2(1H)-one;
ethyl {2-oxo-6-[3-(trifluoromethoxy)phenyl]-3,4-dihydroquinolin-1 (2H)-yl}acetate;
{2-oxo-6-[4-(trifluoromethyl)phenyl]-3,4-dihydroquinolin-1 (2H)-yl}acetic acid;
ethyl {2-oxo-6-[4-(trifluoromethoxy)phenyl]-3,4-dihydroquinolin-1(2H)-yl}acetate;
{2-oxo-6-[3-(trifluoromethoxy)phenyl]-3,4-dihydroquinolin-1(2H)-yl}acetic acid;
1-{[2-(4-chlorophenyl)-1,3-thiazol-4-yl]methyl}-6-(2,4-difluorophenyl)-3,4-dihydroquinolin-2(1H)-one;
6-(2,4-difluorophenyl)-1-(2-methoxyethyl)-3,4-dihydroquinolin-2(1H)-one;
6-(2,4-difluorophenyl)-1-(2,2,2-trifluoroethyl)-3,4-dihydroquinolin-2(1H)-one;
6-(2,4-difluorophenyl)-1-[2-hydroxy-3-(2-methoxyphenoxy)propyl]-3,4-dihydroquinolin-2(1H)-one;
tert-butyl {2-oxo-6-[4-(trifluoromethyl)phenyl]-3,4-dihydroquinolin-1 (2H)-yl}acetate;
tert-butyl[6-(2,4-difluorophenyl)-2-oxo-3,4-dihydroquinolin-1 (2H)-yl]acetate;
1-(2-hydroxyethyl)-6-[4-(trifluoromethoxy)phenyl]-3,4-dihydroquinolin-2(1H)-one;
2-{2-oxo-6-[4-(trifluoromethoxy)phenyl]-3,4-dihydroquinolin-1 (2H)-yl}acetamide;
1-[2-(morpholin-4-yl)-2-oxoethyl]-6-[4-(trifluoromethyl)phenyl]-3,4-dihydroquinolin-2(1H)-one;
tert-butyl[6-(4-fluorophenyl)-2-oxo-3,4-dihydroquinolin-1 (2H)-yl]acetate;
[6-(4-fluorophenyl)-2-oxo-3,4-dihydroquinolin-1 (2H)-yl]acetic acid;
{2-oxo-6-[4-(trifluoromethyl)phenyl]-3,4-dihydroquinolin-1(2H)-yl}acetonitrile;
1-(2-methoxyethyl)-6-[4-(trifluoromethyl)phenyl]-3,4-dihydroquinolin-2(1H)-one;
6-[4-(trifluoromethoxy)phenyl]-3,4-dihydroquinolin-2 (1H)-one;
tert-butyl {2-oxo-6-[4-(trifluoromethoxy)phenyl]-3,4-dihydroquinolin-1 (2H)-yl}acetate;
{2-oxo-6-[4-(trifluoromethoxy)phenyl]-3,4-dihydroquinolin-1(2H)-yl}acetic acid;
sodium {2-oxo-6-[4-(trifluoromethyl)phenyl]-3,4-dihydroquinolin-1(2H)-yl}acetate;
tert-butyl[6-(3-chlorophenyl)-2-oxo-3,4-dihydroquinolin-1(2H)-yl]acetate;
1-[(5-tert-butyl-1,2,4-oxadiazol-3-yl)methyl]-6-(4-fluorophenyl)-3,4-dihydroquinolin-2(1H)-one;
1-(2-hydroxypropyl)-6-[4-(trifluoromethoxy)phenyl]-3,4-dihydroquinolin-2(1H)-one;
6-(4-chlorophenyl)-3,4-dihydroquinolin-2(1H)-one;
1-(pyridin-3-ylmethyl)-6-[4-(trifluoromethoxy)phenyl]-3,4-dihydroquinolin-2(1H)-one;
6-(4-phenoxyphenyl)-3,4-dihydroquinolin-2(1H)-one;
1-[(5-methylisoxazol-3-yl)methyl]-6-[4-(trifluoromethoxy)phenyl]-3,4-dihydroquinolin-2(1H)-one;
tert-butyl[6-(4-chlorophenyl)-2-oxo-3,4-dihydroquinolin-1(2H)-yl]acetate;
tert-butyl[2-oxo-6-(4-phenoxyphenyl)-3,4-dihydroquinolin-1(2H)-yl]acetate;
tert-butyl {6-[4-chloro-3-(trifluoromethyl)phenyl]-2-oxo-3,4-dihydroquinolin-1 (2H)-yl}acetate;
[6-(4-chlorophenyl)-2-oxo-3,4-dihydroquinolin-1(2H)-yl]acetic acid;
[6-(3,4-dichlorophenyl)-2-oxo-3,4-dihydroquinolin-1 (2H)-yl]acetic acid;
[2-oxo-6-(4-phenoxyphenyl)-3,4-dihydroquinolin-1 (2H)-yl]acetic acid;
3-(2-oxo-1,2,3,4-tetrahydroquinolin-6-yl)benzonitrile;
ethyl {2-oxo-6-[4-(trifluoromethyl)phenyl]-3,4-dihydroquinolin-1(2H)-yl}acetate;
2-[6-(2,4-difluorophenyl)-2-oxo-3,4-dihydroquinolin-1 (2H)-yl]acetamide;
2-{2-oxo-6-[4-(trifluoromethyl)phenyl]-3,4-dihydroquinolin-1 (2H)-yl}acetamide;
2-{6-[4-chloro-3-(trifluoromethyl)phenyl]-2-oxo-3,4-dihydroquinolin-1 (2H)-yl}acetamide;
[6-(4-chloro-3-fluorophenyl)-2-oxo-3,4-dihydroquinolin-1(2H)-yl]acetic acid;

6-(4-chlorophenyl)-7-methoxy-3,4-dihydroquinolin-2 (1H)-one;

8-bromo-6-(4-chlorophenyl)-7-methoxy-3,4-dihydroquinolin-2(1H)-one;

{7-methoxy-2-oxo-6-[4-(trifluoromethyl)phenyl]-3,4-dihydroquinolin-1 (2H)-yl}acetic acid;

[6-(4-chlorophenyl)-7-methoxy-2-oxo-3,4-dihydroquinolin-1(2H)-yl]acetic acid;

[6,8-bis(4-chlorophenyl)-7-methoxy-2-oxo-3,4-dihydroquinolin-1(2H)-yl]acetic acid;

4,4-dimethyl-6-[4-(trifluoromethyl)phenyl]-3,4-dihydroquinolin-2(1H)-one;

{4,4-dimethyl-2-oxo-6-[4-(trifluoromethyl)phenyl]-3,4-dihydroquinolin-1(2H)-yl}acetic acid;

[6-(3-chloro-4-fluorophenyl)-2-oxo-3,4-dihydroquinolin-1(2H)-yl]acetic acid;

[6-(3-fluorophenyl)-2-oxo-3,4-dihydroquinolin-1(2H)-yl]acetic acid;

4-((2-oxo-6-(4-(trifluoromethyl)phenyl)-3,4-dihydroquinolin-1 (2H)-yl)methyl)benzoic acid;

methyl 4-((2-oxo-6-(4-(trifluoromethyl)phenyl)-3,4-dihydroquinolin-1(2H)-yl)methyl)benzoate;

6-(3-fluoro-4-(trifluoromethyl)phenyl)-3,4-dihydroquinolin-2(1H)-one;

2-(6-(3-fluoro-4-(trifluoromethyl)phenyl)-2-oxo-3,4-dihydroquinolin-1(2H)-yl)acetic acid;

tert-butyl 2-(6-(3-fluoro-4-(trifluoromethyl)phenyl)-2-oxo-3,4-dihydroquinolin-1(2H)-yl)acetate;

ethyl 3-((2-oxo-6-(4-(trifluoromethyl)phenyl)-3,4-dihydroquinolin-1(2H)-yl)methyl)benzoate;

6-(3-fluoro-4-(trifluoromethyl)phenyl)-7-methoxy-3,4-dihydroquinolin-2(1H)-one;

7-methoxy-6-[4-(trifluoromethyl)phenyl]-3,4-dihydroquinolin-2(1H)-one;

6,8-bis(4-chlorophenyl)-7-methoxy-3,4-dihydroquinolin-2(1H)-one;

6-[3-(morpholin-4-ylcarbonyl)phenyl]-3,4-dihydroquinolin-2(1H)-one;

tert-butyl 2-(6-(3,4-dichlorophenyl)-2-oxo-3,4-dihydroquinolin-1(2H)-yl)acetate;

tert-butyl-2-(7-methoxy-2-oxo-6-(4-(trifluoromethyl)phenyl)-3,4-dihydroquinolin-1(2H)-yl)acetate;

1-benzyl-6-(2,4-difluorophenyl)-3,4-dihydroquinolin-2(1H)-one; and 2-(2-oxo-6-(4-(trifluoromethoxy)phenyl)-3,4-dihydroquinolin-1(2H)-yl)acetic acid.

DETAILED DESCRIPTION OF THE INVENTION

Definitions and General Parameters

As used in the present specification, the following words and phrases are generally intended to have the meanings as set forth below, except to the extent that the context in which they are used indicates otherwise.

The term "alkyl" refers to a monoradical branched or unbranched saturated hydrocarbon chain having from 1 to 20 carbon atoms. This term is exemplified by groups such as methyl, ethyl, n-propyl, iso-propyl, n-butyl, iso-butyl, t-butyl, n-hexyl, n-decyl, tetradecyl, and the like.

The term "substituted alkyl" refers to:
1) an alkyl group as defined above, having 1, 2, 3, 4 or 5 substituents, (typically 1, 2, or 3 substituents) selected from the group consisting of alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2; or
2) an alkyl group as defined above that is interrupted by 1-10 atoms (e.g. 1, 2, 3, 4, or 5 atoms) independently chosen from oxygen, sulfur and NRa—, where Ra is chosen from hydrogen, alkyl, cycloalkyl, alkenyl, cycloalkenyl, alkynyl, aryl, heteroaryl and heterocyclyl. All substituents may be optionally further substituted by alkyl, alkoxy, halogen, $CF_3$, amino, substituted amino, cyano, or —$S(O)_nR$, in which R is alkyl, aryl, or heteroaryl and n is 0, 1 or 2; or
3) an alkyl group as defined above that has both 1, 2, 3, 4 or 5 substituents as defined above and is also interrupted by 1-10 atoms (e.g. 1, 2, 3, 4, or 5 atoms) as defined above.

The term "lower alkyl" refers to a monoradical branched or unbranched saturated hydrocarbon chain having 1, 2, 3, 4, 5, or 6 carbon atoms. This term is exemplified by groups such as methyl, ethyl, n-propyl, iso-propyl, n-butyl, iso-butyl, t-butyl, n-hexyl, and the like.

The term "substituted lower alkyl" refers to lower alkyl as defined above having 1 to 5 substituents (typically 1, 2, or 3 substituents), as defined for substituted alkyl, or a lower alkyl group as defined above that is interrupted by 1, 2, 3, 4, or 5 atoms as defined for substituted alkyl, or a lower alkyl group as defined above that has both 1, 2, 3, 4 or 5 substituents as defined above and is also interrupted by 1, 2, 3, 4, or 5 atoms as defined above.

The term "alkylene" refers to a diradical of a branched or unbranched saturated hydrocarbon chain, typically having from 1 to 20 carbon atoms (e.g. 1-10 carbon atoms, or 1, 2, 3, 4, 5 or 6 carbon atoms). This term is exemplified by groups such as methylene (—$CH_2$—), ethylene (—$CH_2CH_2$—), the propylene isomers (e.g., —$CH_2CH_2CH_2$— and —$CH(CH_3)CH_2$—), and the like.

The term "lower alkylene" refers to a diradical of a branched or unbranched saturated hydrocarbon chain, typically having 1, 2, 3, 4, 5, or 6 carbon atoms.

The term "substituted alkylene" refers to:
(1) an alkylene group as defined above having 1, 2, 3, 4, or 5 substituents (typically 1, 2, or 3 substituents) selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2; or
(2) an alkylene group as defined above that is interrupted by 1-10 groups (e.g. 1, 2, 3, 4, or 5 groups) independently chosen from —O—, —S—, sulfonyl, —C(O)—, —C(O)O—, —C(O)N—, and —NRa—, where Ra is chosen from hydrogen, optionally substituted alkyl, cycloalkyl, cycloalkenyl, aryl, heteroaryl and heterocyclyl; or (3) an alkylene group as defined above that has both 1, 2, 3, 4 or 5 substituents as defined above and is also interrupted by 1-10 groups as defined above. Examples of substituted alkylenes are chloromethylene (—CH(Cl)—), aminoethylene (—CH(NH$_2$)CH$_2$—), methylaminoethylene (—CH(NHMe)CH$_2$—), 2-carboxypropylene isomers (—CH$_2$CH(CO$_2$H)CH$_2$—), ethoxyethyl (—CH$_2$CH$_2$O—CH$_2$CH$_2$—), ethylmethylaminoethyl (—CH$_2$CH$_2$—N(CH$_3$)—CH$_2$CH$_2$—), 1-ethoxy-2-(2-ethoxy-ethoxy)ethane (—CH$_2$CH$_2$O—CH$_2$CH$_2$—OCH$_2$CH$_2$—OCH$_2$CH$_2$—), and the like.

The term "aralkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "alkoxy" refers to the group R—O—, where R is optionally substituted alkyl or optionally substituted cycloalkyl, or R is a group —Y—Z, in which Y is optionally substituted alkylene and Z is optionally substituted alkenyl, optionally substituted alkynyl; or optionally substituted cycloalkenyl, where alkyl, alkenyl, alkynyl, cycloalkyl and cycloalkenyl are as defined herein. Typical alkoxy groups are alkyl-O— and include, by way of example, methoxy, ethoxy, n-propoxy, iso-propoxy, n-butoxy, tert-butoxy, sec-butoxy, n-pentoxy, n-hexyloxy, 1,2-dimethylbutoxy, and the like.

The term "lower alkoxy" refers to the group R—O— in which R is optionally substituted lower alkyl as defined above. This term is exemplified by groups such as methoxy, ethoxy, n-propoxy, iso-propoxy, n-butoxy, iso-butoxy, t-butoxy, n-hexyloxy, and the like.

The term "alkylthio" refers to the group R—S—, where R is as defined for alkoxy.

The term "alkenyl" refers to a monoradical of a branched or unbranched unsaturated hydrocarbon group typically having from 2 to 20 carbon atoms (more typically from 2 to 10 carbon atoms, e.g. 2 to 6 carbon atoms) and having from 1 to 6 carbon-carbon double bonds, e.g. 1, 2, or 3 carbon-carbon double bonds. Typical alkenyl groups include ethenyl (or vinyl, i.e. —CH=CH$_2$), 1-propylene (or allyl, —CH$_2$CH=CH$_2$), isopropylene (—C(CH$_3$)=CH$_2$), bicyclo[2.2.1]heptene, and the like. In the event that alkenyl is attached to nitrogen, the double bond cannot be alpha to the nitrogen.

The term "lower alkenyl" refers to alkenyl as defined above having from 2 to 6 carbon atoms.

The term "substituted alkenyl" refers to an alkenyl group as defined above having 1, 2, 3, 4 or 5 substituents (typically 1, 2, or 3 substituents), selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "alkynyl" refers to a monoradical of an unsaturated hydrocarbon, typically having from 2 to 20 carbon atoms (more typically from 2 to 10 carbon atoms, e.g. 2 to 6 carbon atoms) and having from 1 to 6 carbon-carbon triple bonds e.g. 1, 2, or 3 carbon-carbon triple bonds. Typical alkynyl groups include ethynyl (—C≡CH), propargyl (or propynyl, —C≡CCH3), and the like. In the event that alkynyl is attached to nitrogen, the triple bond cannot be alpha to the nitrogen.

The term "substituted alkynyl" refers to an alkynyl group as defined above having 1, 2, 3, 4 or 5 substituents (typically 1, 2, or 3 substituents), selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aminocarbonyl" refers to the group —C(O)NRR where each R is independently hydrogen, alkyl, cycloalkyl, aryl, heteroaryl, heterocyclyl or where both R groups are joined to form a heterocyclic group (e.g., morpholino). Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "ester" or "carboxyester" refers to the group —C(O)OR, where R is alkyl, cycloalkyl, aryl, heteroaryl, or heterocyclyl, which may be optionally further substituted by alkyl, alkoxy, halogen, CF$_3$, amino, substituted amino, cyano, or —S(O)$_n$Ra, in which Ra is alkyl, aryl, or heteroaryl and n is 0, 1 or 2.

The term "acylamino" refers to the group —NRC(O)R where each R is independently hydrogen, alkyl, aryl, heteroaryl, or heterocyclyl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2.

The term "acyloxy" refers to the groups —OC(O)-alkyl, —OC(O)-cycloalkyl, —OC(O)-aryl, —OC(O)-heteroaryl, and —OC(O)-heterocyclyl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aryl" refers to an aromatic carbocyclic group of 6 to 20 carbon atoms having a single ring (e.g., phenyl) or multiple rings (e.g., biphenyl), or multiple condensed (fused) rings (e.g., naphthyl, fluorenyl, and anthryl). Typical aryls include phenyl, fluorenyl, naphthyl, anthryl, and the like.

Unless otherwise constrained by the definition for the aryl substituent, such aryl groups can optionally be substituted with 1, 2, 3, 4 or 5 substituents (typically 1, 2, or 3 substituents), selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aryloxy" refers to the group aryl-O— wherein the aryl group is as defined above, and includes optionally substituted aryl groups as also defined above. The term "arylthio" refers to the group R—S—, where R is as defined for aryl.

The term "amino" refers to the group —NH$_2$.

The term "substituted amino" refers to the group —NRR where each R is independently selected from the group consisting of hydrogen, alkyl, cycloalkyl, aryl, heteroaryl and heterocyclyl provided that both R groups are not hydrogen, or a group —Y—Z, in which Y is optionally substituted alkylene and Z is alkenyl, cycloalkenyl, or alkynyl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "carboxyalkyl" refers to the groups —C(O)O-alkyl, —C(O)O-cycloalkyl, where alkyl and cycloalkyl are as defined herein, and may be optionally further substituted by alkyl, alkenyl, alkynyl, alkoxy, halogen, CF$_3$, amino, substituted amino, cyano, or —S(O)$_n$R, in which R is alkyl, aryl, or heteroaryl and n is 0, 1 or 2.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and bicyclo[2.2.1]heptane, or cyclic alkyl groups to which is fused an aryl group, for example indan, and the like.

The term "substituted cycloalkyl" refers to cycloalkyl groups having 1, 2, 3, 4 or 5 substituents (typically 1, 2, or 3 substituents), selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. The term "substituted cycloalkyl" also includes cycloalkyl groups wherein one or more of the annular carbon atoms of the cycloalkyl group is a carbonyl group (i.e. an oxygen atom is oxo to the ring). Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "halogen" or "halo" refers to fluoro, bromo, chloro, and iodo.

The term "haloalkyl" refers to alkyl of 1-6 carbon atoms substituted by 1, 2, 3, 4, 5, or 6 halo atoms.

The term "acyl" denotes a group —C(O)R, in which R is hydrogen, optionally substituted alkyl, optionally substituted cycloalkyl, optionally substituted heterocyclyl, optionally substituted aryl, and optionally substituted heteroaryl.

The term "heteroaryl" refers to a group comprising 1 to 15 carbon atoms and 1 to 4 heteroatoms selected from oxygen, nitrogen, and sulfur within at least one ring. The term "heteroaryl" is generic to the terms "aromatic heteroaryl" and "partially saturated heteroaryl". The term "aromatic heteroaryl" refers to a heteroaryl in which at least one ring is aromatic. Examples of aromatic heteroaryls include pyrrole, thiophene, pyridine, quinoline, pteridine. The term "partially saturated heteroaryl" refers to a heteroaryl having a structure equivalent to an underlying aromatic heteroaryl which has had one or more double bonds in an aromatic ring of the underlying aromatic heteroaryl saturated. Examples of partially saturated heteroaryls include dihydropyrrole, dihydropyridine, 1,2,3,4-tetrahydronaphthalene.

Unless otherwise constrained by the definition for the heteroaryl substituent, such heteroaryl groups can be optionally substituted with 1 to 5 substituents (typically 1, 2, or 3 substituents) selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl (an alkyl ester), arylthio, heteroaryl, heteroarylthio, heterocyclylthio, thiol, alkylthio, aryl, aryloxy, aralkyl, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2. Such heteroaryl groups can have a single ring (e.g., pyridyl or furyl) or multiple condensed rings (e.g., indolizinyl, benzothiazole, or benzothienyl). Examples of nitrogen heterocyclyls and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-alkoxy-nitrogen containing heteroaryl compounds.

The term "heteroaryloxy" refers to the group heteroaryl-O—.

The term "heterocyclyl" refers to a monoradical saturated group having a single ring or multiple condensed rings, having from 1 to 40 carbon atoms and from 1 to 10 hetero atoms, preferably 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5 substituents (typically 1, 2, or 3 substituents), selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2. Heterocyclic groups can have a single ring or multiple condensed rings. Preferred heterocyclics include tetrahydrofuranyl, morpholino, piperidinyl, and the like.

The term "thiol" refers to the group —SH.

The term "substituted alkylthio" refers to the group —S-substituted alkyl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, aryl, or heteroaryl. "Substituted sulfoxide" refers to a group —S(O)R, in which R is substituted alkyl, substituted aryl, or substituted heteroaryl, as defined herein.

The term "sulfone" refers to a group —$S(O)_2R$, in which R is alkyl, aryl, or heteroaryl. "Substituted sulfone" refers to a group —$S(O)_2R$, in which R is substituted alkyl, substituted aryl, or substituted heteroaryl, as defined herein.

The term "keto" refers to a group —C(O)—. The term "thiocarbonyl" refers to a group —C(S)—. The term "carboxy" refers to a group —C(O)—OH.

"Optional" or "optionally" means that the subsequently described event or circumstance may or may not occur, and that the description includes instances where said event or circumstance occurs and instances in which it does not.

A "substituted" group includes embodiments in which a monoradical substituent is bound to a single atom of the substituted group (e.g. forming a branch), and also includes embodiments in which the substituent may be a diradical bridging group bound to two adjacent atoms of the substituted group, thereby forming a fused ring on the substituted group.

A compound of a given Formula (e.g. the "compound of Formula (I)") is intended to encompass the compounds of the invention as disclosed, and the pharmaceutically acceptable salts, pharmaceutically acceptable esters, hydrates, polymorphs, and prodrugs of such compounds. Additionally, the compounds of the invention may possess one or more asymmetric centers, and can be produced as a racemic mixture or as individual enantiomers or diastereoisomers. The number of stereoisomers present in any given compound of a given Formula depends upon the number of asymmetric centers present (there are 2n stereoisomers possible where n is the number of asymmetric centers). The individual stereoisomers may be obtained by resolving a racemic or non-racemic mixture of an intermediate at some appropriate stage of the synthesis, or by resolution of the compound by conventional means. The individual stereoisomers (including individual enantiomers and diastereoisomers) as well as racemic and non-racemic mixtures of stereoisomers are encompassed within the scope of the present invention, all of which are intended to be depicted by the structures of this specification unless otherwise specifically indicated.

The invention also included compounds of Formula I in which from 1 to n hydrogens attached to a carbon atom is/are replaced by deuterium, in which n is the number of hydrogens in the molecule. Such compounds exhibit increased resistance to metabolism, and are thus useful for increasing the half life of any compound of Formula I when administered to a mammal. See, for example, Foster, "Deuterium Isotope Effects in Studies of Drug Metabolism", Trends Pharmacol. Sci. 5(12):524-527 (1984). Such compounds are synthesized by means well known in the art, for example by employing starting materials in which one or more hydrogens have been replaced by deuterium.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Cahn Ingold Prelog R S system. When the compound is a pure enantiomer the stereochemistry at each chiral carbon may be specified by either R or S. Resolved compounds whose absolute configuration is unknown are designated (+) or (−) depending on the direction (dextro- or laevorotary) that they rotate the plane of polarized light at the wavelength of the sodium D line.

The term "therapeutically effective amount" refers to an amount that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "treatment" or "treating" means any treatment of a disease in a mammal, including:
  (i) preventing the disease, that is, causing the clinical symptoms of the disease not to develop;
  (ii) inhibiting the disease, that is, arresting the development of clinical symptoms; and/or
  (iii) relieving the disease, that is, causing the regression of clinical symptoms.

In many cases, the compounds of this invention are capable of forming acid and/or base salts by virtue of the presence of amino and/or carboxyl groups or groups similar thereto.

The term "pharmaceutically acceptable salt" of a given compound refers to salts that retain the biological effectiveness and properties of the given compound, and which are not biologically or otherwise undesirable. Pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl)amines, tri(substituted alkyl)amines, alkenyl amines, dialkenyl amines, trialkenyl amines, substituted alkenyl amines, di(substituted alkenyl)amines, tri(substituted alkenyl)amines, cycloalkyl amines, di(cycloalkyl)amines, tri(cycloalkyl)amines, substituted cycloalkyl amines, disubstituted cycloalkyl amine, trisubstituted cycloalkyl amines, cycloalkenyl amines, di(cycloalkenyl)amines, tri(cycloalkenyl)amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Specific examples of suitable amines include, by way of example only, isopropylamine, trimethyl amine, diethyl amine, tri(iso-propyl)amine, tri(n-propyl)amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

"Coronary diseases" or "cardiovascular diseases" refer to diseases of the cardiovasculature arising from any one or more than one of, for example, heart failure (including congestive heart failure, diastolic heart failure and systolic heart failure), acute heart failure, ischemia, recurrent ischemia, myocardial infarction, arrhythmias, angina (including exercise-induced angina, variant angina, stable angina, unstable angina), acute coronary syndrome, diabetes, and intermittent claudication.

"Intermittent claudication" means the pain associated with peripheral artery disease. "Peripheral artery disease" or PAD is a type of occlusive peripheral vascular disease (PVD). PAD affects the arteries outside the heart and brain. The most common symptom of PAD is a painful cramping in the hips, thighs, or calves when walking, climbing stairs, or exercising. The pain is called intermittent claudication. When listing the symptom intermittent claudication, it is intended to include both PAD and PVD Arrhythmia refers to any abnormal heart rate. Bradycardia refers to abnormally slow heart rate whereas tachycardia refers to an abnormally rapid heart rate. As used herein, the treatment of arrhythmia is intended to include the treatment of supra ventricular tachycardias such as atrial fibrillation, atrial flutter, AV nodal reentrant tachycardia, atrial tachycardia, and the ventricular tachycardias (VTs), including idiopathic ventricular tachycardia, ventricular fibrillation, pre-excitation syndrome, and Torsade de Pointes (TdP), Where a given group (moiety) is described herein as being attached to a second group and the site of attachment is not explicit, the given group may be attached at any available site of the given group to any available site of the second group. For example, a "lower alkyl-substituted phenyl", where the attachment sites are not explicit, may have any available site of the lower alkyl group attached to any available site of the phenyl group. In this regard, an "available site" is a site of the group at which a hydrogen of the group may be replaced with a substituent.

Nomenclature

Names of compounds of the present invention are provided using ACD/Name software for naming chemical compounds (Advanced Chemistry Development, Inc., Toronto). Other compounds or radicals may be named with common names, or systematic or non-systematic names. The naming and numbering of the compounds of the invention is illustrated with a representative compound of Formula (I)

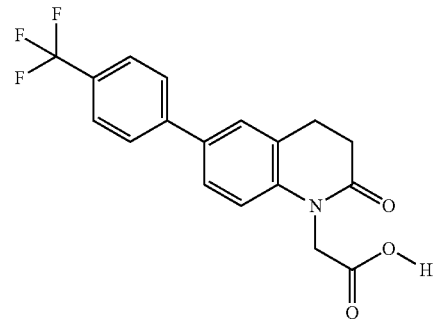 [SMILES: O=C(O)CN1C(=O)CCc2cc(-c3ccc(C(F)(F)F)cc3)ccc21]

which is named {2-oxo-6-[4-(trifluoromethyl)phenyl]-3,4-dihydroquinolin-1(2H)-yl}acetic acid.

Further Embodiments

In typical embodiments, the compounds provided by the present invention are effective in the treatment of conditions known to respond to administration of late sodium channel blockers, including cardiovascular diseases such as atrial and ventricular arrhythmias, Prinzmetal's (variant) angina, stable angina, unstable angina, ischemia and reperfusion injury in cardiac, kidney, liver and the brain, exercise induced angina, congestive heart disease, and myocardial infarction. In some embodiments, compounds provided by the present invention which function as late sodium channel blockers may be used in the treatment of diseases affecting the neuromuscular system resulting in pain, seizures, epilepsy, or paralysis, or in the treatment of diabetes and disease states related to diabetes, such as diabetic peripheral neuropathy. In some embodiments, compounds provided by the present invention which function as late sodium channel blockers may be used in the treatment of cerebrovascular disorders, such as stroke.

Certain compounds of the invention also possess sufficient activity in modulating neuronal sodium channels and may have appropriate pharmacokinetic properties such that they may active with regard to the central and/or peripheral nervous system. Consequently, some compounds of the invention may also be of use in the treatment of pain of neuropathic origin.

In typical embodiments, the present invention is intended to encompass the compounds disclosed herein, and the pharmaceutically acceptable salts, pharmaceutically acceptable esters, tautomeric forms, polymorphs, and prodrugs of such compounds. In some embodiments, the present invention includes a pharmaceutically acceptable addition salt, a pharmaceutically acceptable ester, a hydrate of an addition salt, a tautomeric form, a polymorph, an enantiomer, a mixture of enantiomers, a stereoisomer or mixture of stereoisomers (pure or as a racemic or non-racemic mixture) of a compound described herein, e.g. a compound of Formula (I); such as a compound of Formula (I) named herein.

Combination Therapy

Coronary patients being treated for an acute cardiovascular disease event by administration of late sodium channel blockers often exhibit diseases or conditions that benefit from treatment with other therapeutic agents. These diseases or conditions can be of the cardiovascular nature or can be related to pulmonary disorders, metabolic disorders, gastrointestinal disorders and the like. Additionally, some coronary patients being treated for an acute cardiovascular disease event by administration of late sodium channel blockers exhibit conditions that can benefit from treatment with therapeutic agents that are antibiotics, analgesics, and/or antidepressants and anti-anxiety agents.

Cardiovascular related diseases or conditions that can benefit from a combination treatment of late sodium channel blockers with other therapeutic agents include, without limitation, angina, including stable angina, unstable angina (UA), exercised-induced angina, variant angina, arrhythmias, intermittent claudication, myocardial infarction including non-STE myocardial infarction (NSTEMI), heart failure including congestive (or chronic) heart failure, acute heart failure, or recurrent ischemia.

Therapeutic agents suitable for treating cardiovascular related diseases or conditions include anti-anginals, heart failure agents, antithrombotic agents, antiarrhythmic agents, antihypertensive agents, and lipid lowering agents.

The co-administration of late sodium channel blockers with therapeutic agents suitable for treating cardiovascular related conditions allows enhancement in the standard of care therapy the patient is currently receiving.

Anti-anginals include beta-blockers, calcium channel blockers, and nitrates. Beta blockers reduce the heart's need for oxygen by reducing its workload resulting in a decreased heart rate and less vigorous heart contraction. Examples of beta-blockers include acebutolol (Sectral), atenolol (Tenormin), betaxolol (Kerlone), bisoprolol/hydrochlorothiazide (Ziac), bisoprolol (Zebeta), carteolol (Cartrol), esmolol (Brevibloc), labetalol (Normodyne, Trandate), metoprolol (Lopressor, Toprol XL), nadolol (Corgard), propranolol (Inderal), sotalol (Betapace), and timolol (Blocadren).

Nitrates dilate the arteries and veins thereby increasing coronary blood flow and decreasing blood pressure. Examples of nitrates include nitroglycerin, nitrate patches, isosorbide dinitrate, and isosorbide-5-mononitrate.

Calcium channel blockers prevent the normal flow of calcium into the cells of the heart and blood vessels causing the blood vessels to relax thereby increasing the supply of blood and oxygen to the heart. Examples of calcium channel blockers include amlodipine (Norvasc, Lotrel), bepridil (Vascor), diltiazem (Cardizem, Tiazac), felodipine (Plendil), nifedipine (Adalat, Procardia), nimodipine (Nimotop), nisoldipine (Sular), verapamil (Calan, Isoptin, Verelan), and nicardipine.

Agents used to treat heart failure include diuretics, ACE inhibitors, vasodilators, and cardiac glycosides. Diuretics eliminate excess fluids in the tissues and circulation thereby relieving many of the symptoms of heart failure. Examples of diuretics include hydrochlorothiazide, metolazone (Zaroxolyn), furosemide (Lasix), bumetanide (Bumex), spironolactone (Aldactone), and eplerenone (Inspra).

Angiotensin converting enzyme (ACE) inhibitors reduce the workload on the heart by expanding the blood vessels and decreasing resistance to blood flow. Examples of ACE inhibitors include benazepril (Lotensin), captopril (Capoten), enalapril (Vasotec), fosinopril (Monopril), lisinopril (Prinivil, Zestril), moexipril (Univasc), perindopril (Aceon), quinapril (Accupril), ramipril (Altace), and trandolapril (Mavik).

Vasodilators reduce pressure on the blood vessels by making them relax and expand. Examples of vasodilators include hydralazine, diazoxide, prazosin, clonidine, and methyldopa. ACE inhibitors, nitrates, potassium channel activators, and calcium channel blockers also act as vasodilators.

Cardiac glycosides are compounds that increase the force of the heart's contractions. These compounds strengthen the pumping capacity of the heart and improve irregular heartbeat activity. Examples of cardiac glycosides include digitalis, digoxin, and digitoxin.

Antithrombotics inhibit the clotting ability of the blood. There are three main types of antithrombotics—platelet inhibitors, anticoagulants, and thrombolytic agents.

Platelet inhibitors inhibit the clotting activity of platelets, thereby reducing clotting in the arteries. Examples of platelet inhibitors include acetylsalicylic acid (aspirin), ticlopidine, clopidogrel (plavix), dipyridamole, cilostazol, persantine sulfinpyrazone, dipyridamole, indomethacin, and glycoprotein llb/llla inhibitors, such as abciximab, tirofiban, and eptifibatide (Integrelin). Beta blockers and calcium channel blockers also have a platelet-inhibiting effect.

Anticoagulants prevent blood clots from growing larger and prevent the formation of new clots. Examples of anticoagulants include bivalirudin (Angiomax), warfarin (Coumadin), unfractionated heparin, low molecular weight heparin, danaparoid, lepirudin, and argatroban.

Thrombolytic agents act to break down an existing blood clot. Examples of thrombolytic agents include streptokinase, urokinase, and tenecteplase (TNK), and tissue plasminogen activator (t-PA).

Antiarrhythmic agents are used to treat disorders of the heart rate and rhythm. Examples of antiarrhythmic agents include amiodarone, quinidine, procainamide, lidocaine, and propafenone. Cardiac glycosides and beta blockers are also used as antiarrhythmic agents.

Antihypertensive agents are used to treat hypertension, a condition in which the blood pressure is consistently higher than normal. Hypertension is associated with many aspects of cardiovascular disease, including congestive heart failure, atherosclerosis, and clot formation. Examples of antihypertensive agents include alpha-1-adrenergic antagonists, such as prazosin (Minipress), doxazosin mesylate (Cardura), prazosin hydrochloride (Minipress), prazosin, polythiazide (Minizide), and terazosin hydrochloride (Hytrin); beta-adrenergic antagonists, such as propranolol (Inderal), nadolol (Corgard), timolol (Blocadren), metoprolol (Lopressor), and pindolol (Visken); central alpha-adrenoceptor agonists, such as clonidine hydrochloride (Catapres), clonidine hydrochloride and chlorthalidone (Clorpres, Combipres), guanabenz Acetate (Wytensin), guanfacine hydrochloride (Tenex), methyldopa (Aldomet), methyldopa and chlorothiazide (Aldoclor), methyldopa and hydrochlorothiazide (Aldoril); combined alpha/beta-adrenergic antagonists, such as labetalol (Normodyne, Trandate), Carvedilol (Coreg); adrenergic neuron blocking agents, such as guanethidine (Ismelin), reserpine (Serpasil); central nervous system-acting antihypertensives, such as clonidine (Catapres), methyldopa (Aldomet), guanabenz (Wytensin); anti-angiotensin II agents; ACE inhibitors, such as perindopril (Aceon) captopril (Capoten), enalapril (Vasotec), lisinopril (Prinivil, Zestril); angiotensin-II receptor antagonists, such as Candesartan (Atacand), Eprosartan (Teveten), Irbesartan (Avapro), Losartan (Cozaar), Telmisartan (Micardis), Valsartan (Diovan); calcium channel blockers, such as verapamil (Calan, Isoptin), diltiazem (Cardizem), nifedipine (Adalat, Procardia); diuretics; direct vasodilators, such as nitroprusside (Nipride), diazoxide (Hyperstat IV), hydralazine (Apresoline), minoxidil (Loniten), verapamil; and potassium channel activators, such as aprikalim, bimakalim, cromakalim, emakalim, nicorandil, and pinacidil.

Lipid lowering agents are used to lower the amounts of cholesterol or fatty sugars present in the blood. Examples of lipid lowering agents include bezafibrate (Bezalip), ciprofibrate (Modalim), and statins, such as atorvastatin (Lipitor), fluvastatin (Lescol), lovastatin (Mevacor, Altocor), mevastatin, pitavastatin (Livalo, Pitava) pravastatin (Lipostat), rosuvastatin (Crestor), and simvastatin (Zocor).

In this invention, the patient in need of the late sodium channel blocker often suffers from secondary medical conditions such as one or more of a metabolic disorder, a pulmonary disorder, a peripheral vascular disorder, or a gastrointestinal disorder. Such patients can benefit from treatment of a combination therapy comprising administering to the patient the compounds of the invention in combination with at least one therapeutic agent.

Pulmonary disorder refers to any disease or condition related to the lungs. Examples of pulmonary disorders include, without limitation, asthma, chronic obstructive pulmonary disease (COPD), bronchitis, and emphysema.

Examples of therapeutics agents used to treat pulmonary disorders include bronchodilators including beta2 agonists and anticholinergics, corticosteroids, and electrolyte supplements. Specific examples of therapeutic agents used to treat pulmonary disorders include epinephrine, terbutaline (Brethaire, Bricanyl), albuterol (Proventil), salmeterol (Serevent, Serevent Diskus), theophylline, ipratropium bromide (Atrovent), tiotropium (Spiriva), methylprednisolone (Solu-Medrol, Medrol), magnesium, and potassium.

Examples of metabolic disorders include, without limitation, diabetes, including type I and type II diabetes, metabolic syndrome, dyslipidemia, obesity, glucose intolerance, hypertension, elevated serum cholesterol, and elevated triglycerides.

Examples of therapeutic agents used to treat metabolic disorders include antihypertensive agents and lipid lowering agents, as described in the section "Cardiovascular Agent Combination Therapy" above. Additional therapeutic agents used to treat metabolic disorders include insulin, sulfonylureas, biguanides, alpha-glucosidase inhibitors, and incretin mimetics.

Peripheral vascular disorders are disorders related to the blood vessels (arteries and veins) located outside the heart and brain, including, for example peripheral arterial disease (PAD), a condition that develops when the arteries that supply blood to the internal organs, arms, and legs become completely or partially blocked as a result of atherosclerosis.

Gastrointestinal disorders refer to diseases and conditions associated with the gastrointestinal tract. Examples of gastrointestinal disorders include gastroesophageal reflux disease (GERD), inflammatory bowel disease (IBD), gastroenteritis, gastritis and peptic ulcer disease, and pancreatitis.

Examples of therapeutic agents used to treat gastrointestinal disorders include proton pump inhibitors, such as pantoprazole (Protonix), lansoprazole (Prevacid), esomeprazole (Nexium), omeprazole (Prilosec), rabeprazole; H2 blockers, such as cimetidine (Tagamet), ranitidine (Zantac), famotidine (Pepcid), nizatidine (Axid); prostaglandins, such as misoprostoL (Cytotec); sucralfate; and antacids.

Patients presenting with an acute coronary disease event may exhibit conditions that benefit from administration of therapeutic agent or agents that are antibiotics, analgesics, antidepressant and anti-anxiety agents in combination with ranolazine.

Antibiotics are therapeutic agents that kill, or stop the growth of, microorganisms, including both bacteria and fungi. Example of antibiotic agents include β-Lactam antibiotics, including penicillins (amoxicillin), cephalosporins, such as cefazolin, cefuroxime, cefadroxil (Duricef), cephalexin (Keflex), cephradine (Velosef), cefaclor (Ceclor), cefuroxime axtel (Ceftin), cefprozil (Cefzil), loracarbef (Lorabid), cefixime (Suprax), cefpodoxime proxetil (Vantin), ceftibuten (Cedax), cefdinir (Omnicef), ceftriaxone (Rocephin), carbapenems, and monobactams; tetracyclines, such as tetracycline; macrolide antibiotics, such as erythromycin; aminoglycosides, such as gentamicin, tobramycin, amikacin; quinolones such as ciprofloxacin; cyclic peptides, such as vancomycin, streptogramins, polymyxins; lincosamides, such as clindamycin; oxazolidinoes, such as linezolid; and sulfa antibiotics, such as sulfisoxazole.

Analgesics are therapeutic agents that are used to relieve pain. Examples of analgesics include opiates and morphinomimetics, such as fentanyl and morphine; paracetamol; NSAIDs, and COX-2 inhibitors.

Antidepressant and anti-anxiety agents include those agents used to treat anxiety disorders, depression, and those used as sedatives and tranquillers. Examples of antidepressant and anti-anxiety agents include benzodiazepines, such as diazepam, lorazepam, and midazolam; enzodiazepines; barbiturates; glutethimide; chloral hydrate; meprobamate; sertraline (Zoloft, Lustral, Apo-Sertral, Asentra, Gladem, Serlift, Stimuloton); escitalopram (Lexapro, Cipralex); fluoxetine (Prozac, Sarafem, Fluctin, Fontex, Prodep, Fludep, Lovan); venlafaxine (Effexor XR, Efexor); citalopram (Celexa, Cipramil, Talohexane); paroxetine (Paxil, Seroxat, Aropax); trazodone (Desyrel); amitriptyline (Elavil); and bupropion (Wellbutrin, Zyban).

Pharmaceutical Compositions and Administration

Compounds provided in accordance with the present invention are usually administered in the form of pharmaceutical compositions. This invention therefore provides pharmaceutical compositions that contain, as the active ingredient, one or more of the compounds described, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The pharmaceutical compositions may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.)

The pharmaceutical compositions may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parenteral, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound according to the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of compounds in accordance with the invention. Administration may be via capsule or enteric coated tablets, or the like. In making the pharmaceutical compositions that include at least one compound described herein, the active ingredient is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845, 770; 4,326,525; 4,902514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992, 445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds are generally administered in a pharmaceutically effective amount. Preferably, for oral administration, each dosage unit contains from 1 mg to 2 g of a compound described herein, and for parenteral administration, preferably from 0.1 to 700 mg of a compound a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably, the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

Synthesis of Compounds of Formula I

The compounds of the invention may be prepared using methods disclosed herein and routine modifications thereof which will be apparent given the disclosure herein and methods well known in the art. Conventional and well-known synthetic methods may be used in addition to the teachings herein. The synthesis of typical compounds described herein, e.g. compounds having structures described by one or more of Formula (I), may be accomplished as described in the following examples. If available, reagents may be purchased commercially, e.g. from Sigma Aldrich or other chemical suppliers.

General Syntheses:

Typical embodiments of compounds in accordance with the present invention may be synthesized using the general reaction schemes described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds which are embodiments of the present invention, inspection of the structure of the compound to be synthesized will provide the identity of each substituent group. The identity of the final product will generally render apparent the identity of the necessary starting materials by a simple process of inspection, given the examples herein.

Synthetic Reaction Parameters

The terms "solvent," "inert organic solvent" or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like). Unless specified to the contrary, the solvents used in the reactions of the present invention are inert organic solvents, and the reactions are carried out under an inert gas, preferably nitrogen.

The term "q.s." means adding a quantity sufficient to achieve a stated function, e.g., to bring a solution to the desired volume (i.e., 100%).

Synthesis of the Compounds of Formula (I)

The compounds of Formula (I) are typically prepared using as a starting material a commercially available starting material such as 3,4-dihydroxyquinolin-2(1H)-one substituted at the 6 or 7 position by bromo (compound of formula (1)). As shown in Reaction Schemes I and II below, the compound of formula (1) is then converted to a compound of Formula (I) in a two step process, attaching the desired $R^1$ and optionally substituted phenyl groups $R^4$ in any order.

REACTION SCHEME I

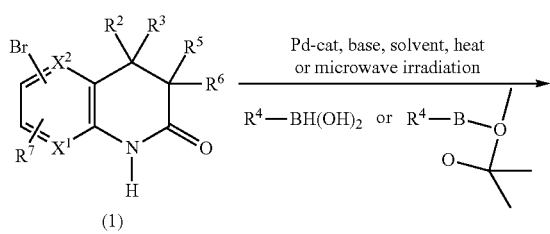

(1)

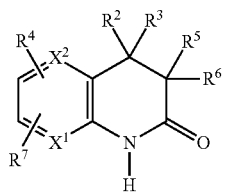

Formula (I) where $R^1$ is Hydrogen

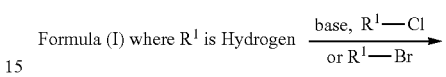

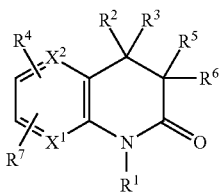

Formula (I) where $R^1$ is other than Hydrogen

Step 1—Preparation of a Compound of Formula (I) where $R^1$ is Hydrogen

Attachment of the optionally substituted phenyl group $R^4$ is typically carried out under conditions known as Suzuki coupling. The bromo compound of formula (1) is reacted with an appropriately substituted boronic acid derivative, for example with 4-trifluoromethoxyphenylboronic acid, in an aqueous solvent mixture, for example acetonitrile/aqueous sodium carbonate or another suitable solvent such as N,N-dimethylformamide. The reaction is typically conducted in the presence of a metal catalyst attached to an appropriate ligand, for example dichlorobis-(triphenylphosphine) palladium(II), at a temperature of about 150° C., under irradiation in a microwave, for about 10 minutes to about 1 hour. When the reaction is substantially complete, the product of Formula (I) where $R^1$ is hydrogen is isolated by conventional means, for example by partitioning the crude reaction mixture between ethyl acetate/aqueous sodium hydroxide, separating the organic layer, removing the solvent under reduced pressure, followed by chromatography of the residue, preferably preparatory TLC.

Step 2—Preparation of a Compound of Formula (I) where R is Other than Hydrogen

Attachment of the $R^1$ substituent is typically carried out by treating the compound of Formula (I) where $R^1$ is hydrogen with a base such as sodium hydride or potassium carbonate in a polar solvent such as N,N-dimethylformamide or tetrahydrofuran. A compound of formula $R_4X$, where X is halo, preferably chloro or bromo, is added at a temperature between 0° C. and 160° C., preferably at around 25° C., and the mixture maintained at that temperature for 1 to 40 hours. When the reaction is substantially complete, the product of Formula (I) where $R^1$ is other than hydrogen is isolated and purified by conventional means, for example by column chromatography purification or preparative HPLC separation.

REACTION SCHEME II

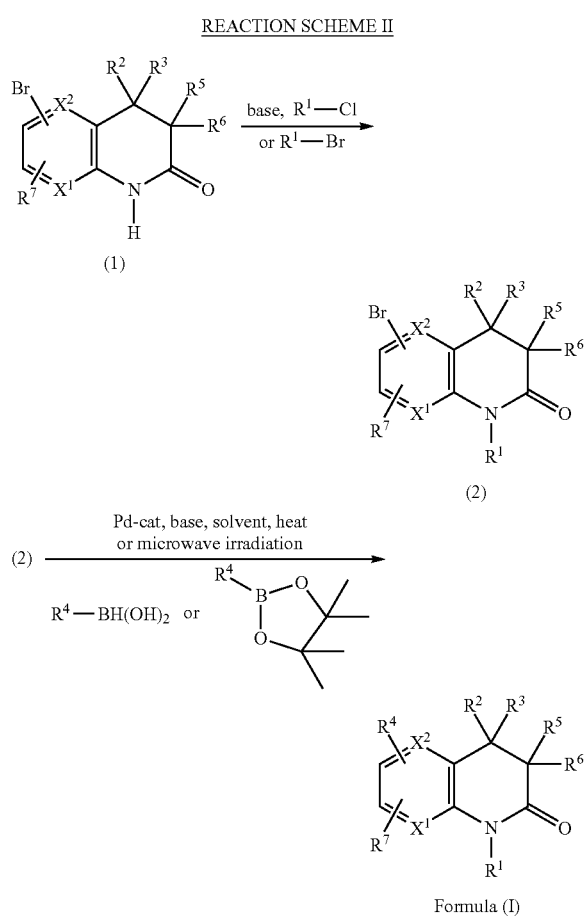

Step 1—Preparation of a Compound of Formula (2)

The compound of formula (1) is converted to a compound of formula (2) as described in Reaction Scheme I, Step 2 above.

Step 2—Preparation of a Compound of Formula (I) where $R^1$ is Other than Hydrogen The compound of formula (2) is converted to a compound of Formula (I) as described in Reaction Scheme I, Step 1 above.

Alternative Preparation—Secondary Modification of $R^1$

It will be appreciated that secondary modification may be made to the $R^1$ moiety after the compound of Formula (I) has been synthesized. This type of modification generally will involve the use of a protected terminal $R^1$ amino group. Once the protecting group is removed, the terminal $R^1$ amino group may be modified by reaction with any number of reactants allowing for the addition of a desired substituent.

In one type of secondary modification, the deprotected compound of Formula (I) is dissolved in the appropriate non-protic solvent, i.e., acetonitrile or the like, and then an acidic version of the desired substituents added to the reaction mixture, followed by 2-(1H-benzotriazol-1-yl)-1,1,3,3-tetramethyluronium tetrafluoroborate (TBTU) and diisopropylethylamine. After briefly heating to approximately 50° to 70° C., the reaction mixture is cooled to room temperature and the precipitated product filtered off and washed with additional solvent to provide a compound of Formula (I).

In another example of secondary modification, after the deprotected compound of Formula (I) is dissolved in the appropriate non-protic solvent, for example, acetonitrile, it is placed in a microwave vessel with methyl formate and heated at 135° C. to 150° C. for 15 to 30 minutes. Cooling and filtration provide the desired modified product of Formula (I)

In still another example of secondary modification, the deprotected compound of Formula (I) is dissolved in acetonitrile and dichloromethane. A base such as diisopropylethylamine is then added along with [1H]-pyrazole-1-hydroxamidine hydrochloride. The reaction is heated at 30° C. to 50° C. for 15 to 30 minutes. Cooling and filtration provides a modified compound of Formula (I).

Alternative Preparation —Synthesis Using Non-Brominated Precursor

The compounds of Formula (I) can also be prepared starting with commercially available starting materials such as 3,4-dihydroxyquinolin-2(1H)one, 3,4-dihydro-1,8-naphthyridin-2(1H)-one, 3,4-dihydro-1,7-naphthyridin-2(1H)-one, or 3,4-dihydro-1,5-naphthyridin-2(1H)-one. Such compounds are brominated using conventional techniques, to provide intermediates of formula I, which are then converted to a compound of Formula (I) s described above.

A typical synthesis using this technique is shown below.

REACTION SCHEME III

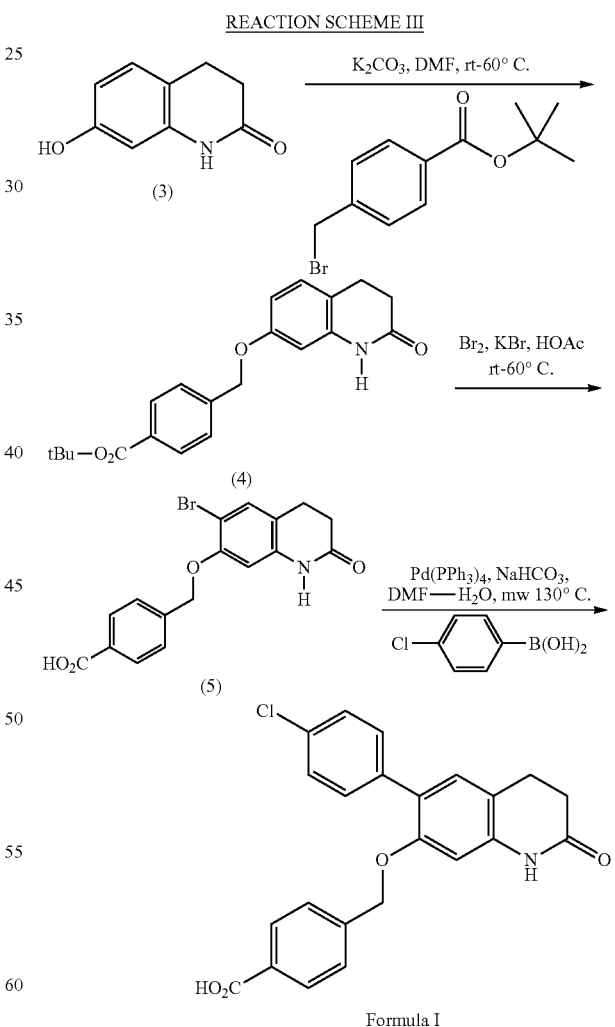

It will be appreciated that bromination may result in the production of a number of isomeric products any or all of which may be isolated and purified using conventional techniques.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

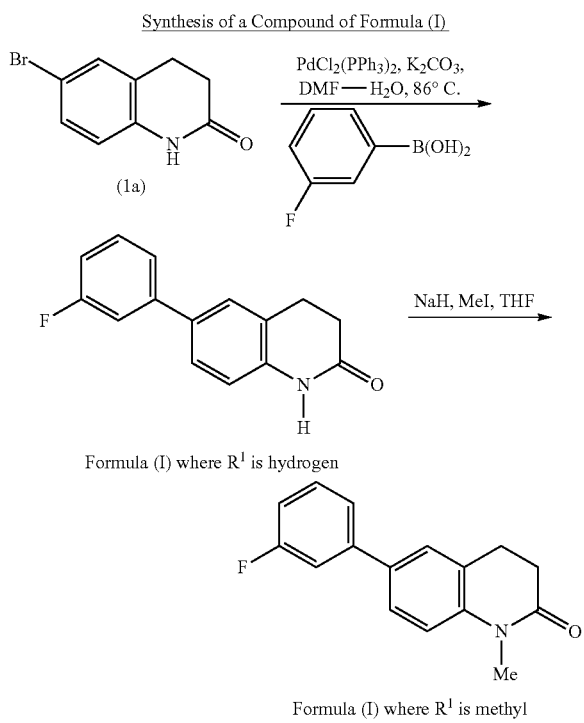

Synthesis of a Compound of Formula (I)

Formula (I) where $R^1$ is hydrogen

Formula (I) where $R^1$ is methyl

A. Synthesis of a Compound of Formula (I) in which $R^1$, $R^2$, $R^3$, $R^5$, and $R^6$ are Hydrogen, $R^4$ is 6-(3-Fluorophenyl), $R^7$ is Hydrogen, and $X^1$ and $X^2$ are both —CH=

To a solution of 6-bromo-3,4-dihydroquinolin-2(1H)-one (1a) (226 mg, 1.00 mmol) and 3-fluorophenylboronic acid (210 mg, 1.50 mmol) in N,N-dimethylformamide (10 mL) was added potassium carbonate (415 mg, 3.00 mmol) and water (2.0 mL). The reaction mixture was stirred for 5 minutes under an atmosphere of dry $N_2$, and $PdCl_2(PPh_3)_2$ (35 mg, 0.05 mmol) was added. The resulting mixture was heated at 86° C. for 5 hours, cooled, diluted with ethyl acetate (20 mL), filtered through a layer of celite which was washed with ethyl acetate (60 mL), the filtrate transferred to a separation funnel, and washed with 2 N potassium carbonate (20 mL), followed by 30% ammonium chloride (40 mL), then brine (50 mL). The solvent was removed from the organic layer under reduced pressure, to provide a pale yellow solid. To this crude product was added methanol (2 mL), the mixture sonicated, filtered, washed with cold methanol (3.0 mL), and dried under reduced pressure, to afford 6-(3-fluorophenyl)-3,4-dihydroquinolin-2(1H)-one, the compound of Formula (I) in which $R^1$ is hydrogen, as a white solid; MS m/z 242.1 (M+H), anal HPLC >97% in purity. $^1$H NMR (400 MHz; dmso-D6) δ 10.21 (s, 1H); 7.58 (d, J=2.1 Hz, 1H); 7.42-7.55 (m, 4H); 7.15 (m, 1H); 6.96 (d, J=8.2 Hz, 1H); 3.42 (t, J=7.6 Hz, 2H); 2.97 (t, J=7.6 Hz, 2H).

B. Synthesis of Additional Compounds of Formula (I) in which $R^1$ is Hydrogen

Similarly, following the procedure of Example 1A, but optionally replacing 3-fluorophenyl-boronic acid with other optionally substituted aryl boronic acids, or optionally replacing the conventional heating with microwave heating, the following compounds of Formula (I) in which $R^1$ is hydrogen were prepared:

1  6-(3-fluorophenyl)-3,4-dihydroquinolin-2(1H)-one
2  4-(2-oxo-1,2,3,4-tetrahydroquinolin-6-yl)benzamide
3  6-(4-fluorophenyl)-3,4-dihydroquinolin-2(1H)-one
4  6-phenyl-3,4-dihydroquinolin-2(1H)-one
5  4-(2-oxo-1,2,3,4-tetrahydroquinolin-6-yl)benzonitrile
6  3-(2-oxo-1,2,3,4-tetrahydroquinolin-6-yl)benzamide
7  6-(2-fluorophenyl)-3,4-dihydroquinolin-2(1H)-one
8  6-(3-acetylphenyl)-3,4-dihydroquinolin-2(1H)-one
9  6-[4-(trifluoromethyl)phenyl]-3,4-dihydroquinolin-2(1H)-one
10  6-[4-chloro-3-(trifluoromethyl)phenyl]-3,4-dihydroquinolin-2(1H)-one
11  6-(2,4-difluorophenyl)-3,4-dihydroquinolin-2(1H)-one
12  2-fluoro-5-(2-oxo-1,2,3,4-tetrahydroquinolin-6-yl)benzonitrile
13  6-[3-(trifluoromethyl)phenyl]-3,4-dihydroquinolin-2(1H)-one
14  1-(2-hydroxyethyl)-6-[4-(trifluoromethyl)phenyl]-3,4-dihydroquinolin-2(1H)-one
15  6-(3,4-difluorophenyl)-1-(2-hydroxyethyl)-3,4-dihydroquinolin-2(1H)-one
16  6-(2,4-difluorophenyl)-1-(2-hydroxyethyl)-3,4-dihydroquinolin-2(1H)-one
17  6-[4-(trifluoromethoxy)phenyl]-3,4-dihydroquinolin-2(1H)-one
18  6-(4-chlorophenyl)-3,4-dihydroquinolin-2(1H)-one
19  6-(3-fluoro-4-(trifluoromethyl)phenyl)-3,4-dihydroquinolin-2(1H)-one
20  6-(4-chlorophenyl)-3,4-dihydro-1,8-naphthyridin-2(1H)-one C. Synthesis of Additional Compounds of Formula (I) in which R is Hydrogen Similarly, following the above procedure, but optionally replacing 3-fluorophenyl-boronic acid with other optionally substituted aryl boronic acids, or optionally replacing the conventional heating with microwave heating, other compounds of Formula (I) in which $R^1$ is hydrogen are prepared:

D. Synthesis of a Compound of Formula (I) in which $R^1$ is Methyl, $R^2$, $R^3$, $R^5$, and $R^6$ are Hydrogen, $R^4$ is 6-(3-Fluorophenyl), $R^7$ is Hydrogen, and $X^1$ and $X^2$ are both —CH=

To a cooled (0° C.) solution of 6-(3-fluorophenyl)-3,4-dihydroquinolin-2(1H)-one (48 mg, 0.20 mmol) in anhydrous tetrahydrofuran (2 mL) was added 95% sodium hydride (10 mg, 0.40 mmol). The reaction mixture was stirred for 5 minutes, then warmed to 40° C. for 15 minutes under an atmosphere of dry $N_2$. Iodomethane (142 mg, 1.00 mmol) was added, and the resulting mixture was stirred at room temperature for 15 hours. Methanol (2 mL) was added, and the mixture stirred for 10 minutes. Solvent was removed from the reaction mixture under reduced pressure, ethyl acetate (30 mL) and 30% ammonium chloride (10 mL) were added, the organic phase was washed with water (10 mL), 30% ammonium chloride (15 mL) and brine (15 mL), and the organic layer was concentrated under reduced pressure to give 6-(3-fluorophenyl)-1-methyl-3,4-dihydroquinolin-2(1H)-one. MS m/z 256.1 (M+H), anal HPLC 92% in purity. $^1$H NMR (400 MHz; $CDCl_3$) δ 7.46 (dd, J=8.6 Hz, 2.3 Hz, 1H); 7.30-7.42 (m, 3H); 7.25 (m, 1H); 6.98-7.10 (m, 2H); 3.39 (s, 3H); 2.97 (t, J=7.4 Hz, 2H); 2.70 (t, J=7.4 Hz, 2H).

E. Synthesis of Additional Compounds of Formula (I) in which R¹ is Other then Hydrogen Similarly, following the procedure of Example 1D, but optionally replacing iodomethane with other optionally substituted alkyl halides, and optionally replacing sodium hydride with other bases such as potassium carbonate or caesium carbonate, and optionally replacing the reaction condition of room temperature with conventional or microwave heating, the following compounds of Formula (I) in which R¹ is other than hydrogen were prepared:

21  6-(3-fluorophenyl)-1-methyl-3,4-dihydroquinolin-2(1H)-one
22  ethyl [6-(2,4-difluorophenyl)-2-oxo-3,4-dihydroquinolin-1(2H)-yl]acetate
23  ethyl [6-(3,4-difluorophenyl)-2-oxo-3,4-dihydroquinolin-1(2H)-yl]acetate
24  ethyl {2-oxo-6-[3-(trifluoromethoxy)phenyl]-3,4-dihydroquinolin-1(2H)-yl}acetate
25  ethyl {2-oxo-6-[4-(trifluoromethoxy)phenyl]-3,4-dihydroquinolin-1(2H)-yl}acetate
26  1-{[2-(4-chlorophenyl)-1,3-thiazol-4-yl]methyl}-6-(2,4-difluorophenyl)-3,4-dihydroquinolin-2(1H)-one
27  6-(2,4-difluorophenyl)-1-(2-methoxyethyl)-3,4-dihydroquinolin-2(1H)-one
28  6-(2,4-difluorophenyl)-1-(2,2,2-trifluoroethyl)-3,4-dihydroquinolin-2(1H)-one
29  tert-butyl {2-oxo-6-[4-(trifluoromethyl)phenyl]-3,4-dihydroquinolin-1(2H)-yl}acetate
30  tert-butyl [6-(2,4-difluorophenyl)-2-oxo-3,4-dihydroquinolin-1(2H)-yl]acetate
31  2-{2-oxo-6-[4-(trifluoromethoxy)phenyl]-3,4-dihydroquinolin-1(2H)-yl}acetamide
32  1-[2-(morpholin-4-yl)-2-oxoethyl]-6-[4-(trifluoromethyl)phenyl]-3,4-dihydroquinolin-2(1H)-one
33  tert-butyl [6-(4-fluorophenyl)-2-oxo-3,4-dihydroquinolin-1(2H)-yl]acetate
34  6-[4-(trifluoromethoxy)phenyl]-3,4-dihydroquinolin-2(1H)-one
35  1-[(5-tert-butyl-1,2,4-oxadiazol-3-yl)methyl]-6-(4-fluorophenyl)-3,4-dihydroquinolin-2(1H)-one
36  6-(4-chlorophenyl)-3,4-dihydroquinolin-2(1H)-one
37  1-(pyridin-3-ylmethyl)-6-[4-(trifluoromethoxy)phenyl]-3,4-dihydroquinolin-2(1H)-one
38  6-(4-phenoxyphenyl)-3,4-dihydroquinolin-2(1H)-one
39  1-[(5-methylisoxazol-3-yl)methyl]-6-[4-(trifluoromethoxy)phenyl]-3,4-dihydroquinolin-2(1H)-one
40  tert-butyl [6-(4-chlorophenyl)-2-oxo-3,4-dihydroquinolin-1(2H)-yl]acetate
41  3-(2-oxo-1,2,3,4-tetrahydroquinolin-6-yl)benzonitrile
42  4,4-dimethyl-6-[4-(trifluoromethyl)phenyl]-3,4-dihydroquinolin-2(1H)-one
43  6-[3-(morpholin-4-ylcarbonyl)phenyl]-3,4-dihydroquinolin-2(1H)-one

F. Synthesis of Additional Compounds of Formula (I) in which R¹ is Other than Hydrogen Similarly, following the procedure of Example 1D, but optionally replacing iodomethane with other optionally substituted alkyl halides, and optionally replacing sodium hydride with other bases such as potassium carbonate or caesium carbonate, and optionally replacing the reaction condition of room temperature with conventional or microwave heating, other compounds of Formula (I) are prepared:

EXAMPLE 2

Synthesis of a Compound of Formula (I)

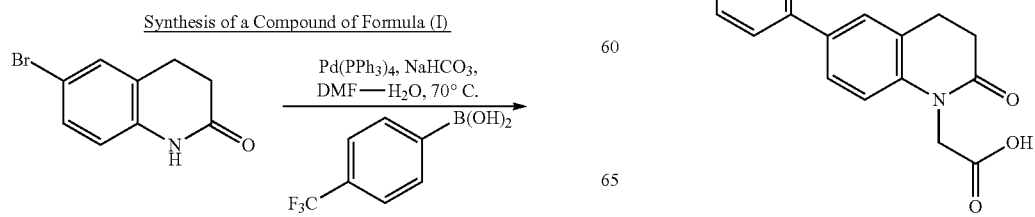

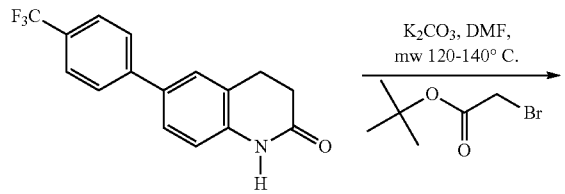

-continued

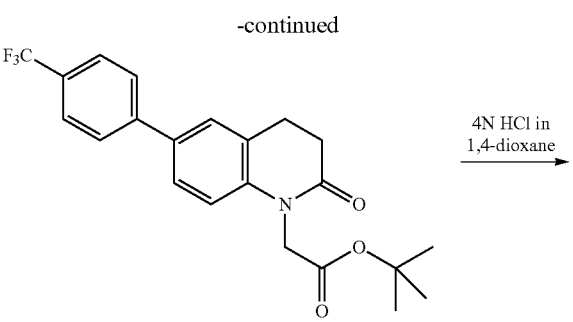

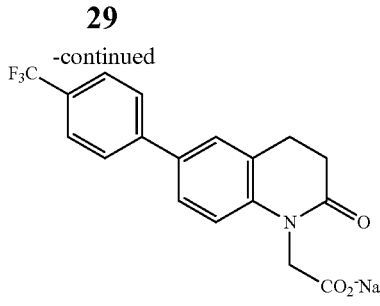

A. Synthesis of a Compound of Formula (I) in which $R^1$, $R^2$, $R^3$, $R^5$, and $R^6$ are Hydrogen, $R^4$ is 6-(4-Trifluoromethyl)phenyl), $R^7$ is Hydrogen, and $X^1$ and $X^2$ are both —CH=

To a solution of 6-bromo-3,4-dihydroquinolin-2(1H)-one (2.260 g, 10.00 mmol) and 4-(trifluoromethyl)phenyl boronic acid (2.850 g, 15.00 mmol) in N,N-dimethylformamide (50 mL) was added sodium bicarbonate (3.360 g, 40.00 mmol) and water (5 mL). The reaction mixture was stirred for 5 minutes under an atmosphere of dry $N_2$, then $Pd(PPh_3)_4$ (579 mg, 0.50 mmol) was added, and the resulting mixture was heated at 70° C. until the starting material (6-bromo-3,4-dihydroquinolin-2(1H)-one) was no longer seen by TLC. The mixture was cooled, diluted with ethyl acetate (50 mL), filtered through a layer of celite, which was washed with 10% N,N-dimethylformamide in ethyl acetate (100 mL), and the filtrate transferred to a separation funnel. The organic phase was washed with 1N sodium carbonate (100 mL), 30% ammonium chloride (100 mL), and brine (100 mL). Solvent was removed under reduced pressure to provide a yellow solid. Methanol (5.0 mL) was added, and the mixture sonicated, filtered, washed with methanol (5.0 mL), and dried under reduced pressure to afford 6-(4-(trifluoromethyl)phenyl)-3,4-dihydroquinolin-2(1H)-one (2.184 g, 7.5 mmol, 75%). LCMS mz 292.0 (M+H), anal HPLC ca 94% in purity, $^1$H NMR (400 MHz; CDCl$_3$) δ 7.98 (s, 1H); 7.66 (m, 4H); 7.40-7.50 (m, 2H); 6.86 (d, J=9.0 Hz, 1H); 3.06 (t, J=7.6 Hz, 2H); 2.70 (t, J=7.6 Hz, 2H).

B. Synthesis of a Compound of Formula (I) in which $R^1$ is t-Butoxycarbonylmethyl, $R^2$, $R^3$, $R^5$, and $R^6$ are Hydrogen, $R^4$ is 6-(4-(Trifluoromethyl)phenyl), $R^7$ is Hydrogen, and $X^1$ and $X^2$ are both —CH=

To a solution of 6-(4-(trifluoromethyl)phenyl)-3,4-dihydroquinolin-2(1H)-one (291 mg, 1.0 mmol) in anhydrous N,N-dimethylformamide (2.5 ml) was added potassium carbonate (276 mg, 2.0 mmol), and the mixture stirred at room temperature for 5 minutes in a 5 ml Personal Chemistry microwave reaction vial. To the above mixture was added tert-butyl 2-bromoacetate (390 mg, 2.0 mmol), the vial was sealed, and subjected to microwave irradiation at 120° C. for 5 min, and then at 140° C. for 40 min until most of the 6-(4-(trifluoromethyl)phenyl)-3,4-dihydroquinolin-2(1H)-one was converted. The reaction mixture was cooled, poured into water (40 mL), extracted with ethyl acetate (2×40 mL), the combined organic phase was washed with water (40 mL), 2N sodium carbonate (10 mL), brine (40 mL), dried over sodium sulfate, and the solvent was removed under reduced pressure. The crude product was dissolved in a mixture of N,N-dimethylformamide-methanol (1 and 2 mL respectively), subjected to reverse phase HPLC with a gradient of acetonitrile/water (2% to 98%) to afford tert-butyl 2-(2-oxo-6-(4-(trifluoromethyl)phenyl)-3,4-dihydroquinolin-1(2H)-yl) acetate (247 mg, 0.61 mmol, 61%). LCMS mz 350.0 (M-56+H), 428.0 (M+Na), anal HPLC >98% in purity, $^1$H NMR (400 MHz; CDCl$_3$) δ 7.67 (m, 4H); 7.40-7.50 (m, 2H); 6.86 (d, J=8.6 Hz, 1H); 4.63 (s, 2H); 3.04 (t, J=7.4 Hz, 2H); 2.76 (t, J=7.4 Hz, 2H), 1.48 (s, 9H).

C. Synthesis of a Compound of Formula (I) in which $R^1$ is —CH$_7$COOH, $R^2$, $R^3$, $R^5$, and $R^6$ are Hydrogen, $R^4$ is 6-(4-(Trifluoromethyl)phenyl), $R^7$ is Hydrogen, and $X^1$ and $X^2$ are both —CH=

To tert-butyl 2-(2-oxo-6-(4-(trifluoromethyl)phenyl)-3,4-dihydroquinolin-1(2H)-yl)acetate (202 mg, 0.50 mmol) in a 50 mL round-bottom flask was added 4N hydrochloric acid in 1,4-dioxane (6.0 mL, 24.0 mmol). The reaction mixture was stirred at room temperature for 4 hours, and the solvent removed under reduced pressure. A second portion of 4N HCl in 1,4-dioxane (6.0 mL, 24.0 mmol) was added with stirring for another 13 hours, and again the solvent was removed under reduced pressure, to afford 2-(2-oxo-6-(4-(trifluoromethyl)phenyl)-3,4-dihydroquinolin-1(2H)-yl)acetic acid as a solid (162 mg, 0.46 mmol, 92%). LCMS mz 350.0 (M+H), 372.0 (M+Na), anal HPLC >97% in purity, $^1$H NMR (400 MHz; CDCl$_3$) δ 7.67 (m, 4H); 7.40-7.50 (m, 2H); 6.92 (d, J=8.6 Hz, 1H); 4.76 (s, 2H); 3.04 (m, 2H); 2.79 (m, 2H), 1.48 (s, 9H).

D. Synthesis of a Sodium Salt of Formula (I)

To a solution of 2-(2-oxo-6-(4-(trifluoromethyl)phenyl)-3,4-dihydroquinolin-1(2H)-yl)acetic acid (34.9 mg, 0.10 mmol) in tetrahydrofuran (1 mL) was added sodium bicarbonate (8.4 mg, 0.10 mmol) and water (2 mL). The reaction mixture was stirred at room temperature for 1 hour then freeze dried, to give sodium 2-(2-oxo-6-(4-(trifluoromethyl)phenyl)-3,4-dihydroquinolin-1(2H)-yl)acetate.

E. Synthesis of Additional Compounds of Formula (I)

Similarly, following the above procedures of Example 2, but optionally replacing 4-(trifluoromethyl)phenyl boronic acid with other optionally substituted aryl boronic acids, or optionally replacing the conventional heating with microwave heating, the following compounds of Formula (I) were prepared:

44 {2-oxo-6-[4-(trifluoromethyl)phenyl]-3,4-dihydroquinolin-1(2H)-yl}acetic acid
45 tert-butyl {2-oxo-6-[4-(trifluoromethyl)phenyl]-3,4-dihydroquinolin-1(2H)-yl}acetate
46 tert-butyl [6-(2,4-difluorophenyl)-2-oxo-3,4-dihydroquinolin-1(2H)-yl]acetate
47 tert-butyl [6-(4-fluorophenyl)-2-oxo-3,4-dihydroquinolin-1(2H)-yl]acetate
48 [6-(4-fluorophenyl)-2-oxo-3,4-dihydroquinolin-1(2H)-yl]acetic acid
49 1-(2-methoxyethyl)-6-[4-(trifluoromethyl)phenyl]-3,4-dihydroquinolin-2(1H)-one
50 tert-butyl {2-oxo-6-[4-(trifluoromethoxy)phenyl]-3,4-dihydroquinolin-1(2H)-yl}acetate
51 {2-oxo-6-[4-(trifluoromethoxy)phenyl]-3,4-dihydroquinolin-1(2H)-yl}acetic acid
52 sodium {2-oxo-6-[4-(trifluoromethyl)phenyl]-3,4-dihydroquinolin-1(2H)-yl}acetate
53 tert-butyl [6-(3-chlorophenyl)-2-oxo-3,4-dihydroquinolin-1(2H)-yl]acetate
54 ethyl {2-oxo-6-[4-(trifluoromethyl)phenyl]-3,4-dihydroquinolin-1(2H)-yl}acetate -continued 55 2-[6-(2,4-difluorophenyl)-2-oxo-3,4-dihydroquinolin-1(2H)-yl]acetamide
56 2-{2-oxo-6-[4-(trifluoromethyl)phenyl]-3,4-dihydroquinolin-1(2H)-yl}acetamide
57 2-{6-[4-chloro-3-(trifluoromethyl)phenyl]-2-oxo-3,4-dihydroquinolin-1(2H)-yl}acetamide
58 [6-(4-chloro-3-fluorophenyl)-2-oxo-3,4-dihydroquinolin-1(2H)-yl]acetic acid
59 [6-(3-fluorophenyl)-2-oxo-3,4-dihydroquinolin-1(2H)-yl]acetic acid F. Synthesis of Additional Compounds of Formula (I)

Similarly, following the above procedures of Example 2, but optionally replacing 4-(trifluoromethyl)phenyl boronic acid with other optionally substituted aryl boronic acids, or optionally replacing the conventional heating with microwave heating, other compounds of Formula (I) are prepared:

EXAMPLE 3

Alternative Synthesis of a Compound of Formula (I)

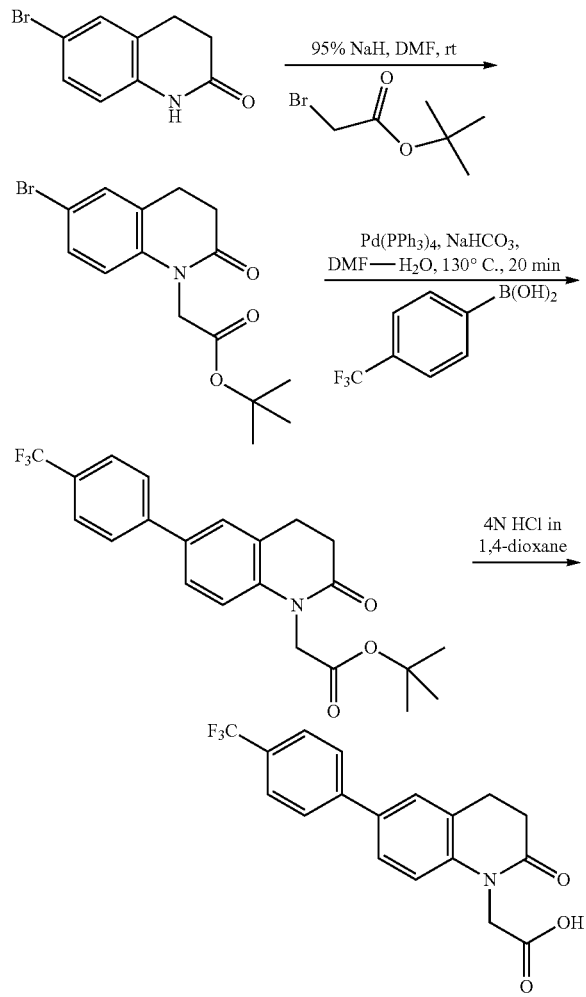

A. Synthesis of tert-butyl 2-(6-bromo-2-oxo-3,4-dihydroquinolin-1(2H)-yl)acetate To a mixture of 95% dry sodium hydride (834 mg, 33.0 mmol) in anhydrous N,N-dimethylformamide (30 mL) at room temperature was added a solution of 6-bromo-3,4-dihydroquinolin-2(1H)-one (6.780 g, 30.00 mmol) in anhydrous N,N-dimethylformamide (10 mL). The reaction mixture was stirred for 30 minutes under an atmosphere of dry $N_2$, followed by addition of a solution of tert-butyl 2-bromoacetate (7.5 mL, 49.7 mmol) in N,N-dimethylformamide (10 mL). The reaction mixture was stirred at room temperature until the majority of the starting material was converted (confirmed by LCMS). The reaction mixture was quenched with methanol (40 mL), the mixture concentrated under reduced pressure, then diluted with ethyl acetate (150 mL). The organic phase was washed with water (100 mL), 30% ammonium chloride (100 mL) and brine (100 mL), dried, and concentrated under reduced pressure. Ethyl ether (20 mL) was added, and the mixture sonicated, filtered, washed with ether (20 mL), and dried to afford tert-butyl 2-(6-bromo-2-oxo-3,4-dihydroquinolin-1(2H)-yl)acetate (7.348 g, 21.6 mmol, 72%). LCMS mz 285.9 (M-56+H), 363.9 (M+Na), anal HPLC >97% in purity. $^1$H NMR (400 MHz; CDCl$_3$) δ 7.30-7.40 (m, 2H); 7.50-6.70 (m, 1H); 4.54 (s, 2H); 2.92 (m, 2H); 2.69 (m, 2H), 1.44 (s, 9H).

B. Synthesis of a Compound of Formula (I) in which $R^1$ is t-Butoxycarbonylmethyl, $R^2$, $R^3$, $R^5$, and $R^6$ are Hydrogen, $R^4$ is 6-(4-(Trifluoromethyl)phenyl), $R^7$ is Hydrogen, and $X^1$ and $X^2$ are both —CH=

To a solution of tert-butyl 2-(6-bromo-2-oxo-3,4-dihydroquinolin-1(2H)-yl)acetate (680 mg, 2.0 mmol) and 4-(trifluoromethyl)phenyl boronic acid (456 mg, 2.4 mmol) in N,N-dimethylformamide (3 mL) in a Biotage microwave vial was added sodium bicarbonate (605 mg, 7.2 mmol) and water (0.55 mL). The reaction mixture was stirred for 5 minutes under an atmosphere of dry $N_2$, then PdCl$_2$(PPh$_3$)$_2$ (59 mg, 0.05 mmol) was added, and the resulting mixture sealed, subjected to microwave irradiation at 130° C. for 20 minutes. The mixture was then cooled, diluted with ethyl acetate (10 mL), filtered through celite, washed with 10% N,N-dimethylformamide in ethyl acetate (80 mL), and transferred to a separation funnel. The organic phase was washed with 1N sodium carbonate (40 mL), 30% ammonium chloride (40 mL) and brine (40 mL), dried and concentrated under reduced pressure. The crude product was purified by preparative HPLC with a gradient acetonitrile/water (5-98%) to afford tert-butyl 2-(6-bromo-2-oxo-3,4-dihydroquinolin-1(2H)-yl) acetate (535 mg, 1.32 mmol, 66%). LCMS mz 349.9 (M-56+H), 427.9 (M+Na), anal HPLC >97% in purity, $^1$H NMR (400 MHz; CDCl$_3$) δ 7.67 (m, 4H); 7.40-7.50 (m, 2H); 6.86 (d, J=8.6 Hz, 1H); 4.63 (s, 2H); 3.04 (t, J=7.4 Hz, 2H); 2.76 (t, J=7.4 Hz, 2H), 1.47 (s, 9H).

C. Synthesis of a Compound of Formula (I) in which $R^1$ is —CH$_2$COOH, $R^2$, $R^3$, $R^5$, and $R^6$ are Hydrogen, $R^4$ is 6-(4-(Trifluoromethyl)phenyl), $R^7$ is Hydrogen, and $X^1$ and $X^2$ are both —CH=

Hydrolysis of the tort butyl protecting group was carried out using the method described in Example 2C above, to obtain 2-(2-oxo-6-(4-(trifluoromethyl)phenyl)-3,4-dihydroquinolin-1(2H)-yl)acetic acid.

D. Synthesis of Additional Compounds of Formula (I)

Similarly, following the above procedures of Example 3A and 3B, but optionally replacing 4-(trifluoromethyl)phenyl boronic acid with other optionally substituted aryl boronic acids, or optionally replacing the conventional heating with microwave heating, the following compounds of Formula (I) were prepared:

60 2-(2-oxo-6-(3-(trifluoromethyl)phenyl)-3,4-dihydroquinolin-1(2H)-yl)acetic acid
62 tert-butyl {2-oxo-6-[4-(trifluoromethoxy)phenyl]-3,4-dihydroquinolin-1(2H)-yl}acetate
63 {2-oxo-6-[4-(trifluoromethoxy)phenyl]-3,4-dihydroquinolin-1(2H)-yl}acetic acid
64 tert-butyl [6-(3-chlorophenyl)-2-oxo-3,4-dihydroquinolin-1(2H)-yl]acetate
65 tert-butyl [6-(4-chlorophenyl)-2-oxo-3,4-dihydroquinolin-1(2H)-yl]acetate
66 tert-butyl [2-oxo-6-(4-phenoxyphenyl)-3,4-dihydroquinolin-1(2H)-yl]acetate
67 tert-butyl {6-[4-chloro-3-(trifluoromethyl)phenyl]-2-oxo-3,4-dihydroquinolin-1(2H)-yl}acetate
68 [6-(4-chlorophenyl)-2-oxo-3,4-dihydroquinolin-1(2H)-yl]acetic acid
69 [6-(3,4-dichlorophenyl)-2-oxo-3,4-dihydroquinolin-1(2H)-yl]acetic acid
70 [2-oxo-6-(4-phenoxyphenyl)-3,4-dihydroquinolin-1(2H)-yl]acetic acid
71 2-(6-(4-chloro-3-fluorophenyl)-2-oxo-3,4-dihydroquinolin-1(2H)-yl)acetic acid
72 {4,4-dimethyl-2-oxo-6-[4-(trifluoromethyl)phenyl]-3,4-dihydroquinolin-1(2H)-yl}acetic acid
73 [6-(3-chloro-4-fluorophenyl)-2-oxo-3,4-dihydroquinolin-1(2H)-yl]acetic acid
74 2-(6-(3-fluoro-4-(trifluoromethyl)phenyl)-2-oxo-3,4-dihydroquinolin-1(2H)-yl)acetic acid
75 tert-butyl 2-(6-(3-fluoro-4-(trifluoromethyl)phenyl)-2-oxo-3,4-dihydroquinolin-1(2H)-yl)acetate
76 tert-butyl 2-(6-(3,4-dichlorophenyl)-2-oxo-3,4-dihydroquinolin-1(2H)-yl)acetate
A 2-(2-oxo-6-(4-(trifluoromethoxy)phenyl)-3,4-dihydroquinolin-1(2H)-yl)acetic acid
B {7-methoxy-2-oxo-6-[4-(trifluoromethyl)phenyl]-3,4-dihydroquinolin-1(2H)-yl}acetic acid
C [6-(4-chlorophenyl)-7-methoxy-2-oxo-3,4-dihydroquinolin-1(2H)-yl]acetic acid

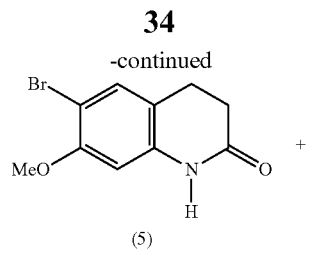

(5)

E. Synthesis of Additional Compounds of Formula (I)

Similarly, following the above procedures of Example 3A and 3B, but optionally replacing 4-(trifluoromethyl)phenyl boronic acid with other optionally substituted aryl boronic acids, or optionally replacing the conventional heating with microwave heating, other compounds of Formula (I) are prepared:

EXAMPLE 4

Alternative Synthesis of a Compound of Formula (I)

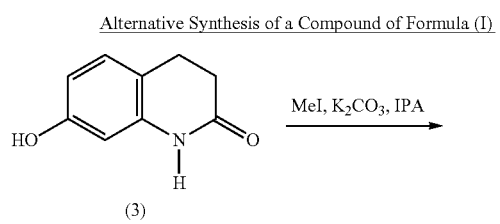

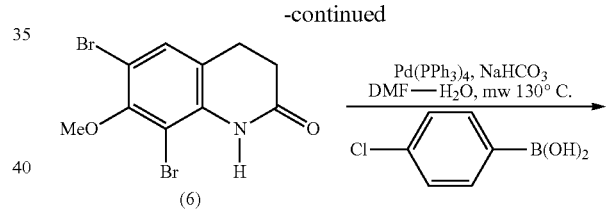

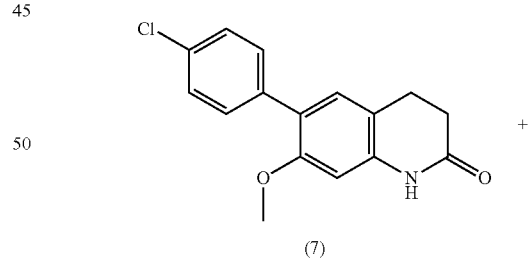

(7)

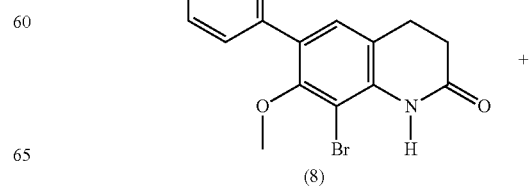

(8)

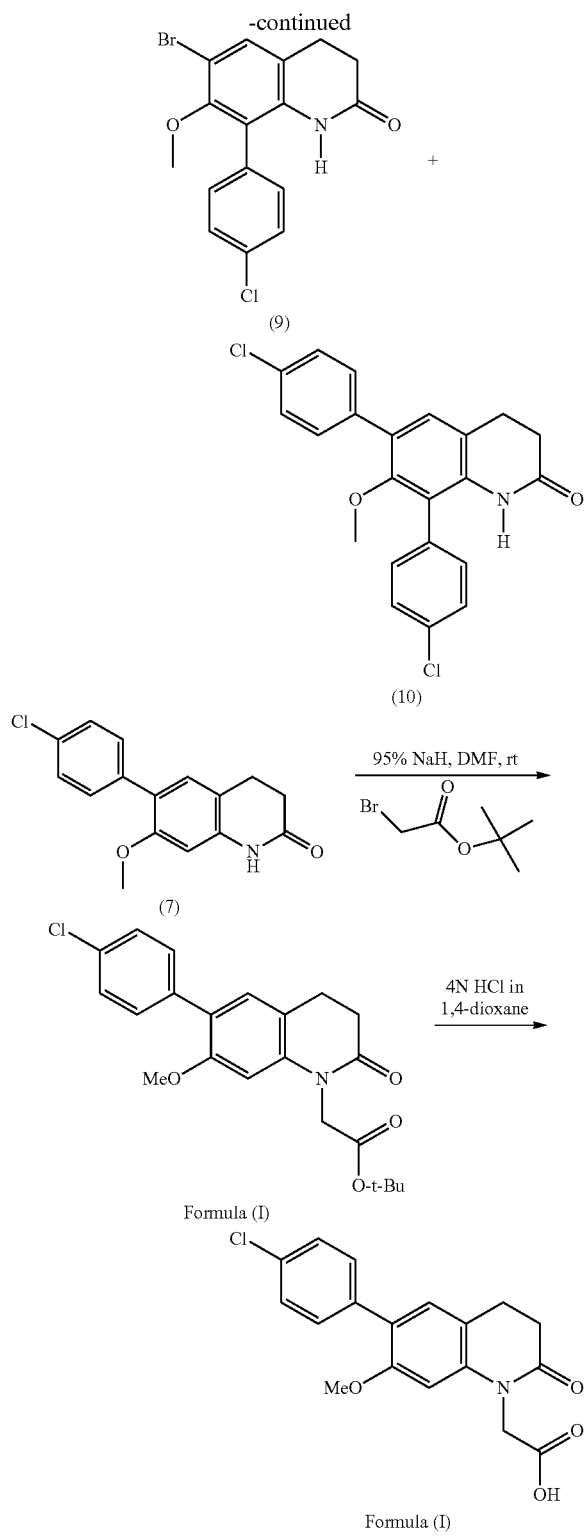

A. Synthesis of a Compound of Formula (4)

To a solution of 7-hydroxy-3,4-dihydroquinolin-2(1H)-one (3) (16.317 g, 100 mmol) in anhydrous isopropanol (200 mL) was added potassium carbonate (16.585 g, 120.0 mmol) with stirring under an atmosphere of dry $N_2$. The reaction mixture was stirred at room temperature for 30 minutes, then iodomethane (10.0 mL, 161.3 mmol) was added slowly. The reaction was heated to reflux with stirring for 60 hours, cooled, and the solvent evaporated under reduced pressure. To this residue water (200 mL) was added, and the mixture stirred and sonicated, filtered, and the pale yellow solid was washed with water (1000 mL), and dried under reduced pressure. To the crude dry solid was added 15% ethyl acetate in n-hexane (150 mL), and the mixture sonicated, filtered, washed with n-hexane (50 mL), and dried under reduced pressure, to afford 7-methoxy-3,4-dihydroquinolin-2(1H)-one (15.865 g, 89.5 mmol, 90%), the compound of formula (4). LCMS mz 178.0 (M+H), 200.0 (M+Na), anal HPLC >95% in purity, $^1$H NMR (400 MHz; dmso-D6) δ 7.09 (d, J=8.2 Hz, 1H); 6.57 (dd, J=8.2 and 2.7 Hz, 1H); 6.48 (d, J=2.7 Hz, 1H); 3.78 (s, 2H); 2.90 (t, J=7.0 Hz, 2H); 2.57 (t, J=7.0 Hz, 2H).

B. Synthesis of Compounds of Formulae (5) and (6)

To a suspension of 7-methoxy-3,4-dihydroquinolin-2(1H)-one (3.544 g, 20.0 mmol) in hot water (50 mL) was added dropwise a solution of bromine (3.520 g, 22.0 mmol) and potassium bromide (4.8 g, 40.0 mmol) in water (30 mL) under an atmosphere of dry $N_2$. The reaction mixture was heated to reflux with stirring for 16 hours, then cooled, sonicated, filtered, the solid washed with water (500 mL), and dried under reduced pressure to afford a white solid (5.036 g, ca 90% yield), which is a mixture of 6-bromo-7-methoxy-3,4-dihydroquinolin-2(1H)-one (5) (70% in $^1$HNMR) and 6,8-dibromo-7-methoxy-3,4-dihydroquinolin-2(1H)-one (6) (30%).

A portion of the mixture thus obtained (3.668 g) was treated with 15% ethyl acetate in n-hexane (20 mL), sonicated, filtered, the solid washed with n-hexane (20 mL), and dried under reduced pressure, to afford 6-bromo-7-methoxy-3,4-dihydroquinolin-2(1H)-one (5) (1.464 g, 5.7 mmol, 24%). LCMS mz 255.9 (M−H) and 257.9 (M+H), anal HPLC >94% in purity, $^1$H NMR (400 MHz; CDCl$_3$) δ 7.64 (s, 1H); 7.32 (d, J=0.8 Hz, 1H); 6.29 (s, 1H); 3.87 (s, 3H); 2.90 (m, 2H); 2.62 (m, 2H).

C. Synthesis of Compounds of Formulae (7), (8), (9) and (10)

To a solution of the crude mixture of 6-bromo-7-methoxy-3,4-dihydroquinolin-2(1H)-one (5) (330 mg, 1.29 mmol) and 6,8-dibromo-7-methoxy-3,4-dihydroquinolin-2(1H)-one (6) (185 mg, 0.55 mmol) in N,N-dimethylformamide (2.5 mL) was added 4-chlorophenylboronic acid (375 mg, 2.4 mmol), sodium bicarbonate (504 mg, 6.0 mmol) and water (0.5 mL) in a Biotage microwave vial. The reaction mixture was stirred for 5 minutes under an atmosphere of dry $N_2$, and Pd(PPh$_3$)$_4$ (30 mg, 0.025 mmol) was added. The resulting mixture was sealed, and subjected to microwave irradiation at 130° C. for 30 minutes. The product was cooled, diluted with ethyl acetate (10 mL), filtered through celite, washed with 10% N,N-dimethylformamide in ethyl acetate (60 mL), and transferred to a separation funnel. The organic phase was washed with 1N sodium carbonate (30 mL), 30% ammonium chloride (30 mL) and brine (30 mL), and dried and concentrated under reduced pressure. The crude product was purified by preparative HPLC with a gradient acetonitrile/water (5-98%), and the following four compounds were separated:

6-(4-chlorophenyl)-7-methoxy-3,4-dihydroquinolin-2(1H)-one (7) (222 mg, 0.77 mmol, 60%): LCMS mz 288.0 (M+H), anal HPLC >98% in purity, $^1$H NMR (400 MHz;

CDCl$_3$) δ 7.50 (s, 1H); 7.42 (m, 2H); 7.36 (m, 2H); 7.08 (s, 1H); 6.34 (s, 1H); 3.78 (s, 3H); 2.95 (t, J=7.2 Hz, 2H); 2.66 (m, 2H).

8-bromo-6-(4-chlorophenyl)-7-methoxy-3,4-dihydroquinolin-2(1H)-one (8) (13 mg, 0.035 mmol): LCMS m/z 367.9 (M+H), anal HPLC >96% in purity, $^1$H NMR (400 MHz; CDCl$_3$) δ 7.49 (m, 2H); 7.39 (s, 1H); 7.24 (m, 2H); 7.06 (s, 1H); 3.43 (s, 3H); 2.97 (m, 2H); 2.62 (m, 2H).

6-bromo-8-(4-chlorophenyl)-7-methoxy-3,4-dihydroquinolin-2(1H)-one (9) (9 mg, 0.024 mmol): LCMS m/z 367.9 (M+H), anal HPLC >94% in purity, $^1$H NMR (400 MHz; CDCl$_3$) δ 7.83 (s, 1H); 7.50 (m, 2H); 7.40 (m, 2H); 7.04 (s, 1H); 3.44 (s, 3H); 3.01 (m, 2H); 2.64 (m, 2H).

6,8-bis(4-chlorophenyl)-7-methoxy-3,4-dihydroquinolin-2(1H)-one (10) (80 mg, 0.20 mmol): LCMS m/z 399.9 (M+H), anal HPLC >98% in purity, $^1$H NMR (400 MHz; CDCl$_3$) δ 7.46-7.52 (m, 4H); 7.36-7.42 (m, 2H); 7.26-7.32 (m, 2H); 7.16 (s, 1H); 7.12 (s, 1H); 3.08 (s, 3H); 3.02 (m, 2H); 2.66 (m, 2H).

D. Synthesis of a Compound of Formula (I) in which R$^1$ is t-Butoxycarboxymethyl, R$^2$, R$^3$, R$^5$, and R$^6$ are Hydrogen, R$^4$ is 6-(4-chloromethyl)phenyl), R$^7$ is Methoxy, and X$^1$ and X$^2$ are both —CH=

To a mixture of 95% dry sodium hydride (24 mg, 1.00 mmol) in anhydrous N,N-dimethylformamide (8 mL) at room temperature was added a solution of 6-(4-chlorophenyl)-7-methoxy-3,4-dihydroquinolin-2(1H)-one (7) (110 mg, 0.38 mmol) in N,N-dimethylformamide. The reaction mixture was stirred for 30 minutes under an atmosphere of dry N$_2$, followed by addition of a solution of tert-butyl bromoacetate (390 mg, 2.00 mmol) in N,N-dimethylformamide (2 mL). The reaction mixture was stirred at room temperature until majority of the starting material was converted (as shown by LCMS), then it was quenched by addition of methanol (10 mL). The mixture was concentrated under reduced pressure, anhydrous toluene (10 mL) was added to the residue, and the solvent removed under reduced pressure, to afford crude (tert-butyl 2-(6-(4-chlorophenyl)-7-methoxy-2-oxo-3,4-dihydroquinolin-1 (2H)-yl)acetate).

Synthesis of a Compound of Formula (I) in which R$^1$ is —CH$_2$COOH

To the crude (tert-butyl 2-(6-(4-chlorophenyl)-7-methoxy-2-oxo-3,4-dihydroquinolin-1(2H)-yl)acetate) form Example 4D was added 4N hydrochloric acid in 1,4-dioxane (10 mL, 40 mmol). The reaction mixture was stirred at room temperature for 4 hours, and concentrated under reduced pressure. A second portion of 4N hydrochloric acid in 1,4-dioxane (10 mL, 40 mmol) and anhydrous N,N-dimethylformamide (2 mL) were added, and the mixture stirred for another 13 hours. The solvent was removed under reduced pressure, and the crude reaction product subjected to reverse phase HPLC with a gradient of acetonitrile/water (2% to 98%) to afford 2-(6-(4-chlorophenyl)-7-methoxy-2-oxo-3,4-dihydroquinolin-1 (2H)-yl)acetic acid (95 mg, 0.27 mmol, 72%). LCMS m/z 346.0 (M+H), 368.0 (M+Na), anal HPLC >98% in purity. $^1$H NMR (400 MHz; CDCl$_3$) δ 7.42 (d, J=8.6 Hz, 2H); 7.36 (d, J=8.6 Hz, 2H); 7.11 (s, 1H); 6.48 (s, 1H); 4.75 (s, 2H); 3.79 (s, 3H); 2.93 (m, 2H); 2.75 (m, 2H).

F. Synthesis of Additional Compounds of Formula (I)

Similarly, following the above procedure from Example 4A, 4B, 4C, 4D and 4E but optionally replacing 4-chlorophenyl boronic acid with other optionally substituted aryl boronic acids, the following compounds of Formula (I) were prepared:

| | |
|---|---|
| 77 | 6-(4-chlorophenyl)-7-methoxy-3,4-dihydroquinolin-2(1H)-one |
| 78 | 8-bromo-6-(4-chlorophenyl)-7-methoxy-3,4-dihydroquinolin-2(1H)-one |
| 79 | 2-(7-methoxy-2-oxo-6-(4-(trifluoromethyl)phenyl)-3,4-dihydroquinolin-1(2H)-yl)acetic acid |
| 80 | 2-(6-(4-chlorophenyl)-7-methoxy-2-oxo-3,4-dihydroquinolin-1(2H)-yl)acetic acid |
| 81 | 2-(6,8-bis(4-chlorophenyl)-7-methoxy-2-oxo-3,4-dihydroquinolin-1(2H)-yl)acetic acid |
| 82 | 6-(3-fluoro-4-(trifluoromethyl)phenyl)-7-methoxy-3,4-dihydroquinolin-2(1H)-one |
| 83 | 7-methoxy-6-[4-(trifluoromethyl)phenyl]-3,4-dihydroquinolin-2(1H)-one |
| 84 | 6,8-bis(4-chlorophenyl)-7-methoxy-3,4-dihydroquinolin-2(1H)-one |
| 85 | tert-butyl-2-(7-methoxy-2-oxo-6-(4-(trifluoromethyl)phenyl)-3,4-dihydroquinolin-1(2H)-yl)acetate |

G. Synthesis of Additional Compounds of Formula (I)

Similarly, following the above procedure from Example 4A, 4B, 4C, 4D and 4E, but optionally replacing 4-chlorophenylboronic acid with other optionally substituted aryl boronic acids, other compounds of Formula (I) are prepared:

EXAMPLE 5

Alternative Synthesis of a Compound of Formula (I)

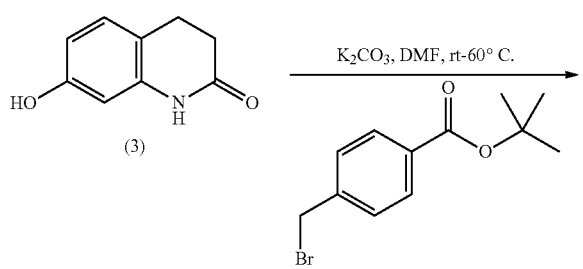

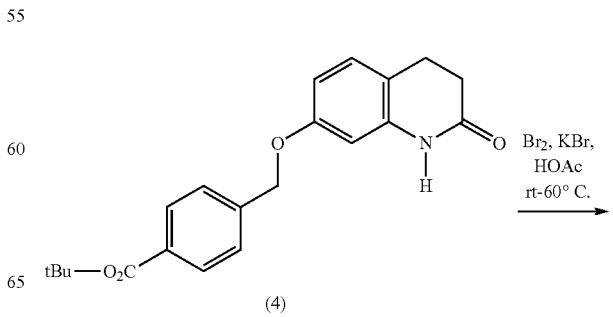

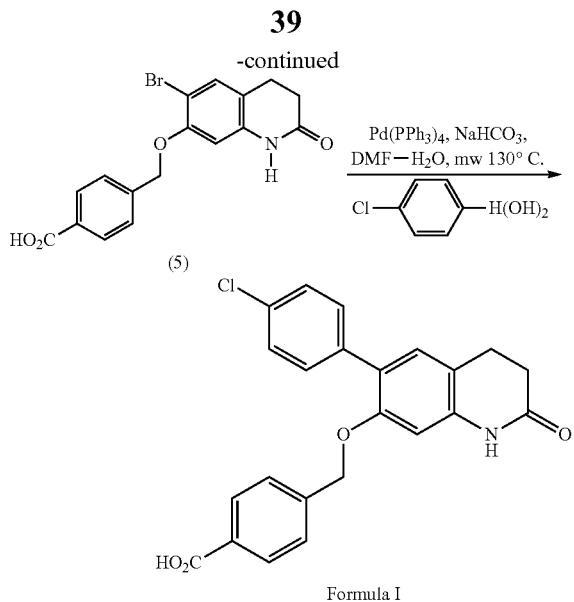

Formula I

A. Preparation of a Compound of Formula (4)

To a solution of 7-hydroxy-3,4-dihydroquinolin-2(1H)-one (2.015 g, 12.35 mmol) in anhydrous N,N-dimethylformamide (25 mL) was added potassium carbonate (1.880 g, 13.60 mmol) with stirring, and tert-butyl 4-(bromomethyl) benzoate (2.960 g, 10.83 mmol) in N,N-dimethylformamide (10 mL) was added. The reaction mixture was stirred at room temperature for 30 minutes, then heated to 60° C. for 72 hours. The mixture was cooled, the solvent volume reduced to half under reduced pressure, and the residue poured slowly into water (100 mL) with stirring. Diethyl ether (5 mL) was added, the mixture sonicated, filtered, and the white solid thus obtained was washed with saturated sodium carbonate (60 mL), water (200 mL), diethyl ether (15 mL), and dried to afford tert-butyl 4-((2-oxo-1,2,3,4-tetrahydroquinolin-7-yloxy)methyl)benzoate (2.122 g, 6.00 mmol, 55%). LCMS mz 376.0 (M+Na), anal HPLC >92% in purity, $^1$H NMR (400 MHz; CDCl$_3$) 8.00 (d, J=8.6 Hz, 1H); 7.55 (s, 2H); 7.45 (d, J=8.6 Hz, 2H); 7.05 (d, J=8.2 Hz, 1H); 6.57 (dd, J=8.4 and 2.5 Hz, 1H); 6.35 (d, J=2.3 Hz, 1H); 2.90 (m, 2H); 2.61 (m, 2H); 1.60 (s, 9H).

B. Preparation of a Compound of Formula (5)

To a suspension of tert-butyl 4-((2-oxo-1,2,3,4-tetrahydroquinolin-7-yloxy)methyl)benzoate (550 mg, 1.56 mmol) in glacial acetic acid (5 mL) was added dropwise a solution of bromine (800 mg, 5.00 mmol) and potassium bromide (595 mg, 5.0 mmol) in acetic acid (10 mL) under an atmosphere of dry N$_2$, and the mixture stirred at room temperature for 1 hour. The reaction mixture was warmed to 60° C. for 18 hours, then cooled, and the solvent evaporated under reduced pressure. The residue was poured slowly into water (40 mL) with stirring, diethyl ether (3 mL) was added, and the mixture sonicated, filtered, the solid thus obtained was washed with saturated sodium carbonate (30 mL), water (50 mL), diethyl ether (10 mL), and dried under reduced pressure to afford 4-((6-bromo-2-oxo-1,2,3,4-tetrahydroquinolin-7-yloxy)methyl)benzoic acid (334 mg, 0.89 mmol, 57%). LCMS mz 375.9 (M−H) and 377.9 (M+H), anal HPLC >91% in purity, $^1$H NMR (400 MHz; CD$_3$CN) δ8.25 (bs, 1H); 8.09 (d, J=8.6 Hz, 2H); 7.65 (d, J=8.6 Hz, 2H); 7.42 (s, 1H); 6.62 (s, 1H); 5.26 (s, 2H); 2.91 (m, 2H); 2.53 (m, 2H).

C. Preparation of a Compound of Formula (I)

To a solution of 4-((6-bromo-2-oxo-1,2,3,4-tetrahydroquinolin-7-yloxy)methyl)benzoic acid (100 mg, 0.27 mmol) and 4-chlorophenyl boronic acid (62 mg, 0.40 mmol) in N,N-dimethylformamide (2.0 mL) in a Biotage microwave vial was added sodium bicarbonate (200 mg, 2.38 mmol) and water (0.50 mL). The reaction mixture was stirred for 5 minutes under an atmosphere of dry N$_2$. Pd(PPh$_3$)$_4$ (10 mg, 0.009 mmol) was added, and the resulting mixture was sealed and subjected to microwave irradiation at 130° C. for 8 minutes. The mixture was cooled, diluted with ethyl acetate (5 mL), filtered through celite, washed with 10% N,N-dimethylformamide in ethyl acetate (40 mL), transferred to a separation funnel, and the organic phase was washed with 1N sodium carbonate (20 mL), 30% ammonium chloride (20 mL) and brine (30 mL), dried and the solvent removed under reduced pressure. The crude product was purified by preparative HPLC with a gradient acetonitrile/water (5-98%) to afford 4-((6-(4-chlorophenyl)-2-oxo-1,2,3,4-tetrahydroquinolin-7-yloxy)methyl)benzoic acid (72 mg, 0.18 mmol, 66%). LCMS mz 408.0 (M+H), 430.0 (M+Na), anal HPLC >96% in purity, $^1$H NMR (400 MHz; dmso-D6) δ10.1 (σ, 1H), 7.95 (d, J=8.2 Hz, 2H); 7.55 (d, J=9.0 Hz, 2H); 7.48 (m, 4H); 7.18 (s, 1H); 6.69 (s, 1H); 5.15 (s, 2H); 2.87 (m, 2H); 2.47 (m, 2H).

D. Preparation of other Compounds of Formula (I)

Similarly, following the procedures of Example 5A, 5B, and 5C, but optionally replacing tert-butyl 4-(bromomethyl) benzoate with tert-butyl bromoacetate, or replacing 4-chlorophenyl boronic acid with other optionally substituted aryl boronic acids, the following compounds of Formula I were prepared:

4-((2-oxo-6-(4-(trifluoromethyl)phenyl)-1,2,3,4-tetrahydroquinolin-7-yloxy)methyl)benzoic acid;

2-(2-oxo-6-(4-(trifluoromethyl)phenyl)-1,2,3,4-tetrahydroquinolin-7-yloxy)acetic acid;

2-(2-oxo-6-(4-phenoxyphenyl)-1,2,3,4-tetrahydroquinolin-7-yloxy)acetic acid; and 2-(6-(4-chlorophenyl)-2-oxo-1,2,3,4-tetrahydroquinolin-7-yloxy)acetic acid.

EXAMPLE 6

Synthesis of a Compound of Formula (I)

-continued

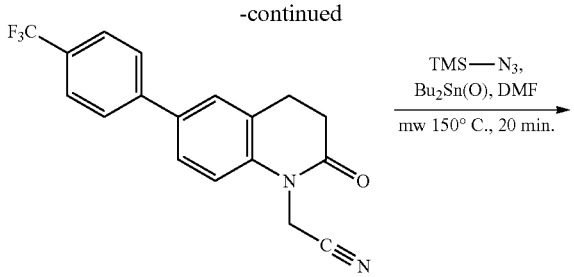

Formula (I) in which R[1] is cyanomethyl

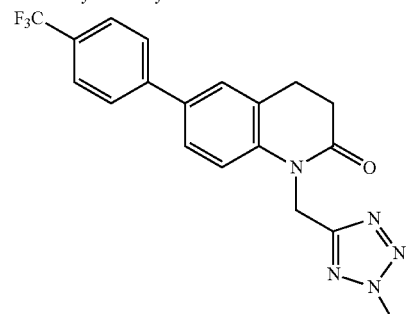

Formula (I) in which R[1] is tetrazolylmethyl

A. Synthesis of a Compound of Formula (I) in which R[1] is Cyanomethyl

To a mixture of 95% dry sodium hydride (48 mg, 2.00 mmol) in anhydrous N,N-dimethylformamide (10 mL) at room temperature was added a solution of 6-(4-(trifluoromethyl)phenyl)-3,4-dihydroquinolin-2(1H)-one (291 mg, 1.00 mmol). The reaction mixture was stirred for 30 minutes under an atmosphere of dry $N_2$, followed by addition of a solution of 2-bromoacetonitrile (480 mg, 4.00 mmol) in N,N-dimethylformamide (2 mL). The reaction mixture was stirred at room temperature until the majority of the starting material was converted (as checked by LCMS), then quenched by addition of methanol (10 mL). The mixture was concentrated under reduced pressure, and the residue was subjected to reverse phase HPLC with a gradient of acetonitrile/water (2% to 98%) to afford 2-(2-oxo-6-(4-(trifluoromethyl)phenyl)-3,4-dihydroquinolin-1(2H)-yl)acetonitrile (compound No. 90) (307 mg, 0.93 mmol, 93%). LCMS mz 331.0 (M+H), 353.0 (M+Na), anal HPLC >98% in purity. $^1$H NMR (400 MHz; $CDCl_3$) δ 7.69 (m, 4H); 7.57 (dd, J=8.4 and 2.1 Hz, 1H); 7.47 (d, J=3.0 Hz, 1H); 7.16 (d, J=8.2 Hz, 1H); 6.90 (s, 2H); 3.05 (m, 2H); 2.79 (m, 2H).

B. Synthesis of Compounds of Formula (I) in which R[1] is Tetrazolylmethyl

A Biotage microwave vial was charged with 2-(2-oxo-6-(4-(trifluoromethyl)phenyl)-3,4-dihydroquinolin-1(2H)-yl)acetonitrile (66 mg, 0.20 mmol), azidotrimethylsilane (46 mg, 0.40 mmol), dibutyltin oxide (8 mg, 0.03 mmol), and anhydrous N,N-dimethylformamide (2.5 mL), and the vial capped. The reaction mixture was heated to 160° C. and irradiated for 25 minutes. LCMS showed only ca 63% conversion. Additional azidotrimethylsilane (46 mg, 0.40 mmol) was added, and heated again at 160° C. for an additional 30 minutes. LCMS showed the disappearance of starting material. The reaction mixture was diluted with ethyl acetate (30 mL), washed with 30% aqeuous ammonium chloride (2×10 mL), brine (20 mL), and dried over sodium sulfate. The solvent was removed from the solution under reduced pressure to give a pale yellow solid. Ethyl ether (3 mL) was added, sonicated, filtered, washed with ethyl ether (10 mL), dried to afford 1-((2H-tetrazol-5-yl)methyl)-6-(4-(trifluoromethyl)phenyl)-3,4-dihydroquinolin-2(1H)-one as a white solid (59 mg, 0.16 mmol, 80%). LCMS mz 374.0 (M+H), anal HPLC >97% purity, $^1$HNMR (400 MHz, $CD_3CN$) δ 7.83 (m, 4H); 7.65 (d, J=2.0 Hz, 1H); 7.62 (dd, J=8.4 and 2.1 Hz, 1H); 7.30 (d, J=8.6 Hz, 1H); 5.46 (s, 2H); 3.11 (m, 2H); 2.77 (m, 2H).

C. Synthesis of Additional Compounds of Formula (I)

Similarly, following the above procedures of Example 6A and 6B, but optionally replacing 6-(4-(trifluoromethyl)phenyl)-3,4-dihydroquinolin-2(1H)-one with other optionally substituted aryl-3,4-dihydroquinolin-2(1H)-one, other compounds of Formula (I) are prepared:

EXAMPLE 7

Synthesis of a Compound of Formula (I)

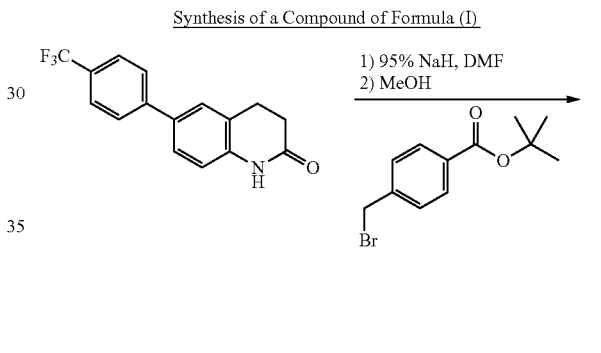

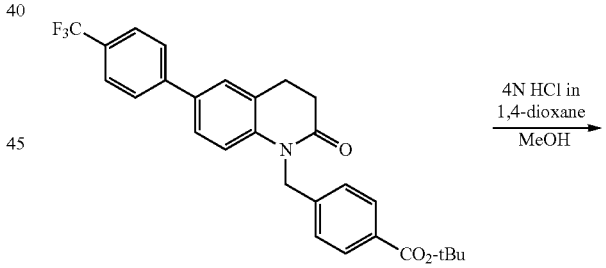

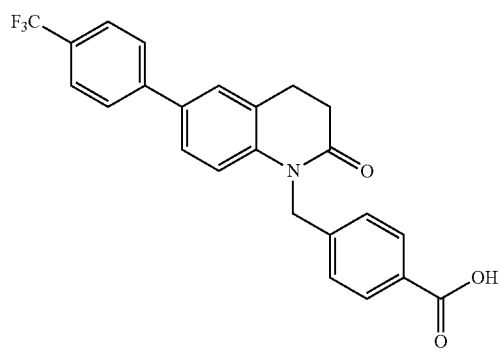

A. Synthesis of a Compound of Formula (I) in which R¹ is 4-(t-Butoxycarbonyl)-phenylmethyl To a mixture of 95% dry sodium hydride (12 mg, 0.50 mmol) in anhydrous N,N-dimethylformamide (4 mL) at room temperature was added a solution of 6-(4-(trifluoromethyl)phenyl)-3,4-dihydroquinolin-2(1H)-one (78 mg, 0.30 mmol) (PT-010 made as in Example 1B, above) in anhydrous N,N-dimethylformamide (1 mL). The reaction mixture was stirred for 30 minutes under an atmosphere of dry $N_2$, followed by addition of a solution of tert-butyl 4-(bromomethyl) benzoate (271 mg, 1.00 mmol) in N,N-dimethylformamide (1.0 mL). The reaction mixture was stirred at room temperature until the majority of the starting material was converted (checked by LCMS), then it was quenched by addition of methanol (5 mL). The reaction mixture was concentrated under reduced pressure, anhydrous toluene (10 mL) was added, and the solvent removed under reduced pressure. To this crude product (tert-butyl 4-((2-oxo-6-(4-(trifluoromethyl)phenyl)-3,4-dihydroquinolin-1(2H)-yl)methyl)benzoate) was added 4N hydrochloric acid in 1,4-dioxane (10 mL, 40 mmol). The reaction mixture was stirred at room temperature for 4 hours, and the solvent removed under reduced pressure. A second portion of 4N hydrochloric acid in 1,4-dioxane (10 mL, 40 mmol) was added with stirring at room temperature for another 13 hours, the solvent removed under reduced pressure. The crude reaction product was subjected to reverse phase HPLC with a gradient of MeCN/$H_2O$ (2% to 98%) to afford 4-((2-oxo-6-(4-(trifluoromethyl)phenyl)-3,4-dihydroquinolin-1(2H)-yl)methyl)benzoic acid (70 mg, 0.16 mmol, 53%) (PT-088). LCMS mz 488.0 (M+H), 510.0 (M+Na), anal HPLC >98% in purity. ¹H NMR (400 MHz; DMSO-d6) δ 7.90 (d, J=8.2 Hz, 2H); 7.86 (d, J=8.2 Hz, 2H); 7.78 (d, J=8.2 Hz, 2H); 7.68 (d, J=2.1 Hz, 1H); 7.53 (dd, J=8.3 and 2.1 Hz, 1H); 7.38 (d, J=8.2 Hz, 2H); 7.00 (d, J=8.6 Hz, 1H); 5.27 (s, 2H); 3.08 (m, 2H), 2.79 (m, 2H).

B. Synthesis of Additional Compounds of Formula (I)

Similarly, following the above procedure of Example 7A, but optionally replacing 6-(4-(trifluoromethyl)phenyl)-3,4-dihydroquinolin-2(1H)-one with another optionally substituted 6-phenyl-3,4-dihydroquinolin-2(1H)-one derivative, or optionally replacing the tert-butyl 4-(bromomethyl)benzoate with other optionally substituted bromomethylbenzene compounds, the following compounds of Formula (I) were prepared.

| | |
|---|---|
| 86 | 4-((2-oxo-6-(4-(trifluoromethyl)phenyl)-3,4-dihydroquinolin-1(2H)-yl)methyl)benzoic acid |
| 87 | methyl 4-((2-oxo-6-(4-(trifluoromethyl)phenyl)-3,4-dihydroquinolin-1(2H)-yl)methyl)benzoate |

C. Synthesis of Additional Compounds of Formula (I)

Similarly, following the above procedure of Example 7A, but optionally replacing 6-(4-(trifluoromethyl)phenyl)-3,4-dihydroquinolin-2(1H)-one with another optionally substituted 6-phenyl-3,4-dihydroquinolin-2(1H)-one derivatives, or optionally replacing the tert-butyl 4-(bromomethyl)benzoate with other optionally substituted bromomethylbenzene compounds, other compounds of Formula (I) are prepared.

EXAMPLE 8

Synthesis of a Compound of Formula (I)

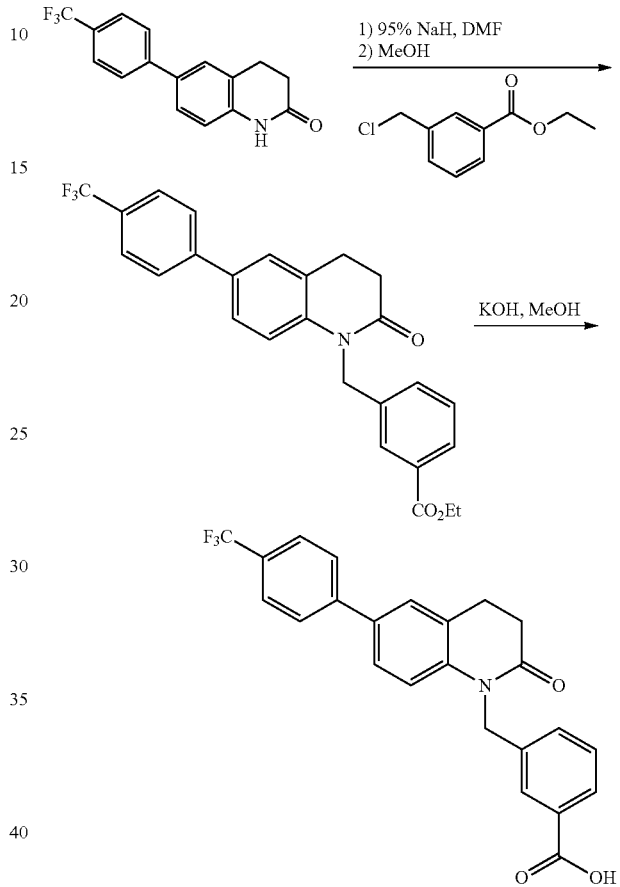

A. Synthesis of a Compound of Formula (I) in which R¹ is 3-Ethoxycarbonyl)-phenylmethyl To a mixture of 95% dry sodium hydride (18 mg, 0.75 mmol) in anhydrous N,N-dimethylformamide (4 mL) at room temperature was added a solution of 6-(4-(trifluoromethyl)phenyl)-3,4-dihydroquinolin-2(1H)-one (90 mg, 0.31 mmol) (PT-010 made as in Example 1B, above) in anhydrous N,N-dimethylformamide (1 mL). The reaction mixture was stirred for 30 minutes under an atmosphere of dry $N_2$, followed by addition of a solution of ethyl 3-(chloromethyl) benzoate (100 mg, 1.00 mmol) in N,N-dimethylformamide (1.0 mL). The reaction mixture was stirred at room temperature until most of the starting material was converted (checked by LCMS), then it was quenched by addition of methanol (5 mL). The reaction mixture was concentrated under a reduced pressure, diluted with ethyl acetate (50 mL), and the organic phase washed with 2N sodium carbonate (20 mL), 30% ammonium chloride (20 mL), brine (20 mL), dried over magnesium sulfate, and the solvent removed under reduced pressure. The residue was dissolved in N,N-dimethylformamide (3 mL) and subjected to reverse phase HPLC with a gradient of acetonitrile/water (2% to 98%) to afford ethyl 3-((2-oxo-6-(4-(trifluoromethyl)phenyl)-3,4-dihydroquinolin-1(2H)-yl)methyl)benzoate (compound no. 91) (108 mg, 0.24 mmol, 77%) (PT-094). LCMS mz 455.0 (M+H), 476.0 (M+Na), anal HPLC >95% in purity. $^1$H NMR (400 MHz; CDCl$_3$) δ 7.94 (m, 2H); 7.64 (m, 4H); 7.41 (m, 3H); 7.30-7.37 (m, 1H); 6.92 (d, J=8.6 Hz, 1H); 5.27 (s, 2H); 4.37 (q, J=7.0 Hz, 2H); 3.08 (m, 2H), 2.86 (m, 2H); 1.39 (t, J=7.0 Hz, 3H).

B. Synthesis of a Compound of Formula (I)—Hydrolysis of Ester

To a solution of ethyl 3-((2-oxo-6-(4-(trifluoromethyl)phenyl)-3,4-dihydroquinolin-1(2H)-yl)methyl)benzoate (45 mg, 0.10 mmol) (PT-094) in N,N-dimethylformamide (2.0 mL) was added 1N potassium hydroxide in methanol (10 mL, 10 mmol). The reaction mixture was stirred at room temperature for 17 hours, and then the solvent was removed under reduced pressure. Water (5.0 mL) was added, and the pH was adjusted to 4-5. The mixture was extracted with ethyl acetate (3×20 mL), and the combined organic phase was washed with 30% ammonium chloride (20 mL), brine (20 mL), dried over magnesium sulfate, and the solvent removed under reduced pressure. The residue was subjected to reverse phase HPLC with a gradient of acetonitrile/water (2% to 98%) to afford 3-((2-oxo-6-(4-(trifluoromethyl)phenyl)-3,4-dihydroquinolin-1(2H)-yl)methyl)benzoic acid (26 mg, 0.06 mmol, 60%) (PT-095). LCMS mz 426.0 M+H), 448.0 (M+Na). $^1$H NMR (400 MHz; CDCl$_3$) δ 8.06 (bs, 2H); 7.65 (m, 4H); 7.47 (m, 3H); 7.36 (m, 1H); 6.92 (d, J=8.6 Hz, 1H); 5.28 (s, 2H); 3.08 (m, 2H), 2.86 (m, 2H).

C. Synthesis of Additional Compounds of Formula (I)

Similarly, following the procedures of Example 8A and 8B, but optionally replacing 6-(4-(trifluoromethyl)phenyl)-3,4-dihydroquinolin-2(1H)-one with other optionally substituted 6-phenyl-3,4-dihydroquinolin-2(1H)-one derivatives, or optionally replacing the ethyl 3-(chloromethyl)benzoate with other optionally substituted chloromethylbenzene compounds, other compounds of Formula (I) are prepared.

EXAMPLE 9

Synthesis of a Compound of Formula (I)

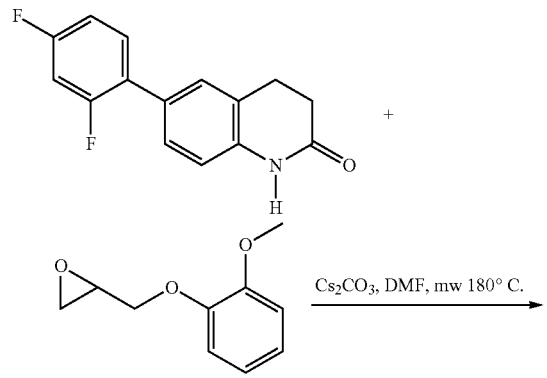

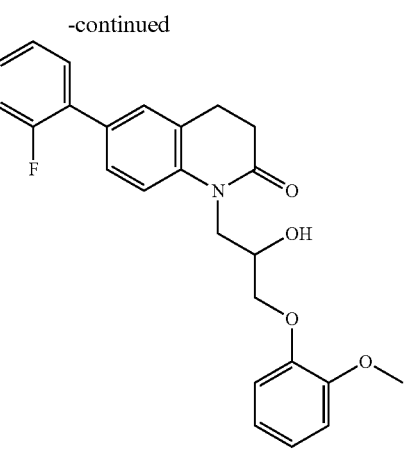

A. Synthesis of a Compound of Formula (I) in which R$^1$ is 2-hydroxy-3-2-methoxyphenoxy)propyl)

To a solution of 6-(2,4-difluorophenyl)-3,4-dihydroquinolin-2(1H)-one (180 mg, 0.69 mmol) (PT-012, made as in Example 1B, above) and 2-((2-methoxyphenoxy)methyl)oxirane (162 mg, 0.90 mmol) in anhydrous N,N-dimethylformamide (2 ml) was added caesium carbonate (326 mg, 1.00 mmol) in a 5 ml Personal Chemistry microwave reaction vial. The reaction vial was sealed, and subjected to microwave irradiation at 180° C. for 40 minutes. The reaction was cooled, poured into water (10 mL), extracted with ethyl acetate (2×30 mL), and the combined organic phases washed with water (30 mL), 2N sodium carbonate (30 mL), brine (40 mL), dried over sodium sulfate, and the solvent removed under reduced pressure. The residue was subjected to reverse phase HPLC with a gradient of acetonitrile/water (2% to 98%) to afford 6-(2,4-difluorophenyl)-1-(2-hydroxy-3-(2-methoxyphenoxy)propyl)-3,4-dihydroquinolin-2(1H)-one (148 mg, 0.34 mmol, 49%) (compound No. 88)). LCMS mz 440.0 (M+H), 462.0 (M+Na), anal HPLC >95% in purity. $^1$H NMR (400 MHz; CDCl$_3$) δ 7.46 (d, J=8.6 Hz, 1H); 7.36 (m, 2H); 7.31 (bs, 1H); 6.88-7.03 (m, 6H); 4.36 (m, H); 4.27 (s, 1H), 4.26 (d, J=2.3 Hz, 1H); 4.15 (dd, J=9.8 and 5.5 Hz, 1H); 4.00-4.10 (m, 2H); 3.88 (s, 3H), 2.99 (m, 2H); 2.76 (m, 2H).

B. Synthesis of Further Compounds of Formula (I)

Similarly, following the procedure of Example 9A, the following compound of Formula (I) was prepared:

1-(2-hydroxypropyl)-6-[4-(trifluoromethoxy)phenyl]-3,4-dihydroquinolin-2(1H)-one (compound no. 89)

C. Synthesis of Additional Compounds of Formula (I)

Similarly, following the procedure of Example 9A, but optionally replacing 6-(2,4-difluorophenyl)-3,4-dihydroquinolin-2(1H)-one with another optionally substituted 6-phenyl-3,4-dihydroquinolin-2(1H)-one derivative, or optionally replacing the 24(2-methoxyphenoxy)methyl)oxirane with other optionally substituted oxirane compounds, other compounds of Formula (I) are prepared.

EXAMPLE 10

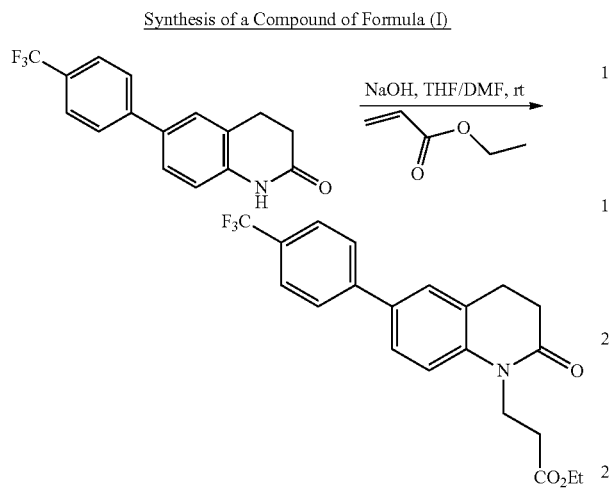

Synthesis of a Compound of Formula (I)

Preparation of a Compound of Formula (I) in which $R^1$ is Ethyl Propionate

A. Preparation of ethyl 3-(2-oxo-6-(4-(trifluoromethyl)phenyl)-3,4-dihydroquinolin-1(2H)-yl)propanoate To a solution of 6-(4-(trifluoromethyl)phenyl)-3,4-dihydroquinolin-2(1H)-one, prepared as described above (90 mg, 0.31 mmol) in anhydrous tetrahydrofuran (3 mL) was added at room temperature 20-40 mesh beads of sodium hydroxide (48 mg, 1.20 mmol) and ethyl acrylate (1.200 g, 1.20 mmol) in anhydrous N,N-dimethylformamide (1 mL). The reaction mixture was stirred for 4 hours under an atmosphere of dry $N_2$, followed by addition of a second portion of sodium hydroxide (96 mg, 2.40 mmol). The reaction was followed by LCMS and stirring was continued until all of the starting material had disappeared. Solvent was removed from the reaction mixture under reduced pressure, diluted with ethyl acetate (20 mL), and aqueous $Na_2SO_3$ (10 mL) added. The aqueous phase was extracted with ethyl acetate (3×20 mL), and the combined organic phase successively washed with 2N sodium carbonate (20 mL), 30% ammonium chloride (20 mL), brine (20 mL), and dried over magnesium sulfate. Evaporation of the solvent gave a crude mixture that was purified by reverse phase HPLC with a gradient of acetonitrile/water (2% to 98%) to afford ethyl 3-(2-oxo-6-(4-(trifluoromethyl)phenyl)-3,4-dihydroquinolin-1(2H)-yl)propanoate (65 mg, 0.18 mmol, 58%). LCMS mz 364.0 (M+H), 386.0 (M+Na), anal HPLC >99% in purity. $^1$H NMR (400 MHz; $CD_3CN$) δ7.87 (d, J=8.2 Hz, 2H); 7.81 (d, J=8.6 Hz, 2H); 7.66 (d, J=2.3 Hz, 1H); 7.63 (m, 1H); 7.26 (d, J=8.6 Hz, 1H); 4.25 (m, 2H); 3.02 (m, 2H); 2.67 (m, 4H).

HPLC also afforded a minor amount of 3-(2-oxo-6-(4-(trifluoromethyl)phenyl)-3,4-dihydroquinolin-1(2H)-yl)propanoic acid (23 mg, 0.06 mmol, 19%). %). LCMS mz 392.0 (M+H), 414.0 (M+Na), anal HPLC >98% in purity. $^1$H NMR (400 MHz; $CD_3CN$) δ7.83 (m, 4H); 7.63 (m, 2H); 7.26 (d, J=8.6 Hz, 1H); 4.26 (t, J=7.2 Hz, 2H); 4.13 (m, 2H); 3.00 (m, 2H); 2.66 (m, 4H); 1.25 (t, J=7.0 Hz, 3H).

B. Preparation of other Compounds of Formula (I) in which $R^1$ is an Ester Similarly, following the above procedure of Example 10A, but optionally replacing 6-(4-(trifluoromethyl)phenyl)-3,4-dihydroquinolin-2(1H)-one (202) with other 3,4-dihydroquinolin-2(1H)-one, or replacing ethyl acrylate with other tert-butyl acrylate, or performing a NaOH catalyzed ester hydrolysis of the intermediate 3-(2-oxo-3,4-dihydroquinolin-1(2H)-yl)propanoate, the following compounds of Formula I were prepared:

3-(7-methoxy-2-oxo-6-(4-phenoxyphenyl)-3,4-dihydroquinolin-1(2H)-yl)propanoic acid;

3-(7-methoxy-2-oxo-6-(4-(trifluoromethyl)phenyl)-3,4-dihydroquinolin-1 (2H)-yl)propanoic acid; and 3-(2-oxo-7-(3-(trifluoromethyl)phenyl)-3,4-dihydroquinolin-1 (2H)-yl)propanoic acid.

EXAMPLE 11

Synthesis of a Compound of Formula (I)

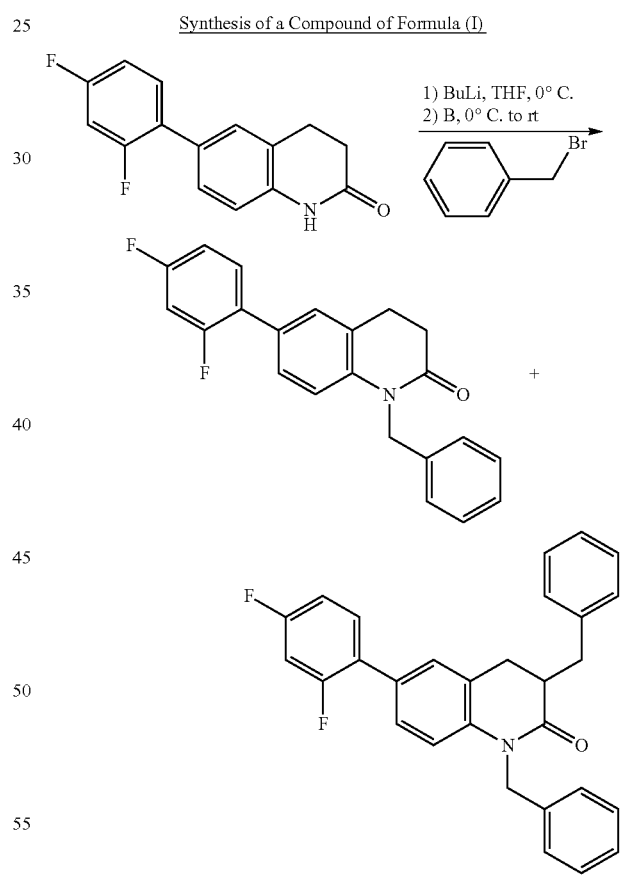

Preparation of a Compound of Formula (I) in which $R^1$ is Benzyl

A. Preparation of 1-benzyl-6-(2,4-difluorophenyl)-3,4-dihydroquinolin-2(1H)-one To a solution of 6-(2,4-difluorophenyl)-3,4-dihydroquinolin-2(1H)-one (130 mg, 0.50 mmol) in anhydrous tetrahydrofuran (5 mL) at 0° C. in a dry flask equipped with an inlet of dry nitrogen was added fresh 1.6 M n-butyl lithium in n-hexane (0.6 mL, 0.96 mmol) with stirring. The reaction mixture was stirred at 0° C. for 2 hours, followed by addition of a second portion of 1.6 M n-butyl lithium in n-hexane (0.6 mL, 0.96 mmol), and the mixture stirred for another 2 hours. To this mixture was added slowly a solution of benzyl bromide (855 mg, 5.00 mmol) in anhydrous tetrahydrofuran (3 mL) at 0° C., stirred overnight, and allowed to warm to room temperature. The reaction was followed by LCMS and stirring was continued until all of the starting material was consumed. The reaction mixture was quenched by slow addition of saturated aqueous ammonium chloride (10 mL) with stirring, concentrated under reduced pressure, diluted with ethyl acetate (20 mL) and dilute aqueous ammonium chloride (10 mL). The aqueous phase was extracted with ethyl acetate (3×20 mL), and the combined organic phase successively washed with 2N sodium carbonate (20 mL), 30% ammonium chloride (20 mL), brine (20 mL), and dried over magnesium sulfate. Evaporation of the solvent under reduced pressure gave a crude mixture, which was purified by reverse phase HPLC with a gradient of acetonitrile/water (2% to 98%) to afford 1-benzyl-6-(2,4-difluorophenyl)-3,4-dihydroquinolin-2(1H)-one (62 mg, 0.18 mmol, 35%). LCMS mz 350.0 (M+H), 372.0 (M+Na), anal HPLC >98% in purity. $^1$H NMR (400 MHz; CDCl$_3$) δ7.10-7.40 (m, 8H); 6.80-7.00 (m, 3H); 5.22 (s, 2H); 3.05 (m, 2H); 2.85 (m, 2H).

HPLC also gave 1,3-dibenzyl-6-(2,4-difluorophenyl)-3,4-dihydroquinolin-2(1H)-one (22 mg, 0.05 mmol, 10%). LCMS mz 440.0 (M+H), 462.0 (M+Na), anal HPLC >99% in purity. $^1$H NMR (400 MHz; CDCl$_3$) δ7.10-7.40 (m, 13H); 6.90-7.00 (m, 3H); 5.24 (m, 2H); 3.42 (dd, J=13.5 and 4.1 Hz, 1H); 2.80-3.10 (m, 2H); 2.60-2.75 (m, 2H).

EXAMPLE 12

Synthesis of a Compound of Formula (I)

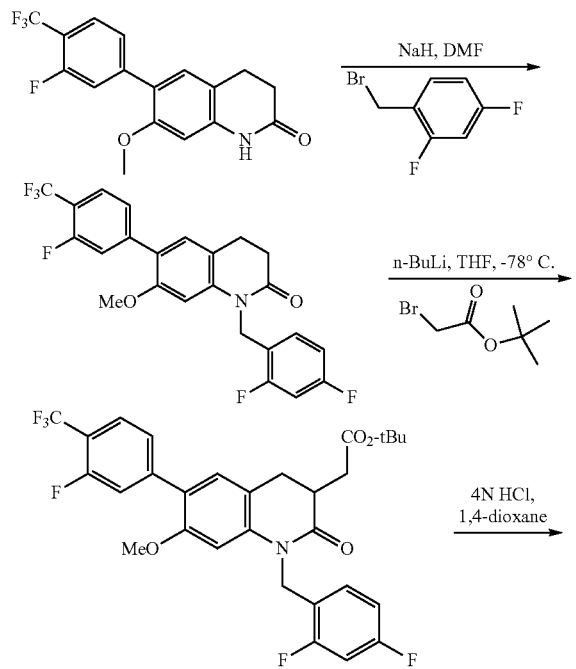

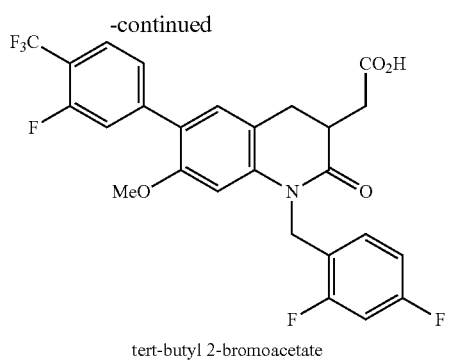

tert-butyl 2-bromoacetate

Preparation of a Compound of Formula (I) in which R$^1$ is 2,4-Difluorobenzyl, R$^5$ is —CH$_2$CO$_2$H, R$^4$ is 3-Fluoro-4-trifluoromethyl, and R$^7$ is Methoxy A. Preparation of 1-(2,4-difluorobenzyl)-6-(3-fluoro-4-(trifluoromethyl)phenyl)-7-methoxy-3,4-dihydroquinolin-2(1H)-one To a suspension of 95% sodium hydride in anhydrous N,N-dimethylformamide (2 mL) at room temperature in a dry flask equipped with an inlet of dry nitrogen was added a solution of 6-(3-fluoro-4-(trifluoromethyl)phenyl)-7-methoxy-3,4-dihydroquinolin-2(1H)-one, prepared a shown above (53 mg, 0.10 mmol) in N,N-dimethylformamide (1 mL) with stirring. The reaction mixture was stirred for 30 minutes, followed by addition of 1-(bromomethyl)-2,4-difluorobenzene (207 mg, 1.0 mmol), and the reaction mixture stirred overnight. The reaction was followed by LCMS and stirring was continued as needed until the starting material was consumed. The reaction mixture was quenched by addition of saturated aqueous ammonium chloride (5 mL) with stirring, concentrated under reduced pressure, diluted with ethyl acetate (20 mL) and dilute aqueous ammonium chloride (10 mL). The aqueous phase was extracted with ethyl acetate (3×20 mL), and the combined organic phase was successively washed with 2N sodium carbonate (20 mL), 30% aqueous ammonium chloride (20 mL), brine (20 mL), and dried over magnesium sulfate. Evaporation of the solvent under reduced pressure gave a crude mixture that was purified by reverse phase HPLC with a gradient of acetonitrile/water (2% to 98%) to afford 1-(2,4-difluorobenzyl)-6-(3-fluoro-4-(trifluoromethyl)phenyl)-7-methoxy-3,4-dihydroquinolin-2(1H)-one (25 mg, 0.05 mmol, 52%). LCMS mz 466.0 (M+H), 487.9 (M+Na), anal HPLC >98% in purity. $^1$H NMR (400 MHz; CDCl$_3$) δ7.58 (t, J=7.8 Hz, 1H); 7.34 (m, 2H); 7.21 (m, 1H); 7.10 (s, 1H); 6.80-6.89 (m, 2H); 6.57 (s, 1H); 5.24 (s, 2H); 3.70 (s, 3H); 2.94 (m, 2H); 2.81 (m, 2H).

B. Preparation of tert-butyl 2-(1-(2,4-difluorobenzyl)-6-(3-fluoro-4-(trifluoromethyl)phenyl)-7-methoxy-2-oxo-1,2,3,4-tetrahydroquinolin-3-yl)acetate To a solution of 1-(2,4-difluorobenzyl)-6-(3-fluoro-4-(trifluoromethyl)phenyl)-7-methoxy-3,4-dihydroquinolin-2(1H)-one (14 mg, 0.03 mmol) in anhydrous tetrahydrofuran (1 mL) at −78° C. in a dry flask equipped with an inlet of dry nitrogen was added fresh 1.6 M n-butyl lithium in n-hexane (40 μL, 0.06 mmol) with stirring. The reaction mixture was stirred at −78° C. for 30 minutes, then at 0° C. for 1 hour. The reaction mixture was re-cooled to −78° C., a solution of tert-butyl bromoacetate (98 mg, 0.50 mmol) in anhydrous tetrahydrofuran added (0.5 mL), and the reaction mixture stirred overnight, allowing it to warm up to room temperature. The reaction was followed by LCMS, and stirring was continued as needed until the starting material was consumed. The reaction mixture was quenched by addition of saturated aqueous ammonium chloride (5 mL) with stirring, concentrated under reduced pressure, diluted with ethyl acetate (10 mL) and diluted with aqueous ammonium chloride (5 mL). The aqueous phase was extracted with ethyl acetate (3×10 mL), and the combined organic phase was successively washed with 2N spdium carbonate (10 mL), 30% ammonium chloride (10 mL), brine (20 mL), and dried over magnesium sulfate. Evaporation of the solvent under reduced pressure gave a crude mixture which was purified by reverse phase HPLC with a gradient of acetonitrile/water (2% to 98%) to afford tert-butyl 2-(1-(2,4-difluorobenzyl)-6-(3-fluoro-4-(trifluoromethyl)phenyl)-7-methoxy-2-oxo-1,2,3,4-tetrahydroquinolin-3-yl)acetate (12 mg, 0.02 mmol, 67%). LCMS m/z 524.0 (M-tBu), 602.0 (M+Na), anal HPLC >98% in purity. $^1$H NMR (400 MHz; acetone-d6) δ7.77 (t, J=8.0 Hz, 1H); 7.60 (m, 2H); 7.38 (m, 2H); 7.11 (m, 1H); 7.00 (m, 1H); 6.81 (s, 1H); 5.35 (s, 2H); 3.80 (s, 3H); 2.70-3.30 (m, 3H); 2.40-2.60 (m, 2H); 1.48 (s, 9H).

2-(1-(2,4-difluorobenzyl)-6-(3-fluoro-4-(trifluoromethyl)phenyl)-7-methoxy-2-oxo-1,2,3,4-tetrahydroquinolin-3-yl)acetic acid was obtained from tert-butyl 2-(1-(2,4-difluorobenzyl)-6-(3-fluoro-4-(trifluoromethyl)phenyl)-7-methoxy-2-oxo-1,2,3,4-tetrahydroquinolin-3-yl)acetate by the hydrolysis procedure described above with 1,4-dioxane/hydrochloric acid.

EXAMPLE 13

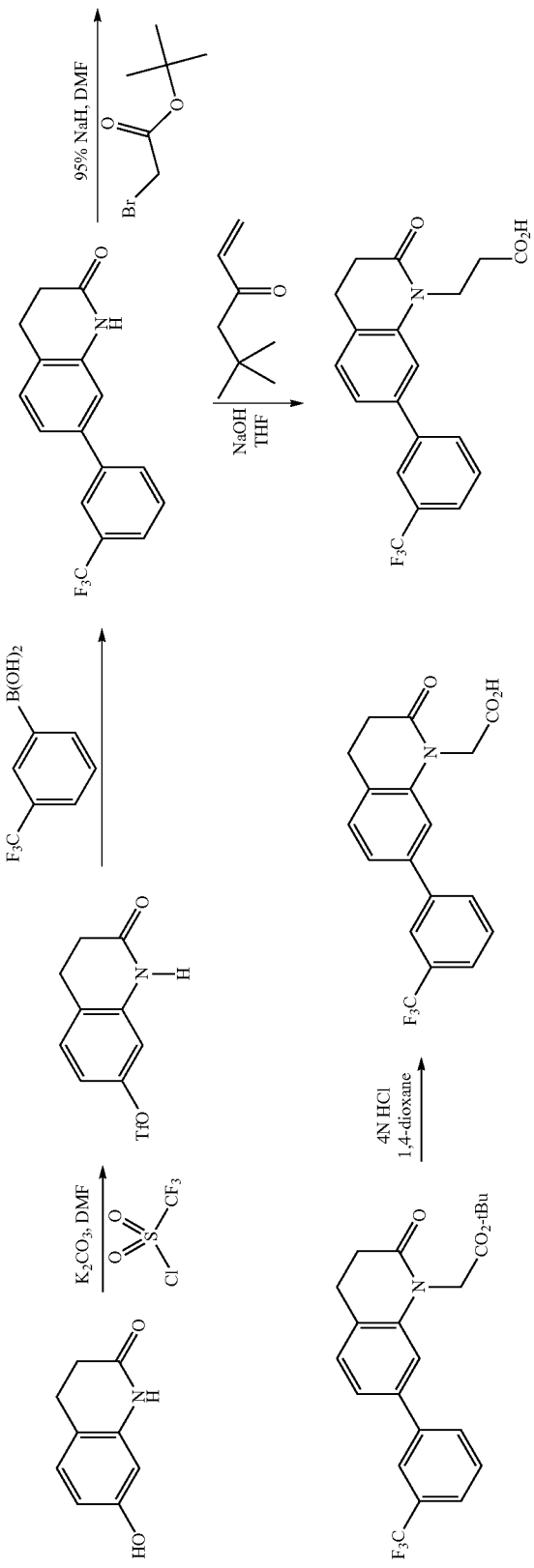
Synthesis of a Compound of Formula (I) in which R[4] is in the 7-Position

A. Preparation of 7-(3-(trifluoromethyl)phenyl)-3,4-dihydroquinolin-2(1H)-one To a solution of 7-hydroxy-3,4-dihydroquinolin-2(1H)-one (3.456 g, 21.18 mmol) in anhydrous N,N-dimethylformamide (25 mL) was added potassium carbonate (4.146 g, 30.00 mmol), then and trifluoromethanesulfonyl chloride (5.000 g, 29.67 mmol) in N,N-dimethylformamide (5 mL) dropwise. The reaction mixture was stirred at room temperature for 24 hours, and a second portion of potassium carbonate (4.146 g, 30.00 mmol) and trifluoromethanesulfonyl chloride (5.000 g, 29.67 mmol) in N,N-dimethylformamide (5 was added slowly, and stirred for 16 hours. Evaporation of the solvent under reduced pressure gave a crude mixture to which a mixture of 15% ethyl acetate in n-hexane (20 mL) and water (50 mL) was added. Diethyl ether (5 mL) was added and the mixture sonicated, filtered, and the solid thus obtained was washed with 3M aqueous potassium carbonate (100 mL), water (200 mL), n-hexane (100 mL), 15% ethyl acetate in n-hexane (30 mL), and dried to afford 2-oxo-1,2,3,4-tetrahydroquinolin-7-yl trifluoromethanesulfonate as a yellow solid (4.311 g, 14.60 mmol, 69%). LCMS mz 295.9 (M+H), 317.9 (M+Na), anal HPLC >90% in purity, $^1$H NMR (400 MHz; CDCl$_3$) δ8.17 (bs, 1H); 7.23 (d, J=8.2 Hz, 1H); 6.90 (dd, J=8.2 and 2.3 Hz, 1H); 6.71 (d, J=2.3 Hz, 1H); 3.00 (m, 2H); 2.67 (m, 2H).

2-oxo-1,2,3,4-tetrahydroquinolin-7-yl trifluoromethanesulfonate was then converted to 7-(3-(trifluoromethyl)phenyl)-3,4-dihydroquinolin-2(1H)-one, reacting with 3-(trifluoromethyl)phenylboronic acid and following the procedure described above in Example 1A above (204 mg, 0.70 mmol, 70%). LCMS mz 292.0 (M+H), 314.0 (M+Na), anal HPLC >99% in purity, $^1$H NMR (400 MHz; CDCl$_3$) δ7.78 (s, 1H); 7.72 (d, J=7.1 Hz, 1H); 7.50-7.64 (m, 2H); 7.49 (bs, 1H); 7.15-7.35 (m, 2H); 6.92 (d, J=1.5 Hz, 1H); 3.03 (m, 2H); 2.69 (m, 2H).

B. Preparation of tert-butyl 2-(2-oxo-7-(3-(trifluoromethyl)phenyl)-3,4-dihydroquinolin-1(2H)-yl) acetate 7-(3-(trifluoromethyl)phenyl)-3,4-dihydroquinolin-2(1H)-one was then converted to tert-butyl 2-(2-oxo-7-(3-(trifluoromethyl)phenyl)-3,4-dihydroquinolin-1(2H)-yl)acetate by reaction with tert-butyl 2-bromoacetate, following the procedures described above in Example 2B. (72 mg, 0.18 mmol, 89%). LCMS mz 350.0 (M+H), 372.0 (M+Na), anal HPLC >96% in purity, $^1$H NMR (400 MHz; acetone-d6) δ7.96 (s, 2H); 7.71 (s, 2H); 7.38 (s, 2H); 7.33 (s, 1H); 4.84 (s, 2H); 3.03 (m, 2H); 2.67 (m, 2H).

C. Preparation of 2-(2-oxo-7-(3-(trifluoromethyl)phenyl)-3,4-dihydroquinolin-1(2H)-yl)acetic acid tert-butyl 2-(2-oxo-7-(3-(trifluoromethyl)phenyl)-3,4-dihydroquinolin-1(2H)-yl)acetate was then converted to 2-(2-oxo-7-(3-(trifluoromethyl)phenyl)-3,4-dihydroquinolin-1(2H)-yl)acetic acid using the procedure described above in Example 2C. (61 mg, 0.17 mmol, 84%). LCMS mz 364.0 (M+H), 386.0 (M+Na), anal HPLC ~100% in purity, $^1$H NMR (400 MHz; acetone-d6) δ8.00 (s, 2H); 7.71 (s, 2H); 7.57 (s, 1H); 7.37 (s, 2H); 4.34 (t, J=7.6 Hz, 2H); 2.98 (m, 2H); 2.72 (m, 2H); 2.61 (m, 2H).

Preparation of other Compounds of Formula (I) in which R$^4$ is in the 7-Position Similarly, following the procedure described in Example 13A, 13B, and 13 C above, but optionally replacing 3-(trifluoromethyl)phenylboronic acid with other optionally substituted aryl boronic acids, the following compounds of Formula I were prepared:

7-(4-(trifluoromethyl)phenyl)-3,4-dihydroquinolin-2(1H)-one;

7-(4-phenoxyphenyl)-3,4-dihydroquinolin-2(1H)-one;

7-(2,4,6-trifluorophenyl)-3,4-dihydroquinolin-2(1H)-one.

EXAMPLE 14

Synthesis of a Deuterated Compound of Formula (I)

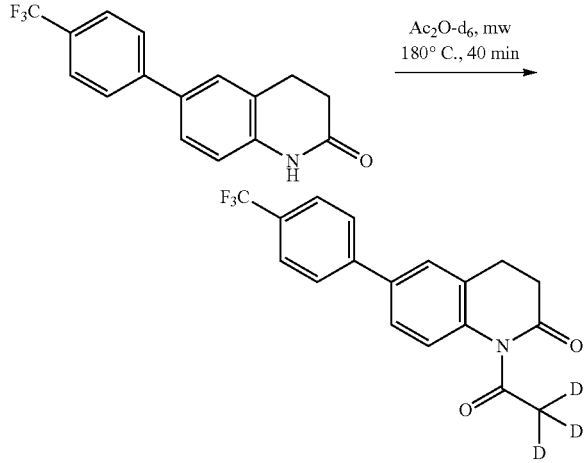

To a Biotage microwave vial was charged 6-(4-(trifluoromethyl)phenyl)-3,4-dihydroquinolin-2(1H)-one (48 mg, 0.16 mmol) and acetic anhydride-D6 (216 mg, 2.00 mmol). The reaction vial was sealed and subjected to microwave irradiation at 180° C. for 40 minutes. The mixture was cooled, transferred to a 25-mL flask, washed with methylene chloride (5 mL), concentrated under reduced pressure, re-dissolved in methylene chloride (20 mL), transferred to a separation funnel, washed with 1N sodium carbonate (10 mL), brine (10 mL), dried over magnesium sulfate, and the solvent removed under reduced pressure. The crude product was purified by preparative HPLC with a gradient acetonitrile/water (5-98%) to afford 1-trideuteroacetyl-6-(4-(trifluoromethyl)phenyl)-3,4-dihydroquinolin-2(1H)-one (50 mg, 0.15 mmol, 93%). LCMS mz 338.1 (M+H), 359.1 (M+Na), anal HPLC >94% in purity.

EXAMPLE 15

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules.

EXAMPLE 16

A tablet Formula (I)s prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets.

EXAMPLE 17

A dry powder inhaler formulation is prepared containing the following components:

| Ingredient | Weight % |
|---|---|
| Active Ingredient | 5 |
| Lactose | 95 |

The active ingredient is mixed with the lactose and the mixture is added to a dry powder inhaling appliance.

EXAMPLE 18

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

EXAMPLE 19

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

EXAMPLE 20

Suspensions, each containing 50 mg of active ingredient per 5.0 mL dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

EXAMPLE 21

A subcutaneous formulation may be prepared as follows:

| Ingredient | Quantity |
|---|---|
| Active Ingredient | 5.0 mg |
| Corn Oil | 1.0 mL |

EXAMPLE 22

An injectable preparation is prepared having the following composition:

| Ingredients | Amount |
|---|---|
| Active ingredient | 2.0 mg/ml |
| Mannitol, USP | 50 mg/ml |
| Gluconic acid, USP | q.s. (pH 5-6) |
| water (distilled, sterile) | q.s. to 1.0 ml |
| Nitrogen Gas, NF | q.s. |

EXAMPLE 23

A topical preparation is prepared having the following composition:

| Ingredients | grams |
|---|---|
| Active ingredient | 0.2-10 |
| Span 60 | 2.0 |
| Tween 60 | 2.0 |
| Mineral oil | 5.0 |
| Petrolatum | 0.10 |
| Methyl paraben | 0.15 |

-continued

| Ingredients | grams |
| --- | --- |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

EXAMPLE 24

Sustained Release Composition

| Ingredient | Weight Range % |
| --- | --- |
| Active ingredient | 50-95 |
| Microcrystalline cellulose (filler) | 1-35 |
| Methacrylic acid copolymer | 1-35 |
| Sodium hydroxide | 0.1-1.0 |
| Hydroxypropyl methylcellulose | 0.5-5.0 |
| Magnesium stearate | 0.5-5.0 |

The sustained release formulations of this invention are prepared as follows: compound and pH-dependent binder and any optional excipients are intimately mixed (dry-blended). The dry-blended mixture is then granulated in the presence of an aqueous solution of a strong base which is sprayed into the blended powder. The granulate is dried, screened, mixed with optional lubricants (such as talc or magnesium stearate), and compressed into tablets. Preferred aqueous solutions of strong bases are solutions of alkali metal hydroxides, such as sodium or potassium hydroxide, preferably sodium hydroxide, in water (optionally containing up to 25% of water-miscible solvents such as lower alcohols).

The resulting tablets may be coated with an optional film-forming agent, for identification, taste-masking purposes and to improve ease of swallowing. The film forming agent will typically be present in an amount ranging from between 2% and 4% of the tablet weight. Suitable film-forming agents are well known to the art and include hydroxypropyl methylcellulose, cationic methacrylate copolymers (dimethylaminoethyl methacrylate/methyl-butyl methacrylate copolymers—Eudragit® E—Röhm. Pharma), and the like. These film-forming agents may optionally contain colorants, plasticizers, and other supplemental ingredients.

The compressed tablets preferably have a hardness sufficient to withstand 8 Kp compression. The tablet size will depend primarily upon the amount of compound in the tablet. The tablets will include from 300 to 1100 mg of compound free base. Preferably, the tablets will include amounts of compound free base ranging from 400-600 mg, 650-850 mg, and 900-1100 mg.

In order to influence the dissolution rate, the time during which the compound containing powder is wet mixed is controlled. Preferably the total powder mix time, i.e. the time during which the powder is exposed to sodium hydroxide solution, will range from 1 to 10 minutes and preferably from 2 to 5 minutes. Following granulation, the particles are removed from the granulator and placed in a fluid bed dryer for drying at about 60° C.

EXAMPLE 25

Activity testing is conducted in the Examples below using methods described herein and those well known in the art.
Sodium Current Screening Assays:

The late sodium current (Late INa) and peak sodium current (Peak INa) assays were performed on an automated electrophysiology platform, PatchXpress 7000A (MDS Analytical Technologies, Sunnyvale, Calif.), which uses the whole cell patch clamp technique to measure currents through the cell membrane of up to 16 cells at a time. The assay used an HEK293 (human embryonic kidney) cell line heterologously expressing the wild-type human cardiac sodium channel, hNa$_v$1.5, purchased from Millipore (Billerica, Mass.). No beta subunits were coexpressed with the Na channel alpha subunit. Cells were maintained with standard tissue culture procedures and stable channel expression was maintained with 400 μg/ml Geneticin in the culture medium. Cells isolated for use on PatchXpress were incubated for 5 minutes in Versene 1× and then for 2 minutes in 0.0125% Trypsin-EDTA (both at 37° C.) to ensure that 80-90% of the cells are single and not part of a cell cluster. Experiments were carried out at 24-27° C.

For both the Late Na and Peak INa assays, series resistance compensation was set to 50% and whole-cell compensation was performed automatically. Currents were low-pass filtered at 10 kHz and digitized at 31.25 kHz. Currents through open sodium channels were automatically recorded and stored in the DataXpress2 database (MDS Analytical Technologies, Sunnyvale, Calif.). Analysis was performed using DataXpress2 analysis software and data are compiled in Excel.

Compound stocks were routinely made in glass vials to 10 mM in dimethyl sulfoxide (DMSO). In some cases, when compounds were not soluble in DMSO, they were made in 100% ethanol. Stocks were sonicated as necessary. The extracellular solution for screening Late INa was composed of: 140 mM NaCl, 4 mM KCl, 1.8 mM CaCl$_2$, 0.75 mM MgCl$_2$, and 5 mM HEPES with pH adjusted to 7.4 using NaOH. The extracellular solution for screening Peak INa was composed of: 20 mM NaCl, 120 mM N-methyl-D glucamine, 4 mM KCl, 1.8 mM CaCl$_2$, 0.75 mM MgCl$_2$, and 5 mM HEPES with pH adjusted to 7.4 using HCl. The intracellular solution used to perfuse the inside of the cells for both the Late Na and Peak INa assays contains: 120 mM CsF, 20 mM CsCl, 5 mM EGTA, 5 mM HEPES and pH adjusted to 7.4 with CsOH. Compounds were diluted in extracellular solution to 10 μM in glass vials and then transferred to glass well plates before robotic addition to the cells. The 0Na extracellular solution used at the end of each experiment for the Late INa and Peak INa assays to measure baseline current contained: 140 mM N-methyl-D-glucamine; 4 mM KCl; 1.8 mM CaCl$_2$; 0.75 mM MgCl$_2$; 5 mM HEPES and pH was adjusted to 7.4 with HCl.

Late INa Screening Assay:

For the Late Na assay, sodium channels were activated every 10 seconds (0.1 Hz) by depolarizing the cell membrane to −20 mV for 250 milliseconds (ms) from a holding potential of −120 mV. In response to a −20 mV voltage step, typical Na$_v$1.5 sodium currents activated rapidly to a peak negative current and then inactivated nearly completely within 3-4 ms.

All compounds were tested to determine their activity in blocking the late sodium current. Late Na current is generated by adding 10 μM Tefluthrin (pyrethroid) to the extracellular solution while recording Na currents. For some experiments, 50 nM ATX II (sea anemone toxin), another late INa activator, was used to generate the late component. Both activators generate late components that are large enough that block of the late component by compounds can be measured easily. For the purposes of the screening, late INa is defined as the mean current between 225 ms and 250 ms after stepping to −20 mV to activate Na channels. After establishing the whole cell recording configuration, late INa activators were added to each well 4 times over a 16-17 minute period so that the late component of the Na current reached a stable value. Compounds were then added (typically at 10 μM), in the presence of late INa activator, with 3 additions over the course of 7 or 8 minutes. Measurements were made typically at the end of exposure to the third compound addition. Measurements were made at the end of exposure to the third compound addition and values were normalized to the current level when all Na$^+$ was removed from the extracellular solution after two additions of 0Na-ECF. Results were reported as percent block of late INa Peak INa Screening Assay:

Compounds were also evaluated for their effect in several other assays, including their effect on Peak INa. After screening compounds against late Na, selected compounds were evaluated for their effect in several other assays, including their effect on peak INa. One goal of this program is to avoid significant block of peak INa. Since the peak INa in our cells can be very large, introducing artifacts in the recording, the concentration of Na$^+$ in the bath is reduced to 20 mM and a nonpermeant cation is added to compensate for the Na$^+$ that was removed to maintain the osmolarity and ionic strength of the solution (see solution details above). All measurements were normalized to the current level when all Na$^+$ is removed from the extracellular solution, after two additions of 0Na-ECF.

In some cases we measured the effect of compound on peak INa using data from the late INa assay. But often peak currents were too large to make this possible, requiring that we perform a separate assay to evaluate the effect on peak INa. For the original peak INa assay, we activated the channel every 10 seconds by depolarizing the cell membrane to −20 mV for 250 ms from a holding potential of −120 mV. After establishing the whole cell recording configuration, the recorded currents were allowed to stabilize for 6-7 minutes. Compound was added at 10 μM with three additions over an 8-9 minute period. Analysis of peak INa generally required correction for rundown before determining the % block of peak current by the tested compound.

A new Peak INa screening assay was developed to allow assessment of the effect of compounds on peak INa at both low and high stimulation frequencies. The goal was to find compounds that are highly selective for block of late INa but do not block peak INa. A low stimulation frequency of 0.1 Hz was used to determine the effect of compound when the channel spends most of the time in the resting (closed) state and provides information about Tonic Block (TB). A higher stimulation frequency (3 Hz) was used to measure block of the channel when it spent more time in the activated and inactivated states, and provided a measure of Use-Dependent Block (UDB). The −100 mV holding potential and the 3 Hz stimulation frequency were chosen so that our benchmark compound would have a small but detectable effect under experimental conditions, allowing for direct comparison of new compounds with the benchmark.

For the new peak INa assay, Na$^+$ channels were activated by depolarizing the cell membrane to 0 mV for 20 ms from a holding potential of −100 mV. After establishing the whole cell recording configuration, channels were stimulated to open with low frequency stimulation (0.1 Hz) for 7 minutes so that we could monitor the recording and assess the extent to which the recording had stabilized. After this stabilization period the stimulation frequency was increased to 3 Hz for 2 minutes, and then returned to 0.1 Hz. Since 3 Hz stimulation caused a small decrease in the peak current even in the absence of compound, we used this internal control for each cell, when no compound was present, to correct the results from 3 Hz stimulation when compound was present. Following 3 Hz stimulation under control conditions, the cell was allowed to recover for 200 seconds before compound was added. Compound (10 μM) was added 3 times at 60 second intervals, while stimulating the channels to open at 0.1 Hz to monitor the progression of block. After the 3$^{rd}$ compound addition, a 320 second wait period was imposed to allow for equilibration before the second period of 3 Hz stimulation begins. TB was measured before the second period of 3 Hz stimulation. Both TB and UDB were analyzed by incorporating rundown correction for the peak INa and UDB was calculated by compensating for the small use-dependent effect of the stimulation protocol on peak INa in the absence of compound.

hERG Screening Assay:

Compounds were screened to test their activity in blocking the hERG potassium channel. The hERG channel was heterologously expressed in a CHO (Chinese Hamster Ovary) cell line. Cells were maintained with standard tissue culture procedures and stable channel expression was maintained with 500 μg/ml G418 in the culture medium. Cells were harvested for testing on the PatchXpress automated patch clamp with Accumax (Innovative Cell Technologies, San Diego, Calif.) to isolate single cells.

The following solutions were used for electrophysiological recordings. The external solution contained: 2 mM $CaCl_2$; 2 mM $MgCl_2$; 4 mM KCl; 150 mM NaCl; 10 mM Glucose; 10 mM HEPES (pH 7.4 with 1M NaOH, osmolarity). The internal solution contained: 140 mM KCl, 10 mM $MgCl_2$, 6 mM EGTA, 5 mM HEPES, 5 mM ATP (pH adjusted to 7.25 with KOH).

hERG channels are activated when the voltage is stepped to +20 mV from the −80 mV holding potential. During a 5 second step at +20 mV, the channels activated and then largely inactivated, so the currents were relatively small. Upon returning to −50 mV from +20 mV, hERG currents transiently became much larger as inactivation was rapidly removed and then the channel closed. The first step to −50 mV for 300 ms was used as a baseline for measuring the peak amplitude during the step to −50 mV after channel activation. The peak current at −50 mV was measured both under control conditions and after addition of compound.

All compounds were prepared as 10 mM DMSO stocks in glass vials. Stock solutions were mixed by vigorous vortexing and sonication for about 2 minutes at room temperature. For testing, compounds were diluted in glass vials using an intermediate dilution step in pure DMSO and then further diluted to working concentrations in external solution. Dilutions were prepared no longer than 20 minutes before use.

After achieving the whole-cell configuration, cells were monitored for 90 seconds to assess stability and washed with external solution for 66 seconds. The voltage protocol described above was then applied to the cells every 12 seconds and throughout the whole procedure. Only cells with stable recording parameters and meeting specified health criteria were allowed to enter the compound addition procedure.

External solution containing 0.1% DMSO (vehicle) was applied to the cells first to establish the control peak current amplitude. After allowing the current to stabilize for 3 to 5 minutes, 1 μM and then 10 μM test compounds were applied. Each compound concentration was added 4 times and cells were kept in test solution until the effect of the compound reached steady state or for a maximum of 12 minutes. After addition of test compound, a positive control (1 µM Cisapride) was added—it must block >95% of the current for the experiment to be considered valid. Washout in the external solution compartment was performed until the recovery of the current reached steady state. Data were analyzed using DataXpress, Clampfit (Molecular Devices, Inc., Sunnyvale) and Origin 7 (Originlab Corp.)

L-type Calcium Channel Activity Well-Plate Assay:

Cell Culture: IMR-32 (human neuroblastoma) cells were obtained from The American Type Culture Collection. The cells were maintained in MEM supplemented with 10% fetal bovine serum, 2 mM of L-glutamine, 100 IU/ml of penicillin, 50 µg/ml of streptomycin, 1% of sodium pyruvate, 1% of sodium bicarbonate and 1% of non-essential amino acid. The cells were cultured at 37° C. in a humidified 5% $CO_2$/95% air incubator. Culture medium was changed every two days and cells were recultivated when they reached 70-80% confluent.

Assay: IMR-32 cells were seeded on a Microtest 96-well Assay Plate (BD FALCON™) at a density of 200,000 cells/well in 200 µl culture medium for overnight. The culture medium was removed, and replaced by 120 µl Ca-4 dye (MDS Analytical Technologies, Sunnyvale, Calif.) in HBSS (1× Hank's Balanced Salt solution plus 20 mM HEPES, pH 7.4) containing 2 mM probenecid. Cells were then incubated for 1 hour at 37° in incubator. Testing compounds were diluted from 5 µM-50 µM in HBSS, and 40 µl were added in cells before assay. L-type calcium channel activities (Max-Min) were measured after addition of 40 µl of 1 µM (−)Bay K 8644 plus 50 mM KCl (final concentration) using FlexStation (Molecular Devices) immediately after addition of testing compounds. The inhibition of L-type calcium channel activity by compounds was then calculated.

Compounds were tested and found to be effective using the described assay methods at a concentration of 1 µM and 10 µM in the late INa and Peak INa assays, and at 1 µM and 10 µM for the hERG and L-type calcium channel assays. The assay results demonstrated that the compounds tested showed activity as modulators of late sodium current, for example by inhibiting (or reducing) the late sodium current.

Compounds were tested using the described assay methods. Data was obtained obtained by testing the listed compounds at 10 µM and 1 µM concentrations in the late INa assay, and at 1 µM and 10 µM for the hERG and L-type calcium channel assays. Data are shown in Table 1 below for those compounds that inhibit Late Ina by at least 10% at the 10 µM concentration.

TABLE 1

| Cmpd No. | Late INa % blk (10 µM test cmpd) | Late INa % blk (1 µM test cmpd) | hERG Patch Clamp hERG % blk 1 µm | hERG Patch Clamp hERG % blk 10 µm |
|---|---|---|---|---|
| 1 | 74 | | 10 | 19 |
| 2 | 16 | | | |
| 3 | 29 | | | |
| 4 | 48 | | 10 | 16 |
| 5 | 30 | | | |
| 6 | 23 | | | |
| 7 | 52 | | | |
| 8 | 22 | | | |
| 21 | 65 | | 11 | 36 |
| 9 | 62 | | | |
| 10 | 66 | 40 | | |
| 11 | 54 | | | |
| 12 | 27 | | | |
| 13 | 70 | | | |
| 22 | 67 | | | |
| 14 | 29 | | 10 | 28 |
| 23 | 33 | | | |
| 15 | 36 | | 13 | 59 |
| 16 | 24 | | | |
| 24 | 74 | 44 | | |
| 44 | 21 | | 10 | 10 |
| 25 | 20 | | 26 | 32 |
| 60 | 25 | | 10 | 10 |
| 26 | 20 | | 10 | 10 |
| 27 | 52 | | 12 | 47 |
| 28 | 18 | | | |
| 88 | 40 | | | |
| 29 | 69 | | 11 | 97 |
| 30 | 86 | 47.9 | | |
| 89 | 42 | | 24 | 67 |
| 31 | 26 | | | |
| 32 | 27 | | | |
| 33 | 77 | 38.1 | | |
| 37 | 19 | | | |
| 90 | 22 | | | |
| 49 | 60 | | 10 | 42 |
| 34 | 60 | | 13 | 37 |
| 50 | 76 | | | |
| 51 | 14 | | | |
| 53 | 73 | | | |
| 35 | 69 | | | |
| 89 | 48 | | 16 | 72 |
| 44 | 48 | | | |
| 45 | 64 | | | |
| 38 | 53 | | | |
| 39 | 60 | | 12 | 96 |
| 40 | 64 | | | |
| 66 | 27 | | | |
| 67 | 74 | | | |
| 68 | 23 | | | |
| 69 | 16 | | 10 | 10 |
| 70 | 17 | | 10 | 10 |
| 41 | 12 | | | |
| 54 | 13 | | | |
| 55 | 14 | | | |
| 56 | 14 | | | |
| 58 | 13 | | 10 | 10 |
| 77 | 72 | | | |
| 78 | 34 | | | |
| 79 | 12 | | | |
| 80 | 17 | | | |
| 81 | 30 | | | |
| 105 | 40 | | | |
| 42 | 19 | | | |
| 59 | 10 | | | |
| 86 | 13 | | | |
| 87 | 20 | | | |
| 19 | 31 | | | |
| 74 | 20 | | | |
| 91 | 31 | | | |
| 82 | 54 | | | |

The assay results shown in the above Table 1 establish that compounds tested showed activity as modulators of late sodium current, for example by inhibiting (or reducing) the late sodium current.

In some embodiments the effects of a compound of Formula (I) are specific for the late sodium current and show little or no activity with respect to one or more other ion channels. Thus, in some embodiments, a compound having an activity of reducing late sodium current will also exhibit little or no activity with regard to the peak sodium current. In particular embodiments, a compound having an activity of reducing late sodium current will also exhibit little or no activity with regard to the hERG potassium channel. In some embodiments, a compound having an activity of reducing late sodium current will also exhibit little or no activity with regard to the L-type calcium channel. For example, a given compound may provide a 30% (or greater, e.g. more than 40%, more than 50%, more than 60%, more than 70%, more than 80%) reduction in late sodium current in the assay described herein, and the same compound may exhibit little or no activity for one or more of the peak sodium current, the hERG potassium channel, and the L-type calcium channel. In this regard, a compound having "little" effect will typically show less then a 30% reduction (e.g. less than a 20% reduction, less than a 15% reduction, less than a 10% reduction) in the given activity (e.g. Peak INa, hERG, L-type calcium), when measured using the assay described herein. In this regard, "no" effect means that any activity measured will differ from the control by less than the standard error of the measurement. The assays conducted to measure activities in this regard should be performed as described above, with the compound at a concentration of 10 µM (or at the upper limit of solubility, if less).

L-type Ca2+ Channel Assay—ChanTest

Selected compounds were screened for block of the cardiac L-type $Ca^{2+}$ channel (hCav1.2, encoded by the human CACNA1C gene and coexpressed with the beta 2 subunit, encoded by the human CACNB2 gene, and alpha2delta1, encoded by the CACNA2D1 gene). The $Ca^{2+}$ channel was heterologously expressed in a CHO (Chinese Hamster Ovary) cell line. Cells were maintained following standard tissue culture procedures and stable channel expression was maintained with appropriate selection antibiotics in the culture medium. Cells were harvested for testing on the PatchXpress automated patch clamp (Model 7000A, Molecular Devices, Sunnyvale, Calif.) by washing twice with Hank's Balanced Salt Solution, treating the cells with trypsin, and re-suspending cells in culture medium (4-6×$10^6$ cells in 20 mL). Cells in suspension were allowed to recover for 10 minutes in a tissue culture incubator set at 37° C. in a humidified 95% air, 5% $CO_2$ atmosphere.

The following solutions were used for electrophysiological recordings. The external solution contains (mM): 137 NaCl, 4 KCl, 1.8 $CaCl_2$, 1 $MgCl_2$, 10 Glucose, 10 HEPES (pH 7.4 with NaOH). The internal solution contains (mM): 130 Cs Aspartate, 5 $MgCl_2$, 5 EGTA, 4 ATP, 0.1 GTP, 10 HEPES, (pH adjusted to 7.2 with N-methyl-D-glucamine).

Vehicle was applied to naïve cells (n≥2, where n=the number cells), for a 5-10 minute exposure interval. Each solution exchange was performed in quadruplicate. At the end of each experiment, a saturating concentration of nifedipine (10 µM) was added to block hCav1.2 current. Leak current was digitally subtracted from the total membrane current record.

Test compound stock solutions were prepared by addition of dimethyl sulfoxide (DMSO) and stored frozen. Each test compound DMSO stock was sonicated (Model 2510/5510, Branson Ultrasonics, Danbury, Conn.), at ambient room temperature for at least 20 minutes to facilitate dissolution. Test compound concentrations were prepared fresh daily by diluting stock solutions into the standard extracellular physiological saline solution (see above). The maximum percent of DMSO added with compound was 0.1%. All test compound and control solutions were placed in a glass-lined 96-well compound plate before loading on PatchXpress.

One or two concentrations (1, 10 µM) of each test compound was applied at five (5) minute intervals via disposable polyethylene micropipette tips to naïve cells (n 2, where n=the number cells/concentration). Each test compound concentration was added to the cell in quadruplicate. Total duration of exposure to each test compound concentration was 5 minutes.

Onset and steady state block of hCav1.2 channels was measured using a stimulus voltage pattern consisting of a depolarizing test pulse (duration, 200 ms; amplitude, 10 mV) at 10 s intervals from a −80 mV holding potential. Peak current was measured during a step to 10 mV.

In particular embodiments, a compound will exhibit a high selectivity for the late sodium current modulatory activity as compared to the activity in one or more other ion channels. The selectivity of a compound may be determined by determining the percentage reduction in late sodium current due to the compound, as measured by the assay described above. The percentage reduction in one other ion channel activity, such as the hERG potassium channel or L-type calcium channel, due to the compound is determined as described above. The selectivity is determined by taking the ratio of (percentage reduction in late sodium current) to (percentage reduction in one other ion channel activity). The assays conducted to measure activities in this regard should be performed as described above, with the compound at a concentration of 10 µM (or at the upper limit of solubility, if less). In particular embodiments, the selectivity of a compound of the invention will be at least 5:1, e.g. at least 6:1, at least 7:1, at least 8:1, at least 9:1, at least 10:1, at least 12:1, at least 15:1, at least 20:1, or at least 25:1, when comparing the percentage reduction in late sodium current versus percentage reduction of one of the peak sodium current, the hERG potassium channel current, or the L-type calcium channel.

What is claimed is:

1. A compound selected from the group consisting of:
2-{2-oxo-6-[4-(trifluoromethoxy)phenyl]-3,4-dihydroquinolin-1(2H)-yl}acetamide;
2-[6-(2,4-difluorophenyl)-2-oxo-3,4-dihydroquinolin-1 (2H)-yl]acetamide;
2-{2-oxo-6-[4-(trifluoromethyl)phenyl]-3,4-dihydroquinolin-1 (2H)-yl}acetamide;
2-{6-[4-chloro-3-(trifluoromethyl)phenyl]-2-oxo-3,4-dihydroquinolin-1(2H)-yl}acetamide;
tert-butyl 2-(6-(3-fluoro-4-(trifluoromethyl)phenyl)-2-oxo-3,4-dihydroquinolin-1(2H)-yl)acetate;
tert-butyl[6-(2,4-difluorophenyl)-2-oxo-3,4-dihydroquinolin-1(2H)-yl]acetate;
tert-butyl[6-(4-fluorophenyl)-2-oxo-3,4-dihydroquinolin-1(2H)-yl]acetate;
tert-butyl {2-oxo-6-[4-(trifluoromethoxy)phenyl]-3,4-dihydroquinolin-1 (2H)-yl}acetate;
tert-butyl {6-[4-chloro-3-(trifluoromethyl)phenyl]-2-oxo-3,4-dihydroquinolin-1(2H)-yl}acetate;
ethyl {2-oxo-6-[3-(trifluoromethoxy)phenyl]-3,4-dihydroquinolin-1(2H)-yl}acetate;
tert-butyl[6-(3-chlorophenyl)-2-oxo-3,4-dihydroquinolin-1(2H)-yl]acetate;
tert-butyl {2-oxo-6-[4-(trifluoromethyl)phenyl]-3,4-dihydroquinolin-1(2H)-yl}acetate;
ethyl[6-(2,4-difluorophenyl)-2-oxo-3,4-dihydroquinolin-1(2H)-yl]acetate;
tert-butyl[6-(4-chlorophenyl)-2-oxo-3,4-dihydroquinolin-1(2H)-yl]acetate;
ethyl[6-(3,4-difluorophenyl)-2-oxo-3,4-dihydroquinolin-1(2H)-yl]acetate;
{2-oxo-6-[3-(trifluoromethoxy)phenyl]-3,4-dihydroquinolin-1(2H)-yl}acetic acid;

[6-(4-chlorophenyl)-2-oxo-3,4-dihydroquinolin-1(2H)-yl]acetic acid;
{2-oxo-6-[4-(trifluoromethyl)phenyl]-3,4-dihydroquinolin-1 (2H)-yl}acetic acid;
2-(6-(3-fluoro-4-(trifluoromethyl)phenyl)-2-oxo-3,4-dihydroquinolin-1(2H)-yl)acetic acid;
ethyl {2-oxo-6-[4-(trifluoromethoxy)phenyl]-3,4-dihydroquinolin-1(2H)-yl}acetate;
[6-(4-fluorophenyl)-2-oxo-3,4-dihydroquinolin-1(2H)-yl]acetic acid;
[6-(3-chloro-4-fluorophenyl)-2-oxo-3,4-dihydroquinolin-1(2H)-yl]acetic acid;
sodium {2-oxo-6-[4-(trifluoromethyl)phenyl]-3,4-dihydroquinolin-1 (2H)-yl}acetate;
[6-(3,4-dichlorophenyl)-2-oxo-3,4-dihydroquinolin-1 (2H)-yl]acetic acid;
{2-oxo-6-[4-(trifluoromethoxy)phenyl]-3,4-dihydroquinolin-1 (2H)-yl}acetic acid;
[6-(4-chloro-3-fluorophenyl)-2-oxo-3,4-dihydroquinolin-1(2H)-yl]acetic acid;
ethyl {2-oxo-6-[4-(trifluoromethyl)phenyl]-3,4-dihydroquinolin-1(2H)-yl}acetate;
[6-(3-fluorophenyl)-2-oxo-3,4-dihydroquinolin-1(2H)-yl] acetic acid;
tert-butyl 2-(6-(3,4-dichlorophenyl)-2-oxo-3,4-dihydroquinolin-1(2H)-yl)acetate; and
tert-butyl-2-(7-methoxy-2-oxo-6-(4-(trifluoromethyl) phenyl)-3,4-dihydroquinolin-1 (2H)-yl)acetate; or a pharmaceutically acceptable salt thereof.

2. A compound selected from the group consisting of:
7-methoxy-6-[4-(trifluoromethyl)phenyl]-3,4-dihydroquinolin-2(1H)-one;
8-bromo-6-(4-chlorophenyl)-7-methoxy-3,4-dihydroquinolin-2(1H)-one;
6,8-bis(4-chlorophenyl)-7-methoxy-3,4-dihydroquinolin-2(1H)-one;
[6,8-bis(4-chlorophenyl)-7-methoxy-2-oxo-3,4-dihydroquinolin-1(2H)-yl]acetic acid;
6-(3-fluorophenyl)-1-methyl-3,4-dihydroquinolin-2(1H)-one;
6-(2,4-difluorophenyl)-1-(2-methoxyethyl)-3,4-dihydroquinolin-2(1H)-one;
1-(2-hydroxypropyl)-6-[4-(trifluoromethoxy)phenyl]-3,4-dihydroquinolin-2(1H)-one;
1-(2-hydroxyethyl)-6-[4-(trifluoromethoxy)phenyl]-3,4-dihydroquinolin-2(1H)-one;
6-(3,4-difluorophenyl)-1-(2-hydroxyethyl)-3,4-dihydroquinolin-2(1H)-one;
1-(2-hydroxyethyl)-6-[4-(trifluoromethyl)phenyl]-3,4-dihydroquinolin-2(1H)-one;
6-(2,4-difluorophenyl)-1-(2-hydroxyethyl)-3,4-dihydroquinolin-2(1H)-one;
6-(2,4-difluorophenyl)-1-(2,2,2-trifluoroethyl)-3,4-dihydroquinolin-2(1H)-one;
{2-oxo-6-[4-(trifluoromethyl)phenyl]-3,4-dihydroquinolin-1 (2H)-yl}acetonitrile;
6-(2,4-difluorophenyl)-1-[2-hydroxy-3-(2-methoxyphenoxy)propyl]-3,4-dihydroquinolin-2(1H)-one;
6-[3-(trifluoromethyl)phenyl]-3,4-dihydroquinolin-2 (1H)-one;
6-[4-chloro-3-(trifluoromethyl)phenyl]-3,4-dihydroquinolin-2(1H)-one;
6-[4-(trifluoromethoxy)phenyl]-3,4-dihydroquinolin-2 (1H)-one;
6-(2,4-difluorophenyl)-3,4-dihydroquinolin-2(1H)-one;
6-(2-fluorophenyl)-3,4-dihydroquinolin-2(1H)-one;
6-(4-fluorophenyl)-3,4-dihydroquinolin-2(1H)-one;
2-fluoro-5-(2-oxo-1,2,3,4-tetrahydroquinolin-6-yl)benzonitrile;
3-(2-oxo-1,2,3,4-tetrahydroquinolin-6-yl)benzamide;
6-(3-acetylphenyl)-3,4-dihydroquinolin-2(1H)-one;
4-(2-oxo-1,2,3,4-tetrahydroquinolin-6-yl)benzamide;
3-(2-oxo-1,2,3,4-tetrahydroquinolin-6-yl)benzonitrile; and
6-[3-(morpholin-4-ylcarbonyl)phenyl]-3,4-dihydroquinolin-2(1H)-one; or a pharmaceutically acceptable salt thereof.

3. A method of treating a disease state in a mammal that is alleviable by treatment with an agent capable of reducing late sodium current, wherein the disease state is a cardiovascular disease selected from one or more of atrial and ventricular arrhythmias, heart failure, congestive heart failure, diastolic heart failure, systolic heart failure, acute heart failure, Prinzmetal's (variant) angina, stable and unstable angina, exercise induced angina, ischemia, recurrent ischemia, reperfusion injury, myocardial infarction, acute coronary syndrome, peripheral arterial disease, or intermittent claudication, comprising administering to a mammal in need thereof a therapeutically effective dose of a compound of claim 1.

4. A method of treating a disease state in a mammal that is alleviable by treatment with an agent capable of reducing late sodium current, wherein the disease state is a cardiovascular disease selected from one or more of atrial and ventricular arrhythmias, heart failure, congestive heart failure, diastolic heart failure, systolic heart failure, acute heart failure, Prinzmetal's (variant) angina, stable and unstable angina, exercise induced angina, ischemia, recurrent ischemia, reperfusion injury, myocardial infarction, acute coronary syndrome, peripheral arterial disease, or intermittent claudication, comprising administering to a mammal in need thereof a therapeutically effective dose of a compound of claim 2.

5. The method of claim 3, wherein the disease state is diabetes or diabetic peripheral neuropathy.

6. The method of claim 4, wherein the disease state is diabetes or diabetic peripheral neuropathy.

7. A pharmaceutical composition comprising a pharmaceutically acceptable excipient and a therapeutically effective amount of a compound of claim 1.

8. A pharmaceutical composition comprising a pharmaceutically acceptable excipient and a therapeutically effective amount of a compound of claim 2.

* * * * *